(12) United States Patent
Gruss et al.

(10) Patent No.: US 9,133,142 B2
(45) Date of Patent: Sep. 15, 2015

(54) SALTS OR CO-CRYSTALS OF 3-(3-DIMETHYLAMINO-1-ETHYL-2-METHYL-PROPYL)-PHENOL

(75) Inventors: Michael Gruss, Aachen (DE); Magda Kraszewski, Aachen (DE)

(73) Assignee: Gruenenthal GmbH, Aachen (DE)

( * ) Notice: Subject to any disclaimer, the term of this patent is extended or adjusted under 35 U.S.C. 154(b) by 338 days.

(21) Appl. No.: 13/188,689

(22) Filed: Jul. 22, 2011

(65) Prior Publication Data

US 2012/0022117 A1 Jan. 26, 2012

Related U.S. Application Data

(60) Provisional application No. 61/367,159, filed on Jul. 23, 2010.

(30) Foreign Application Priority Data

Jul. 23, 2010 (EP) .................................... 10007672

(51) Int. Cl.
| | | |
|---|---|---|
| *A61K 31/137* | (2006.01) | |
| *A61K 31/455* | (2006.01) | |
| *C07D 213/80* | (2006.01) | |
| *C07D 275/06* | (2006.01) | |
| *C07C 55/02* | (2006.01) | |
| *C07C 55/08* | (2006.01) | |
| *C07C 55/20* | (2006.01) | |
| *C07C 57/15* | (2006.01) | |
| *C07C 63/08* | (2006.01) | |
| *C07C 63/36* | (2006.01) | |
| *C07C 65/11* | (2006.01) | |
| *C07C 215/54* | (2006.01) | |
| *C07D 239/545* | (2006.01) | |
| *C07D 291/06* | (2006.01) | |

(52) U.S. Cl.
CPC .............. *C07D 275/06* (2013.01); *C07C 55/02* (2013.01); *C07C 55/08* (2013.01); *C07C 55/20* (2013.01); *C07C 57/15* (2013.01); *C07C 63/08* (2013.01); *C07C 63/36* (2013.01); *C07C 65/11* (2013.01); *C07C 215/54* (2013.01); *C07D 239/545* (2013.01); *C07D 291/06* (2013.01); *A61K 31/137* (2013.01); *A61K 31/455* (2013.01); *C07B 2200/07* (2013.01); *C07D 213/80* (2013.01)

(58) Field of Classification Search
CPC ... A61K 31/137; A61K 31/455; C07D 213/80
USPC .................................. 514/356, 654; 546/318
See application file for complete search history.

(56) References Cited

U.S. PATENT DOCUMENTS

| | | | |
|---|---|---|---|
| 6,248,737 B1 | 6/2001 | Buschmann et al. | |
| 2005/0058706 A1 | 3/2005 | Bartholomaeus et al. | |
| 2005/0176790 A1* | 8/2005 | Bartholomaus et al. | ...... 514/373 |
| 2008/0269326 A1 | 10/2008 | Christoph et al. | |
| 2009/0258948 A1* | 10/2009 | Bartholomaus et al. | ...... 514/649 |
| 2010/0272815 A1* | 10/2010 | Khunt et al. | .................. 424/489 |

FOREIGN PATENT DOCUMENTS

| | | |
|---|---|---|
| CA | 2 439 269 C | 11/2011 |
| CN | 1561203 A | 1/2005 |
| EP | 0 693 475 A1 | 1/1996 |
| JP | 8-99939 A | 4/1996 |
| JP | 2004-527491 A | 9/2004 |
| WO | WO 02/067651 A2 | 9/2002 |
| WO | WO 03/035053 A1 | 5/2003 |
| WO | WO 2008/110323 A1 | 9/2008 |
| WO | WO 2009/067703 A2 | 5/2009 |

OTHER PUBLICATIONS

"Tapentadol hydrochloride", Chinese Journal of Medicinal Chemistry, Chinese Pharmaceutical Chemistry magazine, vol. 19, 2009, (one (1) page).

Camille G. Wermuth, <<Preparation of Water-Soluble Compounds Through Salt Formation>>, The Practice of Medicinal Chemistry ,1996 (thirty-seven (37) pages).

* cited by examiner

*Primary Examiner* — Jennifer M Kim
(74) *Attorney, Agent, or Firm* — Crowell & Moring LLP

(57) ABSTRACT

A salt or cocrystal of 3-(3-dimethylamino-1-ethyl-2-methylpropyl)-phenol (component a) and at least one acid component (b1) or at least one acid component (b2), wherein the salt or cocrystal of component (a) and component (b2) is present in crystalline and/or amorphous form, a pharmaceutical composition comprising said salt or cocrystal, and a method of treating pain in a subject in need thereof by administering an effective amount of said salt or cocrystal.

17 Claims, 26 Drawing Sheets

SALTS OR CO-CRYSTALS OF 3-(3-DIMETHYLAMINO-1-ETHYL-2-METHYL-PROPYL)-PHENOL

CROSS REFERENCE TO RELATED APPLICATIONS

This application claims priority from co-pending U.S. provisional patent application No. 61/367,159, filed Jul. 23, 2010 and from European patent application no. EP 10 007 672.8, also filed Jul. 23, 2010, the entire disclosure of each of which is incorporated herein by reference.

BACKGROUND OF THE INVENTION

The invention relates to a salt or cocrystal of 3-(3-dimethylamino-1-ethyl-2-methyl-propyl)-phenol (component a) and at least one acid component (b1) or at least one acid component (b2), wherein the salt or cocrystal of component (a) and component (b2) is present in crystalline and/or amorphous form, a medicament comprising said salt or cocrystal as well as said salt or cocrystal for use in the treatment of pain.

3-(3-Dimethylamino-1-ethyl-2-methyl-propyl)-phenol compounds such as e.g. (1R,2R)-3-(3-dimethylamino-1-ethyl-2-methyl-propyl)-phenol, which is also known as tapentadol (CAS no. 175591-23-8) are synthetic, centrally acting analgesics which are effective in the treatment of pain.

Tapentadol exhibits a dual mechanism of action, on the one hand as a µ-opioid receptor agonist and on the other as a noradrenaline transporter inhibitor. In humans, the affinity of tapentadol to the recombinantly produced µ-opioid receptor is 18-times less than that of morphine. However, clinical studies have shown the pain-alleviating action of tapentadol to be only two to three times less than that of morphine. The only slightly reduced analgesic efficacy with a simultaneously 18-times reduced affinity to the recombinant µ-opioid receptor indicates that the noradrenaline transporter inhibiting property of tapentadol also contributes to its analgesic efficacy. Consequently, it may be assumed that tapentadol has a similar analgesic efficacy to that of pure µ-opioid receptor agonists but has fewer of the side effects associated with the µ-opioid receptor. The compound can be used in the form of its free base or as a salt or solvate. The production of the free tapentadol base and its hydrochloride salt are known for example from EP-A 0 693 475.

Conventional formulations for oral administration of a 3-(3-dimethylamino-1-ethyl-2-methyl-propyl)-phenol compound such as tapentadol usually lead to rapid release of the active substance in the gastrointestinal tract, thereby leading to a rather rapid onset of its analgesic action. Subsequently, a rather rapid reduction in the action is observed. In order to achieve an effective analgesic action over a prolonged period of time, i.e. to ensure an adequately high concentration of the active substance in the patient's blood plasma, it is therefore necessary to administer the pharmaceutical composition comprising said active substance at relatively short time intervals. However, the need for frequent dosing may lead to errors in administration and to undesirable variations in the concentration of the compound in the blood plasma which could be detrimental to patient compliance and the therapeutic benefit, particularly when treating chronically painful conditions.

In order to overcome such disadvantages of conventional formulations, EP-A 1 439 829 suggests providing a delayed-release pharmaceutical composition suitable for oral administration comprising 3-(3-dimethylamino-1-ethyl-2-methyl-propyl)-phenol or its hydrogen chloride salt by means of retardation, i.e. by means of a matrix, a coating or in a release system based on osmotic action. Since the hydrogen chloride salt of 3-(3-dimethylamino-1-ethyl-2-methyl-propyl)-phenol has a high solubility in water and aqueous media, the manufacture of such a delayed-release formulation by retardation is considered necessary in order to achieve a controlled release of 3-(3-dimethylamino-1-ethyl-2-methyl-propyl)-phenol subsequent to administration.

However, there is still a need for alternative administration forms comprising a 3-(3-dimethylamino-1-ethyl-2-methyl-propyl)-phenol compound such as tapentadol by which a controlled release of the active substance can be achieved. Further, there is a need for such administration forms which do not necessarily have to be formulated using additional means of retardation.

SUMMARY OF THE INVENTION

It was therefore an object of the present invention to provide a 3-(3-dimethylamino-1-ethyl-2-methyl-propyl)-phenol compound in a form suitable for administration, in particular in a solid form, e.g. for oral administration, which has advantages over the prior art, for example with respect to solubility, absorbability, concentration in the blood, or bioavailability of the pharmacologically active compound.

Another object of the present invention was to provide a 3-(3-dimethylamino-1-ethyl-2-methyl-propyl)-phenol compound in a form suitable for administration, e.g. in a solid form, which allows for a controlled release of the 3-(3-dimethylamino-1-ethyl-2-methyl-propyl)-phenol compound, without having necessarily to be present in a delayed-release form by retardation as e.g. described in EP-A 1 439 829 or by depot formulation.

These objects have been achieved by the pharmaceutical salts or co-crystals according to the present invention.

It has been surprisingly found that a 3-(3-dimethylamino-1-ethyl-2-methyl-propyl)phenol compound as component (a) in the form of a salt or cocrystal with at least one acid (b1) or (b2) according to the present invention allows for the control of solubility, preferably of solubility in an aqueous medium such as water, of said salt or cocrystal and, thus of its component (a). This facilitates release in a targeted manner.

Particularly, it has been surprisingly found that said control of the solubility of component (a) can be influenced by the solubility of the inventive salt or cocrystal, i.e. by the choice of the acid (b1) or (b2), e.g. by employing an acid (b1) or (b2) for the formation of the inventive salt or cocrystal, which is less soluble in an aqueous medium such as water than for instance a hydrochloric acid addition salt (but which still has a sufficient or good solubility in said medium necessary for the desired form of administration such as oral administration), thereby leading to a different solubility profile, in particular a reduced solubility profile, and thus to a different pharmacokinetic profile of the resulting salt or cocrystal and, thus, to a controlled release profile of its component (a).

Therefore, the inventive salt or cocrystal allows for a controlled release of the 3-(3-dimethylamino-1-ethyl-2-methyl-propyl)phenol compound due to an intrinsic property of said salt or cocrystal by choice of at least one suitable acid (b1) or (b2). Thus, in contrast to conventional formulations comprising 3-(3-dimethylamino-1-ethyl-2-methyl-propyl)phenol compound, e.g. a formulation comprising the highly water-soluble hydrochloric acid addition salt of tapentadol, the inventive salts or cocrystals do not necessarily have to be provided in form of a delayed release form by means of a matrix, a coating or in a release system displaying an osmotic action as described in EP-A 1 439 829, or in a depot formulation in order to achieve the desired controlled release properties.

Thus, in one of its aspects the present invention relates to a salt or cocrystal of (a) 3-(3-dimethylamino-1-ethyl-2-methyl-propyl)-phenol, and (b1) at least one acid selected from the group consisting of hydrogen fluoride, hydrogen iodide, boric acid, nitric acid, carbonic acid, phosphoric acid, peracetic acid, periodic acid, sulfamic acid, sulfurous acid, thioacetic acid, thiodipropionic acid, trifluoromethane sulfonic acid, trimethylacetic acid, tertiary butylacetic acid, 2,2-dichloro-acetic acid, thiocyanic acid, isethionic acid, acetylaminoacetic acid, propionic acid, 2-mercaptopropionic acid, butyric acid, isobutyric acid, valeric acid, 2-methylvaleric acid, isovaleric acid, 2-methylbutyric acid, hexanoic acid (caproic acid), 2-ethylbutyric acid, 3-methylpentanoic acid, 4-methylpentanoic acid, heptanoic acid, (E)-2-heptenoic acid, 2-methylhexanoic acid, 5-methylhexanoic acid, octanoic acid (caprylic acid), 2-methylheptanoic acid, 4-methyloctanoic acid, nonanoic acid, decanoic acid (capric acid), 4-methylnonanoic acid, undecanoic acid, 4-ethyloctanoic acid, lauric acid, myristic acid, palmitic acid, octadecanoic acid (stearic acid), (E)-2-butenoic acid, trans-2-methyl-2-butenoic acid, 3-methylcrotonic acid, 2-pentenoic acid, 4-pentenoic acid, trans-2-hexenoic acid, 3-hexenoic acid, 2-methyl-2-pentenoic acid, 2-methyl-3-pentenoic acid, 2-methyl-4-pentenoic acid, 4-methylpent-2-enoic acid, 2,4-dimethyl-2-pentenoic acid, (E)-2-octenoic acid, (E)-2-nonenoic acid, 4-decenoic acid, 5-decenoic acid, 6-decenoic acid, 9-decenoic acid, (E)-2-decenoic acid, 3,7-dimethyl-6-octenoic acid, 10-undecenoic acid, oleic acid, L-(+)-tartaric acid, dibenzoyltartaric acid, (2S,3S)-dibenzoyltartaric acid, L-(−)-malic acid, D-(+)-malic acid, L-(+)-lactic acid, (S)-(+)-mandelic acid, glutaric acid, adipic acid, sebacic acid, monomethyl sebacic acid, glycolic acid, 2-hydroxysuccinic acid, linoleic acid, ethanesulfonic acid, ethane-1,2-disulfonic acid, hexane-1-sulfonic acid, 4-methylbenzenesulfonic acid, benzenesulfonic acid, camphor-10-sulfonic acid, (+)-camphor-10-sulfonic acid, naphthalene 1,5-disulfonic acid, naphthalene 1-sulfonic acid, naphthalene 2-sulfonic acid, N-undecylbenzenesulfonic acid, 2-hydroxyethanesulfonic acid, p-chlorobenzenesulfonic acid, laurylsulfuric acid, dodecylsulfuric acid, aconitic acid, cinnamic acid, sorbic acid, glucoheptonic acid, muconic acid, galactaric acid (mucic acid), phenoxyacetic acid, phenylacetic acid, 3-phenylpropionic acid, benzoic acid, 4-hydroxybenzoic acid, o-(4-hydroxybenzoyl)benzoic acid, 2,4-dihydroxybenzoic acid, salicylic acid, 4-amino salicylic acid, 2,4,6-trimethylbenzoic acid, 2-aminobenzoic acid, 3-aminobenzoic acid, 4-aminobenzoic acid, 4-acetamido benzoic acid, 2-methoxybenzoic acid, 3-methoxybenzoic acid, anisic acid, N-benzoylanthranilic acid, hydroxynaphthoic acid, naphthoic acid, 1-hydroxy-2-naphthoic acid, 2-hydroxy-1-naphthalenic acid, vanillic acid, gluconic acid, ascorbic acid, L-(+)-ascorbic acid, geranic acid, pyruvic acid, alpha-ketobutyric acid, levulinic acid, 3-hydroxy-2-oxopropionic acid, 3-methyl-2-oxobutanoic acid, 3-methyl-2-oxopentanoic acid, 4-methyl-2-oxopentanoic acid, 4-(methylthio)-2-oxobutanoic acid, 2-oxopentanedioic acid, 2-oxo-3-phenylpropionic acid, 2-oxo-glutaric acid, embonic acid (pamoic acid), camphoric acid, cyclamic acid, acesulfamic acid, cyclohexaneacetic acid, cyclohexanecarboxylic acid, cis-2-heptylcyclopropane carboxylic acid, trans-2-heptylcyclopropane carboxylic acid, cyclopentanepropionic acid, 4-methylbicyclo[2.2.2]oct-2-ene-1-carboxylic acid, gentisic acid, orotic acid, 5-oxo-proline, dehydroacetic acid, 4,4'-methylenebis(3-hydroxy-2-ene-1-carboxylic acid), pyroglutamic acid, lysinic acid, L-lysinic acid, L-asparaginic acid, L-glutamic acid, acetyl glycine, alginic acid, 1-hydroxyethylidene-1,1-diphosphonic acid, glycerophosphoric acid, lactobionic acid, gluceptic acid, amino tri(methylene phosphonic acid), or (b2) at least one acid selected from the group consisting of hydrogen bromide, sulfuric acid, malic acid, formic acid, tartaric acid, nicotinic acid, acetic acid, succinic acid, fumaric acid, maleic acid, hippuric acid, methanesulfonic acid, citric acid, lactic acid, mandelic acid, malonic acid, oxalic acid, glutaminic acid, glutamic acid, aminobenzoic acid, α-lipoic acid, aspartic acid, asparaginic acid, saccharin, acetylsalicylic acid, [2-(2,6-dichlorophenylamino) phenyl]acetic acid (Diclofenac), dipyrone[(1,5-dimethyl-3-oxo-2-phenyl-2,3-dihydro-1H-pyrazol-4-yl) methylamino]-methanesulfonic acid (Metamizol), 2-(3'-fluorobiphenyl-4-yl)propionic acid (Flurbiprofen), 2-(3-benzoylphenyl)propionic acid (Ketoprofen), (+)-(S)-2-(6-methoxynaphthalen-2-yl)propionic acid (Naproxen) and 2-(4-isobutylphenyl)propionic acid (Ibuprofen).

Preferably the present invention relates to a salt or cocrystal of (a) 3-(3-dimethylamino-1-ethyl-2-methyl-propyl)-phenol, and (b1) at least one acid selected from the group consisting of hydrogen fluoride, hydrogen iodide, boric acid, nitric acid, carbonic acid, phosphoric acid, peracetic acid, periodic acid, sulfamic acid, sulfurous acid, thioacetic acid, thiodipropionic acid, trifluoromethane sulfonic acid, trimethylacetic acid, tertiary butylacetic acid, 2,2-dichloro-acetic acid, thiocyanic acid, isethionic acid, acetylaminoacetic acid, propionic acid, 2-mercaptopropionic acid, butyric acid, isobutyric acid, valeric acid, 2-methylvaleric acid, isovaleric acid, 2-methylbutyric acid, hexanoic acid (caproic acid), 2-ethylbutyric acid, 3-methylpentanoic acid, 4-methylpentanoic acid, heptanoic acid, (E)-2-heptenoic acid, 2-methylhexanoic acid, 5-methylhexanoic acid, octanoic acid (caprylic acid), 2-methylheptanoic acid, 4-methyloctanoic acid, nonanoic acid, decanoic acid (capric acid), 4-methylnonanoic acid, undecanoic acid, 4-ethyloctanoic acid, lauric acid, myristic acid, palmitic acid, octadecanoic acid (stearic acid), (E)-2-butenoic acid, trans-2-methyl-2-butenoic acid, 3-methylcrotonic acid, 2-pentenoic acid, 4-pentenoic acid, trans-2-hexenoic acid, 3-hexenoic acid, 2-methyl-2-pentenoic acid, 2-methyl-3-pentenoic acid, 2-methyl-4-pentenoic acid, 4-methylpent-2-enoic acid, 2,4-dimethyl-2-pentenoic acid, (E)-2-octenoic acid, (E)-2-nonenoic acid, 4-decenoic acid, 5-decenoic acid, 6-decenoic acid, 9-decenoic acid, (E)-2-decenoic acid, 3,7-dimethyl-6-octenoic acid, 10-undecenoic acid, oleic acid, L-(+)-tartaric acid, L-(+)-lactic acid, (S)-(+)-mandelic acid, glutaric acid, adipic acid, sebacic acid, monomethyl sebacic acid, glycolic acid, 2-hydroxysuccinic acid, linoleic acid, ethanesulfonic acid, ethane-1,2-disulfonic acid, hexane-1-sulfonic acid, 4-methylbenzenesulfonic acid, benzenesulfonic acid, naphthalene 1,5-disulfonic acid, naphthalene 1-sulfonic acid, naphthalene 2-sulfonic acid, N-undecylbenzenesulfonic acid, 2-hydroxyethanesulfonic acid, p-chlorobenzenesulfonic acid, laurylsulfuric acid, dodecylsulfuric acid, aconitic acid, cinnamic acid, sorbic acid, glucoheptonic acid, muconic acid, galactaric acid (mucic acid), phenoxyacetic acid, phenylacetic acid, 3-phenylpropionic acid, benzoic acid, 4-hydroxybenzoic acid, o-(4-hydroxybenzoyl)benzoic acid, 2,4-dihydroxybenzoic acid, 4-amino salicylic acid, 2,4,6-trimethylbenzoic acid, 2-aminobenzoic acid, 3-aminobenzoic acid, 4-aminobenzoic acid, 4-acetamido benzoic acid, 2-methoxybenzoic acid, 3-methoxybenzoic acid, anisic acid, N-benzoylanthranilic acid, hydroxynaphthoic acid, naphthoic acid, 1-hydroxy-2-naphthoic acid, 2-hydroxy-1-naphthalenic acid, vanillic acid, gluconic acid, ascorbic acid, L-(+)-ascorbic acid, geranic acid, pyruvic acid, alpha-ketobutyric acid, levulinic acid, 3-hydroxy-2-oxopropionic acid, 3-methyl-2-oxobutanoic acid, 3-methyl-2-oxopentanoic acid, 4-methyl-2-oxopentanoic acid, 4-(methylthio)-2-oxobutanoic acid, 2-oxopentanedioic acid, 2-oxo-3-phenylpropionic acid, 2-oxo-glutaric acid, embonic acid (pamoic acid), camphoric acid, cyclamic acid, acesulfamic acid, cyclohexaneacetic acid, cyclohexanecarboxylic acid, cis-2-heptylcyclopropane carboxylic acid, trans-2-heptylcyclopropane carboxylic acid, cyclopentanepropionic acid, 4-methylbicyclo[2.2.2]oct-2-ene-1-carboxylic acid, gentisic acid, orotic acid, 5-oxo-proline, dehydroacetic acid, 4,4'-methylenebis(3-hydroxy-2-ene-1-carboxylic acid), pyroglutamic acid, lysinic acid, L-lysinic acid, L-asparaginic acid, L-glutamic acid, acetyl glycine, alginic acid, 1-hydroxyethylidene-1,1-diphosphonic acid, glycerophosphoric acid, lactobionic acid, gluceptic acid, amino tri(methylene phosphonic acid), or (b2) at least one acid selected from the group consisting of hydrogen bromide, sulfuric acid, formic acid, tartaric acid, nicotinic acid, acetic acid, succinic acid, fumaric acid, hippuric acid, methanesulfonic acid, citric acid, lactic acid, mandelic acid, malonic acid, oxalic acid, glutaminic acid, glutamic acid, aminobenzoic acid, α-lipoic acid, aspartic acid, asparaginic acid, saccharin, acetylsalicylic acid, [2-(2,6-dichlorophenylamino)phenyl]acetic acid (Diclofenac), dipyrone[(1,5-dimethyl-3-oxo-2-phenyl-2,3-dihydro-1H-pyrazol-4-yl)methylamino]-methanesulfonic acid (Metamizol), 2-(3'-fluorobiphenyl-4-yl)propionic acid (Flurbiprofen), 2-(3-benzoylphenyl)propionic acid (Ketoprofen), (+)-(S)-2-(6-methoxynaphthalen-2-yl)propionic acid (Naproxen) and 2-(4-isobutylphenyl)propionic acid (Ibuprofen).

In one embodiment the present invention relates to a salt or cocrystal of (a) 3-(3-dimethylamino-1-ethyl-2-methyl-propyl)-phenol, and (b1) at least one acid selected from the group consisting of embonic acid, (2S,3S)-dibenzoyltartaric acid, dibenzoyltartaric acid, sebacic acid, 1-hydroxy-2-naphthoic acid, phosphoric acid, L-(+)-tartaric acid, lysinic acid, L-lysinic acid, D-(+)-malic acid, 4-methylbenzenesulfonic acid, ethanesulfonic acid, benzoic acid, cinnamic acid, L-(+)-lactic acid, S-(+)-mandelic acid, (+)-camphor-10-sulfonic acid, gluconic acid, L-(+)-ascorbic acid, ascorbic acid, palmitic acid, naphthalene-1,5-disulfonic acid, hexanoic acid, oleic acid, stearic acid, gentisic acid, octanoic acid, decanoic acid, nitric acid, orotic acid, mucic acid, alginic acid and acesulfamic acid, or (b2) at least one acid selected from the group consisting of nicotinic acid, hydrogen bromide, sulfuric acid, acetic acid, oxalic acid, succinic acid, fumaric acid, maleic acid, hippuric acid, lactic acid, mandelic acid, malonic acid, malic acid, tartaric acid, methanesulfonic acid, citric acid, lactic acid, mandelic acid and saccharin.

In yet another embodiment the present invention relates to a salt or cocrystal of (a) 3-(3-dimethylamino-1-ethyl-2-methyl-propyl)-phenol, and (b1) at least one acid selected from the group consisting of embonic acid, sebacic acid, 1-hydroxy-2-naphthoic acid, phosphoric acid, L-(+)-tartaric acid, lysinic acid, L-lysinic acid, 4-methylbenzenesulfonic acid, ethanesulfonic acid, benzoic acid, cinnamic acid, L-(+)-lactic acid, S-(+)-mandelic acid, gluconic acid, L-(+)-ascorbic acid, ascorbic acid, palmitic acid, naphthalene-1,5-disulfonic acid, hexanoic acid, oleic acid, stearic acid, gentisic acid, octanoic acid, decanoic acid, nitric acid, orotic acid, mucic acid, alginic acid and acesulfamic acid, or (b2) at least one acid selected from the group consisting of nicotinic acid, hydrogen bromide, sulfuric acid, acetic acid, oxalic acid, succinic acid, fumaric acid, hippuric acid, lactic acid, mandelic acid, malonic acid, tartaric acid, methanesulfonic acid, citric acid, lactic acid, mandelic acid and saccharin.

In a preferred embodiment of the present invention component (b1) is at least one acid selected from the group consisting of (2S,3S)-dibenzoyltartaric acid, dibenzoyltartaric acid, sebacic acid, 1-hydroxy-2-naphthoic acid, nitric acid and embonic acid.

In another preferred embodiment of the present invention component (b1) is at least one acid selected from the group consisting of (2S,3S)-dibenzoyltartaric acid, sebacic acid, 1-hydroxy-2-naphthoic acid and embonic acid.

In still another preferred embodiment of the present invention component (b1) is at least one acid selected from the group consisting of sebacic acid, 1-hydroxy-2-naphthoic acid and embonic acid.

In yet another preferred embodiment of the present invention component (b2) is at least one acid selected from the group consisting of nicotinic acid, hydrogen bromide, fumaric acid, malonic acid and sulfuric acid.

In still another preferred embodiment of the present invention component (b2) is nicotinic acid.

Preferably, the 3-(3-dimethylamino-1-ethyl-2-methyl-propyl)-phenol compound, i.e. component (a) of the inventive salt or cocrystal, is a compound according to formulae (I-a), (I-b), (I-c) or (I-d) or any mixture in any mixing ratio thereof:

(I-a)

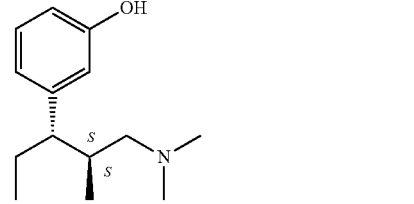

(I-b)

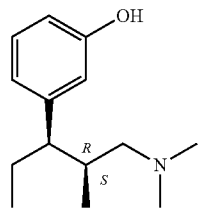

(I-c)

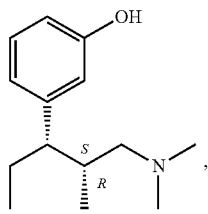

(I-d)

namely a compound selected from the group consisting of
(1R,2R)-3-(3-dimethylamino-1-ethyl-2-methyl-propyl)-phenol (I-a),
(1S,2S)-3-(3-dimethylamino-1-ethyl-2-methyl-propyl)-phenol (I-b),
(1R,2S)-3-(3-dimethylamino-1-ethyl-2-methyl-propyl)-phenol (I-c)
(1S,2R)-3-(3-dimethylamino-1-ethyl-2-methyl-propyl)-phenol (I-d),
and any mixture thereof.

Particularly preferred 3-(3-dimethylamino-1-ethyl-2-methyl-propyl)-phenol compounds are compounds according to formulae (I-a) or (I-b) or any mixture in any mixing ratio thereof. The most preferred compound is a compound according to formula (I-a), i.e. is (1R,2R)-3-(3-dimethylamino-1-ethyl-2-methyl-propyl)-phenol (I-a). As stated above the compound according to formula (I-a) is also known as tapentadol.

In one of its particularly preferred embodiments the present invention relates to a salt or cocrystal of
(a) (1R,2R)-3-(3-dimethylamino-1-ethyl-2-methyl-propyl)-phenol, and
(b1) at least one acid selected from the group consisting of embonic acid, (2S,3S)-dibenzoyltartaric acid, dibenzoyltartaric acid, sebacic acid, 1-hydroxy-2-naphthoic acid, phosphoric acid, L-(+)-tartaric acid, lysinic acid, L-lysinic acid, D-(+)-malic acid, 4-methylbenzenesulfonic acid, ethanesulfonic acid, benzoic acid, cinnamic acid, L-(+)-lactic acid, S-(+)-mandelic acid, (+)-camphor-10-sulfonic acid, gluconic acid, L-(+)-ascorbic acid, ascorbic acid, palmitic acid, naphthalene-1,5-disulfonic acid, hexanoic acid, oleic acid, stearic acid, gentisic acid, octanoic acid, decanoic acid, nitric acid, orotic acid, mucic acid, alginic acid and acesulfamic acid, or
(b2) at least one acid selected from the group consisting of nicotinic acid, hydrogen bromide, sulfuric acid, acetic acid, oxalic acid, succinic acid, fumaric acid, maleic acid, hippuric acid, lactic acid, mandelic acid, malonic acid, malic acid, tartaric acid, methanesulfonic acid, citric acid, lactic acid, mandelic acid and saccharin.

In another one of its particularly preferred embodiments the present invention relates to a salt or cocrystal of
(a) (1R,2R)-3-(3-dimethylamino-1-ethyl-2-methyl-propyl)-phenol, and
(b1) at least one acid selected from the group consisting of embonic acid, sebacic acid, 1-hydroxy-2-naphthoic acid, phosphoric acid, L-(+)-tartaric acid, lysinic acid, L-lysinic acid, 4-methylbenzenesulfonic acid, ethanesulfonic acid, benzoic acid, cinnamic acid, L-(+)-lactic acid, S-(+)-mandelic acid, gluconic acid, L-(+)-ascorbic acid, ascorbic acid, palmitic acid, naphthalene-1,5-disulfonic acid, hexanoic acid, oleic acid, stearic acid, gentisic acid, octanoic acid, decanoic acid, nitric acid, orotic acid, mucic acid, alginic acid and acesulfamic acid, or
(b2) at least one acid selected from the group consisting of nicotinic acid, hydrogen bromide, sulfuric acid, acetic acid, oxalic acid, succinic acid, fumaric acid, hippuric acid, lactic acid, mandelic acid, malonic acid, tartaric acid, methanesulfonic acid, citric acid, lactic acid, mandelic acid and saccharin.

Also particularly preferred is a salt or cocrystal of (a) (1R,2R)-3-(3-dimethylamino-1-ethyl-2-methyl-propyl)-phenol and component (b1) selected from the group consisting of (2S,3S)-dibenzoyltartaric acid, dibenzoyltartaric acid, sebacic acid, 1-hydroxy-2-naphthoic acid, nitric acid and embonic acid.

Furthermore, particularly preferred is a salt or cocrystal of (a) (1R,2R)-3-(3-dimethylamino-1-ethyl-2-methyl-propyl)-phenol and component (b1) selected from the group consisting of (2S,3S)-dibenzoyltartaric acid, sebacic acid, 1-hydroxy-2-naphthoic acid and embonic acid.

In addition, particularly preferred is a salt or cocrystal of (a) (1R,2R)-3-(3-dimethylamino-1-ethyl-2-methyl-propyl)-phenol and component (b1) selected from the group consisting of sebacic acid, 1-hydroxy-2-naphthoic acid and embonic acid.

Also particularly preferred is a salt or cocrystal of (a) (1R,2R)-3-(3-dimethylamino-1-ethyl-2-methyl-propyl)-phenol and component (b2) selected from the group consisting of nicotinic acid, hydrogen bromide, fumaric acid, malonic acid and sulfuric acid.

In one of its most preferred embodiments, the present invention relates to a salt or cocrystal of (a) (1R,2R)-3-(3-dimethylamino-1-ethyl-2-methyl-propyl)-phenol and (b1) (2S,3S)-dibenzoyltartaric acid.

In another one of its most preferred embodiments, the present invention relates to a salt or cocrystal of (a) (1R,2R)-3-(3-dimethylamino-1-ethyl-2-methyl-propyl)-phenol and (b1) sebacic acid.

In still another one of its most preferred embodiments, the present invention relates to a salt or cocrystal of (a) (1R,2R)-3-(3-dimethylamino-1-ethyl-2-methyl-propyl)-phenol and (B1) 1-hydroxy-2-naphthoic acid.

In yet still another one of its most preferred embodiments, the present invention relates to a salt or cocrystal of (a) (1R, 2R)-3-(3-dimethylamino-1-ethyl-2-methyl-propyl)-phenol and (b1) embonic acid.

In yet still another one of its most preferred embodiments, the present invention relates to a salt or cocrystal of (a) (1R, 2R)-3-(3-dimethylamino-1-ethyl-2-methyl-propyl)-phenol and (b1) nitric acid.

In one of its most preferred embodiments, the present invention relates to a salt or cocrystal of (a) (1R,2R)-3-(3-dimethylamino-1-ethyl-2-methyl-propyl)-phenol and (b2) nicotinic acid.

In another one of its most preferred embodiments, the present invention relates to a salt or cocrystal of (a) (1R,2R)-3-(3-dimethylamino-1-ethyl-2-methyl-propyl)-phenol and (b2) hydrogen bromide acid.

In still another one of its most preferred embodiments, the present invention relates to a salt or cocrystal of (a) (1R,2R)-3-(3-dimethylamino-1-ethyl-2-methyl-propyl)-phenol and (b2) fumaric acid.

In yet still another one of its most preferred embodiments, the present invention relates to a salt or cocrystal of (a) (1R,2R)-3-(3-dimethylamino-1-ethyl-2-methyl-propyl)-phenol and (b2) malonic acid.

Furthermore, in yet another one of its most preferred embodiments, the present invention relates to a salt or cocrystal of (a) (1R,2R)-3-(3-dimethylamino-1-ethyl-2-methyl-propyl)-phenol and (b2) sulfuric acid.

The inventive salts or cocrystals may comprise mixtures of one or more acids according to component (b1) or mixtures of one or more acids according to component (b2) or mixtures of one or more acids according to component (b1) and one or more acids according to component (b2).

The inventive salt or cocrystal formed from component (a) and component (b2) is preferably present in crystalline or amorphous form, more preferably the inventive salt or cocrystal formed from component (a) and component (b2) is crystalline.

In one of its embodiments the inventive salt or cocrystal formed from component (a) and component (b1) is present in crystalline form.

In another one of its embodiments the inventive salt or cocrystal formed from component (a) and component (b1) is present in amorphous form.

The salts or cocrystals according to the present invention may also be present in form of mixture with known salts of tapentadol such as tapentadol hydrochloride. Moreover, such known tapentadol compounds may also be present to form a co-crystal.

In a preferred embodiment the inventive salts or cocrystals of 3-(3-dimethylamino-1-ethyl-2-methyl-propyl)-phenol are physiologically acceptable salts or cocrystals, e.g. physiologically acceptable acid addition salts or cocrystals. For the purpose of the specification, the term "physiologically acceptable salt" or "physiologically acceptable cocrystal" refers to a salt or cocrystal of a 3-(3-dimethylamino-1-ethyl-2-methyl-propyl)-phenol compound and at least acid (b1) or (b2), that are physiologically acceptable if administered to a mammal, preferably a human.

The inventively claimed salt or cocrystal may be in anhydrous and/or essentially solvent-free form, or be in hydrate and/or solvate form.

The acid according to component (b1) or (b2) employed for the formation of the inventive salt or cocrystal may be in each case optionally be employed in the form of a solvate, in particular a hydrate.

The salts or cocrystals according to the present invention may contain the components (a) and (b1) or (b2) in different ratios as is clear to those skilled in the art.

In a preferred embodiment of the present invention the salt or cocrystal may comprise component (a) and component (b1) or (b2), respectively, within a ratio from 1:0.4 to 1:2.1, more preferably within the range of from 1:0.4 to 1:1.1.

Some of the inventively claimed salts or cocrystals may be present as so-called hemi-salts or hemi-cocrystals, i.e. the components (a) and (b1) or (b2) are essentially present in a 2:1-stochiometry. Such hemi salts or hemi-cocrystals are well known to those skilled in the art. Examples of such inventive hemi-salts or hemi-cocrystals of tapentadol are those with (2S,3S)-dibenzoyltartaric acid, fumaric acid and embonic acid.

Thus, in another embodiment the present invention relates to a hemi-(2S,3S)-dibenzoyl-tartrate of tapentadol or a corresponding hemi-cocrystal.

In still another embodiment the present invention relates to a hemi-fumarate of tapentadol or a corresponding hemi-cocrystal.

In yet another embodiment the present invention relates to hemi-embonate of tapentadol or a corresponding hemi-cocrystal.

In general, the solubility of the inventive salt or cocrystal may not only be influenced in a targeted manner by the choice of the acid (b1) or (b2), but further may be additionally influenced by the solid state of said salt or cocrystal, e.g. whether the salt or cocrystal is present in a crystalline form such as the inventive salt or cocrystal formed from component (a) and component (b2), or whether the salt or cocrystal is present in an amorphous form.

Solid forms of the inventive salts or cocrystals may have a plurality of different internal structures and physicochemical properties (crystal polymorphism or polyamorphism) depending on the reaction conditions and/or crystallization/co-crystallization conditions employed for the synthesis of the salt or cocrystal. Therefore, crystalline forms of the inventive salt or cocrystal encompass such individual crystals and/or mixtures thereof in any ratio as a crystalline solid. Further, solid forms of the inventive salt or cocrystal may be mixtures of a crystalline and/or amorphous form of the salt or cocrystal, i.e. a crystalline and/or an amorphous form of the salt or cocrystal. Preferably, however, solid forms of the inventive salt or cocrystal are crystalline do not comprise an amorphous form.

A person skilled in the art is aware of the techniques which can be employed to obtain and identify the crystalline and/or amorphous forms of the inventive salts or cocrystals. In general, crystals and co-crystals are solids having an internal structure which is three-dimensionally formed by regular repetition of constituent atoms or groups of constituent atoms. In contrast, an amorphous solid does not have such a regular internal structure. A person skilled in the art is aware that e.g. powder X-ray diffraction giving specific X-ray powder diffraction patterns ("XRPD") or differential scanning calorimetry are suitable methods which can be employed in order to find out whether a solid is a crystalline or amorphous or any mixture thereof. For example, in X-ray powder diffraction of a solid using X-rays, the solid is determined to be a crystalline or partly crystalline when at least a specific peak is observed in its X-ray powder diffraction pattern ("XRPD"), and the solid is determined to be amorphous when no specific peak is observed. X-ray single crystal diffraction technique may be used for determination whether a compound forms a salt or a cocrystal or any mixture thereof.

It has been found that under suitable conditions some of the inventive salts or cocrystals can be obtained in the form of different polymorphs.

These crystalline forms make it possible to obtain the respective salts or cocrystals with high yields and high purity. These forms are further distinguished in that they are very easy to handle and allow an exact metering of the active ingredient.

Moreover, different polymorphs of said pharmaceutical active ingredient have fundamentally different properties, which may provide further advantages.

On the one hand, the advantages may be based on a particular physical property of a particular modification, for example, in relation to the handling or storage thereof, for example thermodynamic stability; crystal morphology, in particular structure, size, colour; density; bulk density; hardness; deformability; calorimetric characteristics, in particular melting point; solubility properties, in particular intrinsic rate of dissolution and equilibrium solubility; hygroscopicity; relative moisture profile; adhesion, etc.

On the other hand, the crystalline modification may also have improved chemical properties. For example, better thermodynamic stability can lead to improved chemical stability and longer storage life for chemical compounds, in particular compared to metastable and/or amorphous forms.

It has been found that the salt or cocrystal of embonic acid and (1R,2R)-3-(3-dimethylamino-1-ethyl-2-methyl-propyl)-phenol can be obtained in the form of the different polymorphs A and B.

Thus, a further subject-matter of the present invention relates to a crystalline modification A of the salt or cocrystal of embonic acid and (1R,2R)-3-(3-dimethylamino-1-ethyl-2-methyl-propyl)-phenol.

This crystalline modification A of the salt or cocrystal of embonic acid and (1R,2R)-3-(3-dimethylamino-1-ethyl-2-methyl-propyl)-phenol according to the invention has at least one or more X-ray diffraction peaks selected from the group consisting of 7.94±0.20 (2θ), 10.40±0.20 (2θ), 14.25±0.20 (2θ), 17.18±0.20 (2θ) and 18.77±0.20 (2θ).

Preferably, the crystalline modification A of the salt or cocrystal of embonic acid and (1R,2R)-3-(3-dimethylamino-1-ethyl-2-methyl-propyl)-phenol according to the invention may additionally have at least one X-ray diffraction peak selected from the group consisting of 6.49±0.20 (2θ), 7.27±0.20 (2θ), 12.89±0.20 (2θ), 27.34±0.20 (2θ) and 28.08±0.20 (2θ).

The crystalline modification A of the salt or cocrystal of embonic acid and (1R,2R)-3-(3-dimethylamino-1-ethyl-2-methyl-propyl)-phenol according to the invention may further be characterised in that as well as one or more X-ray diffraction peaks selected from the group consisting of 7.94±0.20 (2θ), 10.40±0.20 (2θ), 14.25±0.20 (2θ), 17.18±0.20 (2θ) and 18.77±0.20 (2θ) and optionally one or more X-ray diffraction peaks selected from the group consisting of 6.49±0.20 (2θ), 7.27±0.20 (2θ), 12.89±0.20 (2θ), 27.34±0.20 (2θ) and 28.08±0.20 (2θ) it additionally has at least one X-ray diffraction peak selected from the group consisting of 5.32±0.20 (2θ), 9.47±0.20 (2θ), 10.75±0.20 (2θ), 11.16±0.20 (2θ), 13.54±0.20 (2θ), 15.64±0.20 (2θ), 19.34±0.20 (2θ), 20.77±0.20 (2θ), 22.03±0.20 (2θ), 23.17±0.20 (2θ), 23.49±0.20 (2θ), 25.08±0.20 (2θ), 26.30±0.20 (2θ), 29.39±0.20 (2θ), 29.93±0.20 (2θ), 30.41±0.20 (2θ), 32.40±0.20 (2θ), 33.41±0.20 (2θ), 33.95±0.20 (2θ), 34.96±0.20 (2θ), 35.54±0.20 (2θ), 36.65±0.20 (2θ) and 37.42±0.20 (2θ).

The X-ray powder diffractogramm of the crystalline modification A of the salt or cocrystal of embonic acid and (1R,2R)-3-(3-dimethylamino-1-ethyl-2-methyl-propyl)-phenol is shown in FIG. 7.

Another subject-matter of the present invention relates to a crystalline modification B of the salt or cocrystal of embonic acid and (1R,2R)-3-(3-dimethylamino-1-ethyl-2-methyl-propyl)-phenol.

This crystalline modification B of the salt or cocrystal of embonic acid and (1R,2R)-3-(3-dimethylamino-1-ethyl-2-methyl-propyl)-phenol according to the invention has at least one or more X-ray diffraction peaks selected from the group consisting of 6.00±0.20 (2θ), 11.96±0.20 (2θ) and 17.61±0.20 (2θ).

Preferably, the crystalline modification B of the salt or cocrystal of embonic acid and (1R,2R)-3-(3-dimethylamino-1-ethyl-2-methyl-propyl)-phenol according to the invention may additionally have at least one X-ray diffraction peak selected from the group consisting of 14.86±0.20 (2θ), 16.22±0.20 (2θ), 20.29±0.20 (2θ) and 24.18±0.20 (2θ).

The crystalline modification B of the salt or cocrystal of embonic acid and (1R,2R)-3-(3-dimethylamino-1-ethyl-2-methyl-propyl)-phenol according to the invention may further be characterised in that as well as one or more X-ray diffraction peaks selected from the group consisting of 6.00±0.20 (2θ), 11.96±0.20 (2θ) and 17.61±0.20 (2θ) and optionally one or more X-ray diffraction peaks selected from the group consisting of 14.86±0.20 (2θ), 16.22±0.20 (2θ), 20.29±0.20 (2θ) and 24.18±0.20 (2θ) it additionally has at least one X-ray diffraction peak selected from the group consisting of 9.40±0.20 (2θ), 11.04±0.20 (2θ), 13.70±0.20 (2θ), 15.57±0.20 (2θ), 17.61±0.20 (2θ), 19.23±0.20 (2θ), 20.51±0.20 (2θ), 21.91±0.20 (2θ), 22.97±0.20 (2θ), 23.34±0.20 (2θ), 24.82±0.20 (2θ), 26.13±0.20 (2θ) and 29.78±0.20 (2θ).

The X-ray powder diffractogramm of the crystalline modification B of the salt or cocrystal of embonic acid and (1R,2R)-3-(3-dimethylamino-1-ethyl-2-methyl-propyl)-phenol is shown in FIG. 8.

Moreover, it has been found that the salt or cocrystal of nicotinic acid and (1R,2R)-3-(3-dimethylamino-1-ethyl-2-methyl-propyl)-phenol can be obtained in the form of the different polymorphs $A^1$ and $B^1$.

Thus, a further subject-matter of the present invention relates to a crystalline modification $A^1$ of the salt or cocrystal of nicotinic acid and (1R,2R)-3-(3-dimethylamino-1-ethyl-2-methyl-propyl)-phenol.

This crystalline modification $A^1$ of the salt or cocrystal of nicotinic acid and (1R,2R)-3-(3-dimethylamino-1-ethyl-2-methyl-propyl)-phenol according to the invention has at least one or more X-ray diffraction peaks selected from the group consisting of 12.60±0.20 (2θ), 15.61±0.20 (2θ) and 22.82±0.20 (2θ).

Preferably, the crystalline modification $A^1$ of the salt or cocrystal of nicotinic acid and (1R,2R)-3-(3-dimethylamino-1-ethyl-2-methyl-propyl)-phenol according to the invention may additionally have at least one X-ray diffraction peak selected from the group consisting of 13.70±0.20 (2θ) and 18.10±0.20 (2θ).

The crystalline modification $A^1$ according to the invention may further be characterised in that as well as one or more X-ray diffraction peaks selected from the group consisting of 12.60±0.20 (2θ), 15.61±0.20 (2θ) and 22.82±0.20 (2θ) and optionally one or more X-ray diffraction peaks selected from the group consisting of 13.70±0.20 (2θ) and 18.10±0.20 (2θ), it additionally has at least one X-ray diffraction peak selected from the group consisting 16.57±0.20 (2θ), 17.68±0.20 (2θ), 19.13±0.20 (2θ), 19.90±0.20 (2θ), 20.09±0.20 (2θ), 20.95±0.20 (2θ), 24.63±0.20 (2θ), 24.77±0.20 (2θ), 25.49±0.20 (2θ) and 25.64±0.20 (2θ).

The crystalline modification $A^1$ according to the invention may further be characterised in that as well as one or more X-ray diffraction peaks selected from the group consisting of 12.60±0.20 (2θ), 15.61±0.20 (2θ) and 22.82±0.20 (2θ) and optionally one or more X-ray diffraction peaks selected from the group consisting of 13.70±0.20 (2θ) and 18.10±0.20 (2θ), and optionally one or more X-ray diffraction peaks selected from the group consisting 16.57±0.20 (2θ), 17.68±0.20 (2θ), 19.13±0.20 (2θ), 19.90±0.20 (2θ), 20.09±0.20 (2θ), 20.95±0.20 (2θ), 24.63±0.20 (2θ), 24.77±0.20 (2θ), 25.49±0.20 (2θ) and 25.64±0.20 (2θ) it additionally has at least one X-ray diffraction peak selected from the group consisting 9.57±0.20 (2θ), 10.93±0.20 (2θ), 17.08±0.20 (2θ), 18.30±0.20 (2θ), 20.72±0.20 (2θ), 21.97±0.20 (2θ), 26.77±0.20 (2θ), 27.26±0.20 (2θ), 27.64±0.20 (2θ), 28.18±0.20 (2θ), 28.58±0.20 (2θ), 29.36±0.20 (2θ), 29.47±0.20 (2θ), 29.79±0.20 (2θ), 30.20±0.20 (2θ), 31.11±0.20 (2θ), 31.52±0.20 (2θ), 32.05±0.20 (2θ), 32.63±0.20 (2θ), 33.21±0.20 (2θ), 34.93±0.20 (2θ), 37.28±0.20 (2θ), 38.40±0.20 (2θ), 39.00±0.20 (2θ) and 39.45±0.20 (2θ).

The X-ray powder diffractogramm of the crystalline modification A¹ of the salt or cocrystal of nicotinic acid and (1R,2R)-3-(3-dimethylamino-1-ethyl-2-methyl-propyl)-phenol is shown in FIG. 5.

Another subject-matter of the present invention relates to a crystalline modification B¹ of the salt or cocrystal of nicotinic acid and (1R,2R)-3-(3-dimethylamino-1-ethyl-2-methyl-propyl)-phenol.

This crystalline modification B¹ of the salt or cocrystal of nicotinic acid and (1R,2R)-3-(3-dimethylamino-1-ethyl-2-methyl-propyl)-phenol according to the invention has at least one or more X-ray diffraction peaks selected from the group consisting of 10.34±0.20 (2θ), 12.14±0.20 (2θ), 22.38±0.20 (2θ), 23.65±0.20 (2θ) and 26.11±0.20 (2θ).

Preferably, the crystalline modification B¹ of the salt or cocrystal of nicotinic acid and (1R,2R)-3-(3-dimethylamino-1-ethyl-2-methyl-propyl)-phenol according to the invention may additionally have at least one X-ray diffraction peak selected from the group consisting of 17.01±0.20 (2θ), 20.16±0.20 (2θ), 20.85±0.20 (2θ), 21.75±0.20 (2θ) and 25.49±0.20 (2θ). The crystalline modification B¹ according to the invention may further be characterised in that as well as one or more X-ray diffraction peaks selected from the group consisting of 10.34±0.20 (2θ), 12.14±0.20 (2θ), 22.38±0.20 (2θ), 23.65±0.20 (2θ) and 26.11±0.20 (2θ) and optionally one or more X-ray diffraction peaks selected from the group consisting of 17.01±0.20 (2θ), 20.16±0.20 (2θ), 20.85±0.20 (2θ), 21.75±0.20 (2θ) and 25.49±0.20 (2θ), it additionally has at least one X-ray diffraction peak selected from the group consisting 9.59±0.20 (2θ), 11.30±0.20 (2θ), 16.20±0.20 (2θ), 17.57±0.20 (2θ), 18.58±0.20 (2θ), 19.28±0.20 (2θ), 22.24±0.20 (2θ), 24.48±0.20 (2θ), 24.99±0.20 (2θ), 26.60±0.20 (2θ), 27.39±0.20 (2θ), 28.02±0.20 (2θ), 28.15±0.20 (2θ), 28.84±0.20 (2θ), 29.20±0.20 (2θ), 29.44±0.20 (2θ), 29.91±0.20 (2θ), 30.49±0.20 (2θ), 30.94±0.20 (2θ), 31.48±0.20 (2θ), 32.56±0.20 (2θ), 32.94±0.20 (2θ), 33.62±0.20 (2θ), 34.14±0.20 (2θ), 36.01±0.20 (2θ), 36.24±0.20 (2θ), 37.30±0.20 (2θ), 37.84±0.20 (2θ), 38.68±0.20 (2θ), 38.90±0.20 (2θ) and 39.42±0.20 (2θ).

The X-ray powder diffractogramm of the crystalline modification B¹ of the salt or cocrystal of nicotinic acid and (1R,2R)-3-(3-dimethylamino-1-ethyl-2-methyl-propyl)-phenol is shown in FIG. 6.

Another subject-matter of the present invention relates to a crystalline modification of the salt or cocrystal of hydrobromic acid and (1R,2R)-3-(3-dimethylamino-1-ethyl-2-methyl-propyl)-phenol.

This crystalline modification of the salt or cocrystal of hydrobromic acid and (1R,2R)-3-(3-dimethylamino-1-ethyl-2-methyl-propyl)-phenol according to the invention has at least one or more X-ray diffraction peaks selected from the group consisting of 9.93±0.20 (2θ), 14.39±0.20 (2θ), 15.22±0.20 (2θ), 17.60±0.20 (2θ), 20.81±0.20 (2θ), 21.61±0.20 (2θ), 24.37±0.20 (2θ), 24.73±0.20 (2θ), 25.19±0.20 (2θ), 27.14±0.20 (2θ), 27.94±0.20 (2θ), 29.00±0.20 (2θ) and 30.75±0.20 (2θ).

Preferably, the crystalline modification of the salt or cocrystal of hydrobromic acid and (1R,2R)-3-(3-dimethylamino-1-ethyl-2-methyl-propyl)-phenol according to the invention may additionally have at least one X-ray diffraction peak selected from the group consisting of 16.60±0.20 (2θ), 19.48±0.20 (2θ), 19.95±0.20 (2θ), 21.26±0.20 (2θ), 25.52±0.20 (2θ), 25.69±0.20 (2θ), 26.05±0.20 (2θ), 29.44±0.20 (2θ), 29.67±0.20 (2θ), 30.13±0.20 (2θ), 32.25±0.20 (2θ), 33.02±0.20 (2θ), 33.48±0.20 (2θ), and 38.69±0.20 (2θ).

The crystalline modification of the salt or cocrystal of hydrobromic acid and (1R,2R)-3-(3-dimethylamino-1-ethyl-2-methyl-propyl)-phenol according to the invention may further be characterised in that as well as one or more X-ray diffraction peaks selected from the group consisting of 9.93±0.20 (2θ), 14.39±0.20 (2θ), 15.22±0.20 (2θ), 17.60±0.20 (2θ), 20.81±0.20 (2θ), 21.61±0.20 (2θ), 24.37±0.20 (2θ), 24.73±0.20 (2θ), 25.19±0.20 (2θ), 27.14±0.20 (2θ), 27.94±0.20 (2θ), 29.00±0.20 (2θ) and 30.75±0.20 (2θ) and optionally one or more X-ray diffraction peaks selected from the group consisting of 16.60±0.20 (2θ), 19.48±0.20 (2θ), 19.95±0.20 (2θ), 21.26±0.20 (2θ), 25.52±0.20 (2θ), 25.69±0.20 (2θ), 26.05±0.20 (2θ), 29.44±0.20 (2θ), 29.67±0.20 (2θ), 30.13±0.20 (2θ), 32.25±0.20 (2θ), 33.02±0.20 (2θ), 33.48±0.20 (2θ), and 38.69±0.20 (2θ) it additionally has at least one X-ray diffraction peak selected from the group consisting 8.73±0.20 (2θ), 12.29±0.20 (2θ), 13.38±0.20 (2θ), 15.94±0.20 (2θ), 23.58±0.20 (2θ), 26.54±10.20 (2θ), 31.71±0.20 (2θ), 32.77±0.20 (2θ), 33.75±0.20 (2θ), 35.42±0.20 (2θ), 35.94±0.20 (2θ), 36.45±0.20 (2θ), 36.79±0.20 (2θ), 37.52±0.20 (2θ), 38.28±0.20 (2θ), 38.94±0.20 (2θ), 39.21±0.20 (2θ) and 39.67±0.20 (2θ).

The X-ray powder diffractogramm of the crystalline modification of the salt or cocrystal of hydrobromic acid and (1R,2R)-3-(3-dimethylamino-1-ethyl-2-methyl-propyl)-phenol is shown in FIG. 1.

Another subject-matter of the present invention relates to a crystalline modification of the salt or cocrystal of malonic acid and (1R,2R)-3-(3-dimethylamino-1-ethyl-2-methyl-propyl)-phenol.

This crystalline modification of the salt or cocrystal of malonic acid and (1R,2R)-3-(3-dimethylamino-1-ethyl-2-methyl-propyl)-phenol according to the invention has at least one or more X-ray diffraction peaks selected from the group consisting of 8.75±0.20 (2θ), 11.85±0.20 (2θ), 13.74±0.20 (2θ), 16.78±0.20 (2θ), 18.09±0.20 (2θ), 19.17±0.20 (2θ), 16.65±0.20 (2θ), 20.45±0.20 (2θ), 21.66±0.20 (2θ), 24.80±0.20 (2θ) and 25.55±0.20 (2θ).

Preferably, the crystalline modification of the salt or cocrystal of malonic acid and (1R,2R)-3-(3-dimethylamino-1-ethyl-2-methyl-propyl)-phenol according to the invention may additionally have at least one X-ray diffraction peak selected from the group consisting of 5.43±0.20 (2θ), 14.38±0.20 (2θ), 16.09±0.20 (2θ), 16.39±0.20 (2θ), 17.21±0.20 (2θ), 18.43±0.20 (2θ), 18.69±0.20 (2θ), 21.02±0.20 (2θ), 23.77±0.20 (2θ), 24.07±0.20 (2θ), 25.31±0.20 (2θ), 26.14±0.20 (2θ), 26.73±0.20 (2θ), 27.49±0.20 (2θ), 28.16±0.20 (2θ), 30.05±0.20 (2θ), 30.45±0.20 (2θ), 31.21±0.20 (2θ), 31.51±0.20 (2θ), 35.37±0.20 (2θ) and 37.15±0.20 (2θ).

The crystalline modification of the salt or cocrystal of malonic acid and (1R,2R)-3-(3-dimethylamino-1-ethyl-2-methyl-propyl)-phenol according to the invention may further be characterised in that as well as one or more X-ray diffraction peaks selected from the group consisting of 8.75±0.20 (2θ), 11.85±0.20 (2θ), 13.74±0.20 (2θ), 16.78±0.20 (2θ), 18.09±0.20 (2θ), 19.17±0.20 (2θ), 16.65±0.20 (2θ), 20.45±0.20 (2θ), 21.66±0.20 (2θ), 24.80±0.20 (2θ) and 25.55±0.20 (2θ) and optionally one or more X-ray diffraction peaks selected from the group consisting of 5.43±0.20 (2θ), 14.38±0.20 (2θ), 16.09±0.20 (2θ), 16.39±0.20 (2θ), 17.21±0.20 (2θ), 18.43±0.20 (2θ), 18.69±0.20 (2θ), 21.02±0.20 (2θ), 23.77±0.20 (2θ), 24.07±0.20 (2θ), 25.31±0.20 (2θ), 26.14±0.20 (2θ), 26.73±0.20 (2θ), 27.49±0.20 (2θ), 28.16±0.20 (2θ), 30.05±0.20 (2θ), 30.45±0.20 (2θ), 31.21±0.20 (2θ), 31.51±0.20 (2θ), 35.37±0.20 (2θ) and 37.15±0.20 (2θ) it additionally has at least one X-ray diffraction peak selected from the group consisting of 10.71±0.20 (2θ), 12.68±0.20 (2θ), 22.47±0.20 (2θ), 23.27±0.20 (2θ), 28.88±0.20 (2θ), 29.45±0.20 (2θ), 30.95±0.20 (2θ), 32.89±0.20 (2θ), 33.48±0.20 (2θ), 33.96±0.20 (2θ), 35.96±0.20 (2θ), 36.68±0.20 (2θ), 38.05±0.20 (2θ) and 39.44±0.20 (2θ).

The X-ray powder diffractogramm of the crystalline modification of the salt or cocrystal of malonic acid and (1R,2R)-3-(3-dimethylamino-1-ethyl-2-methyl-propyl)-phenol is shown in FIG. 2.

Another subject-matter of the present invention relates to a crystalline modification of the salt or cocrystal of saccharin and (1R,2R)-3-(3-dimethylamino-1-ethyl-2-methyl-propyl)-phenol.

This crystalline modification of the salt or cocrystal of saccharin and (1R,2R)-3-(3-dimethylamino-1-ethyl-2-methyl-propyl)-phenol according to the invention has at least one or more X-ray diffraction peaks selected from the group consisting of 13.20±0.20 (2θ), 12.73±0.20 (2θ), 13.41±0.20 (2θ), 14.78±0.20 (2θ), 16.16±0.20 (2θ), 17.12±0.20 (2θ), 19.66±0.20 (2θ), 21.20±0.20 (2θ), 21.86±0.20 (2θ), 23.44±0.20 (2θ) and 24.31±0.20 (2θ).

Preferably, the crystalline modification of the salt or cocrystal of saccharin and (1R,2R)-3-(3-dimethylamino-1-ethyl-2-methyl-propyl)-phenol according to the invention may additionally have at least one X-ray diffraction peak selected from the group consisting of 9.24±0.20 (2θ), 11.55±0.20 (2θ), 12.21±0.20 (2θ), 14.40±0.20 (2θ), 23.91±0.20 (2θ), 24.92±0.20 (2θ), 26.18±0.20 (2θ), 26.71±0.20 (2θ), 27.42±0.20 (2θ), 27.95±0.20 (2θ), 28.51±0.20 (2θ), 29.38±0.20 (2θ), 30.12±0.20 (2θ) and 30.84±0.20 (2θ).

The crystalline modification of the salt or cocrystal of saccharin and (1R,2R)-3-(3-dimethylamino-1-ethyl-2-methyl-propyl)-phenol according to the invention may further be characterised in that as well as one or more X-ray diffraction peaks selected from the group consisting of 13.20±0.20 (2θ), 12.73±0.20 (2θ), 13.41±0.20 (2θ), 14.78±0.20 (2θ), 16.16±0.20 (2θ), 17.12±0.20 (2θ), 19.66±0.20 (2θ), 21.20±0.20 (2θ), 21.86±0.20 (2θ), 23.44±0.20 (2θ) and 24.31±0.20 (2θ) and optionally one or more X-ray diffraction peaks selected from the group consisting of 9.24±0.20 (2θ), 11.55±0.20 (2θ), 12.21±0.20 (2θ), 14.40±0.20 (2θ), 23.91±0.20 (2θ), 24.92±0.20 (2θ), 26.18±0.20 (2θ), 26.71±0.20 (2θ), 27.42±0.20 (2θ), 27.95±0.20 (2θ), 28.51±0.20 (2θ), 29.38±0.20 (2θ), 30.12±0.20 (2θ) and 30.84±0.20 (2θ) it additionally has at least one X-ray diffraction peak selected from the group consisting of 9.80±0.20 (2θ), 18.11±0.20 (2θ), 18.54±0.20 (2θ), 20.18±0.20 (2θ), 20.40±0.20 (2θ), 22.99±0.20 (2θ), 25.62±0.20 (2θ), 25.98±0.20 (2θ), 26.49±0.20 (2θ), 27.78±0.20 (2θ), 29.81±0.20 (2θ), 31.99±0.20 (2θ), 32.29±0.20 (2θ), 33.31±0.20 (2θ), 35.13±0.20 (2θ), 36.00±0.20 (2θ), 36.56±0.20 (2θ) and 38.68±0.20 (2θ).

The X-ray powder diffractogramm of the crystalline modification of the salt or cocrystal of saccharin and (1R,2R)-3-(3-dimethylamino-1-ethyl-2-methyl-propyl)-phenol is shown in FIG. 3.

Another subject-matter of the present invention relates to a crystalline modification of the hemi-fumarate salt or cocrystal of (1R,2R)-3-(3-dimethylamino-1-ethyl-2-methyl-propyl)-phenol.

This crystalline modification of the hemi-fumarate salt or cocrystal of (1R,2R)-3-(3-dimethylamino-1-ethyl-2-methyl-propyl)-phenol according to the invention has at least one or more X-ray diffraction peaks selected from the group consisting of 11.86±0.20 (2θ), 15.26±0.20 (2θ), 16.00±0.20 (2θ), 16.21±0.20 (2θ), 17.52±0.20 (2θ), 21.75±0.20 (2θ), 22.35±0.20 (2θ), 24.57±0.20 (2θ) and 25.21±0.20 (2θ).

Preferably, the crystalline modification of the hemi-fumarate salt or cocrystal and (1R,2R)-3-(3-dimethylamino-1-ethyl-2-methyl-propyl)-phenol according to the invention may additionally have at least one X-ray diffraction peak selected from the group consisting of 18.69±0.20 (2θ), 18.87±0.20 (2θ), 19.52±0.20 (2θ), 19.75±0.20 (2θ), 20.03±0.20 (2θ), 21.02±0.20 (2θ), 23.17±0.20 (2θ), 23.96±0.20 (2θ), 25.65±0.20 (2θ), 30.72±0.20 (2θ) and 30.87±0.20 (2θ).

The crystalline modification of the hemi-fumarate salt or cocrystal of (1R,2R)-3-(3-dimethylamino-1-ethyl-2-methyl-propyl)-phenol according to the invention may further be characterised in that as well as one or more X-ray diffraction peaks selected from the group consisting of 11.86±0.20 (2θ), 15.26±0.20 (2θ), 16.00±0.20 (2θ), 16.21±0.20 (2θ), 17.52±0.20 (2θ), 21.75±0.20 (2θ), 22.35±0.20 (2θ), 24.57±0.20 (2θ) and 25.21±0.20 (2θ) and optionally one or more X-ray diffraction peaks selected from the group consisting of 18.69±0.20 (2θ), 18.87±0.20 (2θ), 19.52±0.20 (2θ), 19.75±0.20 (2θ), 20.03±0.20 (2θ), 21.02±0.20 (2θ), 23.17±0.20 (2θ), 23.96±0.20 (2θ), 25.65±0.20 (2θ), 30.72±0.20 (2θ) and 30.87±0.20 (2θ) it additionally has at least one X-ray diffraction peak selected from the group consisting 8.05±0.20 (2θ), 9.99±0.20 (2θ), 10.45±0.20 (2θ), 11.12±0.20 (2θ), 11.51±0.20 (2θ), 13.88±0.20 (2θ), 16.94±0.20 (2θ), 25.85±0.20 (2θ), 26.36±0.20 (2θ), 26.96±0.20 (2θ), 27.60±0.20 (2θ), 28.10±0.20 (2θ), 29.28±0.20 (2θ), 29.86±0.20 (2θ), 31.22±0.20 (2θ), 31.86±0.20 (2θ), 32.43±0.20 (2θ), 33.46±0.20 (2θ), 33.79±0.20 (2θ), 34.28±0.20 (2θ), 34.85±0.20 (2θ), 35.10±0.20 (2θ), 36.85±0.20 (2θ), 37.60±0.20 (2θ), 38.34±0.20 (2θ), 38.67±0.20 (2θ) and 39.15±0.20 (2θ).

The X-ray powder diffractogramm of the crystalline modification of the hemi salt or cocrystal of fumaric acid and (1R,2R)-3-(3-dimethylamino-1-ethyl-2-methyl-propyl)-phenol is shown in FIG. 4.

Another subject-matter of the present invention relates to a crystalline modification of the salt or cocrystal of 1-hydroxy-2-naphthoic acid and (1R,2R)-3-(3-dimethylamino-1-ethyl-2-methyl-propyl)-phenol.

This crystalline modification of the salt or cocrystal of 1-hydroxy-2-naphthoic acid and (1R,2R)-3-(3-dimethylamino-1-ethyl-2-methyl-propyl)-phenol according to the invention has at least one or more X-ray diffraction peaks selected from the group consisting of 13.59±0.20 (2θ), 13.97±0.20 (2θ), 15.36±0.20 (2θ), 18.04±0.20 (2θ), 19.75±0.20 (2θ), 19.98±0.20 (2θ), 20.52±0.20 (2θ), 24.37±0.20 (2θ) and 26.09±0.20 (2θ).

Preferably, the crystalline modification of the salt or cocrystal of 1-hydroxy-2-naphthoic acid and (1R,2R)-3-(3-dimethylamino-1-ethyl-2-methyl-propyl)-phenol according to the invention may additionally have at least one X-ray diffraction peak selected from the group consisting of 14.70±0.20 (2θ), 16.04±0.20 (2θ), 17.43±0.20 (2θ), 18.68±0.20 (2θ), 21.41±0.20 (2θ), 22.88±0.20 (2θ), 23.34±0.20 (2θ), 23.55±0.20 (2θ), 24.17±0.20 (2θ), 25.22±0.20 (2θ), 26.40±0.20 (2θ) and 28.84±0.20 (2θ).

The crystalline modification of the salt or cocrystal of 1-hydroxy-2-naphthoic acid and (1R,2R)-3-(3-dimethylamino-1-ethyl-2-methyl-propyl)-phenol according to the invention may further be characterised in that as well as one or more X-ray diffraction peaks selected from the group consisting of 13.59±0.20 (2θ), 13.97±0.20 (2θ), 15.36±0.20 (2θ), 18.04±0.20 (2θ), 19.75±0.20 (2θ), 19.98±0.20 (2θ), 20.52±0.20 (2θ), 24.37±0.20 (2θ) and 26.09±0.20 (2θ) and optionally one or more X-ray diffraction peaks selected from the group consisting of 14.70±0.20 (2θ), 16.04±0.20 (2θ), 17.43±0.20 (2θ), 18.68±0.20 (2θ), 21.41±0.20 (2θ), 22.88±0.20 (2θ), 23.34±0.20 (2θ), 23.55±0.20 (2θ), 24.17±0.20 (2θ), 25.22±0.20 (2θ), 26.40±0.20 (2θ) and 28.84±0.20 (2θ) it additionally has at least one X-ray diffraction peak selected from the group consisting of 8.01±0.20 (2θ), 10.20±0.20 (2θ), 16.34±0.20 (2θ), 21.74±0.20 (2θ), 25.42±0.20 (2θ), 27.37±0.20 (2θ), 28.17±0.20 (2θ), 28.56±0.20 (2θ), 29.36±0.20 (2θ), 29.63±0.20 (2θ), 30.64±0.20 (2θ), 30.99±0.20 (2θ), 31.66±0.20 (2θ), 31.89±0.20 (2θ), 32.97±0.20 (2θ), 33.81±0.20 (2θ), 34.33±0.20 (2θ), 35.07±0.20 (2θ), 35.81±0.20 (2θ) and 38.40±0.20 (2θ).

The X-ray powder diffractogramm of the crystalline modification of the salt or cocrystal of 1-hydroxy-2-naphthoic acid and (1R,2R)-3-(3-dimethylamino-1-ethyl-2-methyl-propyl)-phenol is shown in FIG. 9.

Another subject-matter of the present invention relates to a crystalline modification of the hemi-salt or cocrystal of (2S, 3S)-Di-benzoyltartaric acid and (1R,2R)-3-(3-dimethylamino-1-ethyl-2-methyl-propyl)-phenol.

This crystalline modification of the hemi-salt or cocrystal of (2S,3S)-Di-benzoyltartaric acid and (1R,2R)-3-(3-dimethylamino-1-ethyl-2-methyl-propyl)-phenol according to the invention has at least one or more X-ray diffraction peaks selected from the group consisting of 9.35±0.20 (2θ), 12.22±0.20 (2θ), 13.41±0.20 (2θ), 14.00±0.20 (2θ), 17.89±0.20 (2θ), 18.28±0.20 (2θ), 18.73±0.20 (2θ), 19.53±0.20 (2θ), 19.98±0.20 (2θ), 23.19±0.20 (2θ) and 24.33±0.20 (2θ).

Preferably, the crystalline modification of the hemi-salt or cocrystal of (2S,3S)-Di-benzoyltartaric acid and (1R,2R)-3-(3-dimethylamino-1-ethyl-2-methyl-propyl)-phenol according to the invention may additionally have at least one X-ray diffraction peak selected from the group consisting of 8.41±0.20 (2θ), 11.76±0.20 (2θ), 16.33±0.20 (2θ), 21.33±0.20 (2θ), 21.60±0.20 (2θ), 22.12±0.20 (2θ), 22.87±0.20 (2θ), 24.94±0.20 (2θ), 25.68±0.20 (2θ), 26.38±0.20 (2θ), 27.78±0.20 (2θ), 28.28±0.20 (2θ), 28.42±0.20 (2θ) and 29.78±0.20 (2θ).

The X-ray powder diffractogramm of the crystalline modification of the hemi salt or cocrystal of (2S,3S)-Di-benzoyltartaric acid and (1R,2R)-3-(3-dimethylamino-1-ethyl-2-methyl-propyl)-phenol is shown in FIG. 10.

Another subject-matter of the present invention relates to a crystalline modification of the salt or cocrystal of sebacic acid and (1R,2R)-3-(3-dimethylamino-1-ethyl-2-methyl-propyl)-phenol.

This crystalline modification of the salt or cocrystal of sebacic acid and (1R,2R)-3-(3-dimethylamino-1-ethyl-2-methyl-propyl)-phenol according to the invention has at least one or more X-ray diffraction peaks selected from the group consisting of 12.16±0.20 (2θ), 15.31±0.20 (2θ), 16.88±0.20 (2θ), 18.90±0.20 (2θ), 22.66±0.20 (2θ), 23.08±0.20 (2θ) and 25.46±0.20 (2θ).

Preferably, the crystalline modification of the salt or cocrystal of sebacic acid and (1R,2R)-3-(3-dimethylamino-1-ethyl-2-methyl-propyl)-phenol according to the invention may additionally have at least one X-ray diffraction peak selected from the group consisting of 9.87±0.20 (2θ), 12.66±0.20 (2θ), 14.83±0.20 (2θ), 15.68±0.20 (2θ), 19.59±0.20 (2θ), 19.82±0.20 (2θ), 21.76±0.20 (2θ), 23.39±0.20 (2θ), 23.92±0.20 (2θ), 24.45±0.20 (2θ), 24.77±0.20 (2θ) and 30.86±0.20 (2θ).

The crystalline modification of the salt or cocrystal of sebacic acid and (1R,2R)-3-(3-dimethylamino-1-ethyl-2-methyl-propyl)-phenol according to the invention may further be characterised in that as well as one or more X-ray diffraction peaks selected from the group consisting of 12.16±0.20 (2θ), 15.31±0.20 (2θ), 16.88±0.20 (2θ), 18.90±0.20 (2θ), 22.66±0.20 (2θ), 23.08±0.20 (2θ) and 25.46±0.20 (2θ) and optionally one or more X-ray diffraction peaks selected from the group consisting of 9.87±0.20 (2θ), 12.66±0.20 (2θ), 14.83±0.20 (2θ), 15.68±0.20 (2θ), 19.59±0.20 (2θ), 19.82±0.20 (2θ), 21.76±0.20 (2θ), 23.39±0.20 (2θ), 23.92±0.20 (2θ), 24.45±0.20 (2θ), 24.77±0.20 (2θ) and 30.86±0.20 (2θ) it additionally has at least one X-ray diffraction peak selected from the group consisting of 19.98±0.20 (2θ), 26.45±0.20 (2θ), 27.12±0.20 (2θ), 27.81±0.20 (2θ), 28.30±0.20 (2θ), 30.20±0.20 (2θ), 31.42±0.20 (2θ), 31.66±0.20 (2θ), 32.19±0.20 (2θ), 33.92±0.20 (2θ), 34.11±0.20 (2θ), 34.39±0.20 (2θ), 37.67±0.20 (2θ), 38.34±0.20 (2θ), 38.92±0.20 (2θ) and 39.81±0.20 (2θ).

The X-ray powder diffractogramm of the crystalline modification of the hemi salt or cocrystal of sebacic acid and (1R,2R)-3-(3-dimethylamino-1-ethyl-2-methyl-propyl)-phenol is shown in FIG. 11.

Another aspect of the present invention is a method for preparing an inventive salt or cocrystal.

According to the present invention, the salt or cocrystal of (a) 3-(3-dimethylamino-1-ethyl-2-methyl-propyl)-phenol and at least one acid (b1) or (b2) may be synthesized by a process including the steps of dissolution of a 3-(3-dimethylamino-1-ethyl-2-methyl-propyl)-phenol compound in a solvent and addition of an acid (b1) or (b2) or an aqueous solution or suspension or an inert solvent solution or suspension of an acid (b1) or (b2) preferably dropwise to the solution of the 3-(3-dimethylamino-1-ethyl-2-methyl-propyl)-phenol compound or providing at least one acid (b1) or (b2) or an aqueous solution or suspension or an inert solvent solution or suspension of said acid (b1) or (b2) and addition, preferably dropwise addition of a solution of the 3-(3-dimethylamino-1-ethyl-2-methyl-propyl)-phenol compound dissolved in an inert solvent or water-comprising inert solvent or mixing 3-(3-dimethylamino-1-ethyl-2-methyl-propyl)-phenol compound and an acid (b1) or (b2) and subsequent addition of an inert solvent or water-comprising inert solvent to said mixture (step 1), stirring or keeping the mixture obtained from step 1 at a certain temperature, preferably at room temperature for a certain period of time (step 2), optionally cooling the mixture obtained from step 2, preferably to a temperature between 20° C. and −40° C. (step 3), collection of the formed solid, which is—at least when component (a) and component (b2) are employed—usually in a crystalline and/or amorphous form, by filtration and optionally drying the solid (step 4).

The term inert solvent is used herein means that the solvent does not react with the solid components, however the solvent may be incorporated in the salts and/or cocrystals.

The inventive process may optionally contain further steps which independently of one another may be preferably carried out after step 2, such as optionally addition of seed crystals, optionally evaporation of a part of the solvent, optionally addition of a solvent, in which the inventive salt or cocrystal is poorly soluble or insoluble, optionally initiation and/or promotion of crystal- and/or co-crystal-precipitation by means of mechanical stimulation.

If a monovalent acid (b1) or (b2) is employed for the preparation of the inventive salt or cocrystal, the amount of said acid employed is preferably in the range of from 0.4 to 10 mol per mol of component (a), more preferably in the range of from 0.6 to 6 mol, and even more preferably in the range of from 0.8 to 5 mol.

If a divalent acid (b1) or (b2) is employed for the preparation of the inventive salt or cocrystal, the amount of said acid employed is preferably in the range of from 0.2 to 10 mol per mol of component (a), more preferably in the range of from 0.3 to 6 mol, and even more preferably in the range of from 0.4 to 5 mol.

Preferably, the concentration of the acid (b1) or (b2) to be employed in the aqueous solution or inert solvent solution is in the range of from 0.1 mol/L to saturation, more preferably in the range of from 1 to 20 mol/L, and even more preferably in the range of from 3 to 15 mol/L.

Preferably, the reaction temperature for the preparation of the inventive salt or cocrystal, preferably in step 2, is in the range of from −40° C. to 150° C., more preferably in the range of from 0° C. to 100° C., even more preferably in the range of from 10° C. to 60° C.

Preferably, the reaction time for the preparation of the inventive salt or cocrystal, preferably in step 2, is in the range of from 5 minutes to 48 hours, more preferably in the range of from 10 minutes to 24 hours, even more preferably in the range of from 30 minutes to 12 hours.

The formed solid obtainable in step 4 may be isolated by filtration, centrifugation or a gradient method and may be optionally washed with an inert solvent (preferably an inert solvent employed in the preparation of the salt or cocrystal) as necessary. The isolated solid may be dried under reduced pressure and/or elevated temperature.

Any inert solvents or water-comprising inert solvents suitable for the preparation of the inventive salt or cocrystal may be employed, e.g. any inert solvents or water-comprising inert solvents which do not inhibit the formation of the salt or cocrystal and which allow the starting material employed, i.e. component (a) and (b1) or (b2) to be dissolved therein to at least an extent necessary for the preparation of the salt or cocrystal.

Preferably, inert solvents or suitable media for the preparation of the inventive salt or cocrystal are selected from the group consisting of aliphatic hydrocarbons, e.g. hexane, pentane, petroleum ether and cyclohexane, aromatic hydrocarbons, e.g. benzene, toluene and xylene, halogenated hydrocarbons, e.g. methylene chloride, chloroform, carbon tetrachloride, dichloroethane, chlorobenzene and dichlorobenzene, ethers, e.g. diethyl ether, diisopropyl ether, dibutyl ether, butyl methyl ether, sec-butyl methyl ether, tert-butyl methyl ether, tetrahydrofuran, dioxane, dimethoxyethane and diethylene glycol dimethyl ether, ketones, e.g. acetone, methyl ethyl ketone, methyl isobutyl ketone and cyclohexanone, esters, e.g. ethyl acetate, propyl acetate and butyl acetate, nitriles, e.g. acetonitrile, propionitrile, butyronitrile and isobutyronitrile, alcohols, e.g. methanol, ethanol, 1-propanol, 2-propanol, 1-butanol, 2-butanol, 2-methyl-1-propanol and 2-methyl-2-propanol, amides, e.g. formamide, dimethylformamide, dimethylacetamide, N-methyl-2-pyrrolidone and hexamethylphosphoric triamide, and any mixtures in any ratio thereof. More preferably, inert solvents suitable for the preparation of the inventive salt or cocrystal are selected from the group consisting of toluene, tert-butyl methyl ether, acetone, ethyl acetate, methanol, ethanol, 1-propanol, 2-propanol and any mixtures in any ratio thereof. Optionally, any of these inert solvents or any combinations thereof may comprise a suitable amount of water.

Another aspect of the present invention is a medicament comprising at least one salt or cocrystal as described herein.

In a preferred embodiment, the medicament is a solid medicinal form. However, liquid or pasty medicinal forms are also possible.

Preferably, the medicament is formulated for oral administration. However, pharmaceutical forms that are adapted for other administration routes are also possible, for example buccal, sublingual, transmucosal, rectal, intralumbar, intraperitoneal, transdermal, intravenous, intramuscular, intragluteal, intracutaneous and subcutaneous administration.

Depending upon the formulation, the medicament preferably contains suitable additives and/or excipients. Suitable additives and/or excipients for the purpose of the invention are all substances for achieving galenic formulations known to the person skilled in the art from the prior art. The selection of these excipients and the amounts to use depend upon how the medicinal product is to be administered, i.e. orally, intravenously, intraperitoneally, intrader-mally, intramusculary, intranasally, buccally or topically.

Suitable for oral administration are preparations in the form of tablets, chewable tablets, dragees, capsules, granules, drops, juices or syrups; suitable for parenteral, topical and inhalative administration are solutions, dispersions, suspensions, easily reconstituted dry preparations and sprays. A further possibility is suppositories for use in the rectum. Use in a depot in dissolved form, a carrier foil or a plaster, optionally with the addition of means to encourage penetration of the skin, are examples of suitable percutaneous administration forms. If administered orally, the most preferred preparation of the inventive medicament is in the form of a tablet.

Examples of excipients and additives for oral administration forms are disintegrants, lubricants, binders, fillers, mould release agents, optionally solvents, flavourings, sugar, in particular carriers, diluents, colorants, antioxidants, etc.

For suppositories, it is possible to use inter alia waxes or fatty acid esters and for parenteral means of application, carriers, preservatives, suspension aids, etc.

Excipients can be for example: water, ethanol, 2-propanol, glycerin, ethylene glycol, propylene glycol, polyethylene glycol, polypropylene glycol, glucose, fructose, lactose, sucrose, dextrose, molasses, starch, modified starch, gelatin, sorbitol, inositol, mannitol, microcrystalline cellulose, methyl cellulose, carboxymethylcellulose, cellulose acetate, shellac, cetyl alcohol, polyvinylpyrrolidone, paraffins, waxes, natural and synthetic rubbers, acacia gum, alginates, dextran, saturated and unsaturated fatty acids, stearic acid, magnesium stearate, zinc stearate, glyceryl stearate, sodium lauryl sulfate, edible oils, sesame oil, coconut oil, groundnut oil, soybean oil, lecithin, sodium lactate, polyoxyethylene and propylene fatty acid ester, sorbitan fatty acid esters, sorbic acid, benzoic acid, citric acid, ascorbic acid, tannic acid, sodium chloride, potassium chloride, magnesium chloride, calcium chloride, magnesium oxide, zinc oxide, silicon dioxide, titanium oxide, titanium dioxide, magnesium sulfate, zinc sulfate, calcium sulfate, potash, calcium phosphate, dicalcium phosphate, potassium bromide, potassium iodide, talc kaolin, pectin, crospovidone, agar and bentonite.

The production of this medicinal product, preparation, medicament and pharmaceutical composition is performed with the aid of means, devices, methods and processes which are well known in the prior art of pharmaceutical formulation, such as those described for example in "*Remington's Phar-* maceutical Sciences", ed A R Gennaro, 17th edition, Mack Publishing Company, Easton, pa. (1985), in particular in Part 8, Chapters 76 to 93.

For example, for a solid formulation, such as a tablet, the active substance of the medicament can be granulated with a pharmaceutical carrier, e.g. conventional tablet ingredients, such as maize starch, lactose, sucrose, sorbitol, talc, magnesium stearate, dicalcium phosphate or physiologically acceptable rubbers, and pharmaceutical diluents, such as water, for example, to form a solid composition containing the active substance in a homogeneous distribution. Here, a homogeneous distribution should be understood as meaning that the active substance is distributed uniformly throughout the entire composition so that this can be easily divided into equally effective single dose forms, such as tablets, capsules, dragees. The solid composition is then divided into single dose forms. The tablets or pills can also be coated or compounded in some other way in order to produce a dosage form with delayed release. Suitable coating means are inter alia polymers acids and mixtures of polymeric acids with materials such as shellac, for example, cetyl alcohol and/or cellulose acetate.

In a preferred embodiment of the present invention the salt or cocrystal is present in the medicament in immediate release form.

In another preferred embodiment of the present invention the salt or cocrystal is present in the medicament in controlled-release form. For the purpose of the specification, the term "controlled-release form" refers to any type of release form other than an immediate release form and includes e.g. a delayed-release form, a prolonged release from, a sustained release form, a slow release form, an extended release form and the like. These terms are well known to any person skilled in the art as are the means, devices, methods and processes for obtaining such type of release.

"Controlled-release forms" such as delayed-release forms of the inventive salt or cocrystal can, for example, be achieved by retardation by means of a matrix, a coating or release systems with an osmotic action (see e.g. EP-A 1 439 829). However, as stated above, in order to achieve a controlled release of the inventive salt or cocrystal, and thus its component (a), such a formulation is not necessary due to the intrinsic controlled release properties of the inventive salt or cocrystal.

Controlled-release forms of the inventive salt or cocrystal are possible from formulations for oral, rectal or percutaneous administration. Preferably, the medicament is formulated for once-daily administration, for twice-daily administration (bid) or for thrice-daily administration, with twice-daily administration (bid) being particularly preferred.

The medicament may contain one or more further drugs besides the inventive salt or cocrystal. Preferably, however, the medicament contains at least one, preferably one, salt or cocrystal as the only drug.

The amounts of the inventive salt or cocrystal to be administered to patients vary depending upon the weight of the patient, the method of administration and the severity of the disease and/or pain. The inventive salt or cocrystal may be administered in amounts up to its maximum daily dosage, which is known to those skilled in the art. In a preferred embodiment, the medicament contains the inventive acid addition salt or cocrystal in an amount of 1 to 1000 mg, more preferably 10 to 500 mg, even more preferably 30 to 400 mg, most preferably 40 to 300 mg, as an equivalent dose based on the salt or cocrystal.

The medicament can be provided as a simple tablet and as a coated tablet (e.g. as a film-coated tablet or dragee). The tablets are usually round and biconvex, but oblong shapes are also possible. Granules, spheroids, pellets or microcapsules, which are used to fill sachets or capsules or pressed into disintegrating tablets, are also possible.

Medicaments containing at least 0.001 to 99.999% of the inventive salt or cocrystal, in particular low, active doses, are preferred in order to avoid side effects. The medicament contains preferably 0.01% by weight to 99.99% by weight of the inventive salt or cocrystal, more preferably 0.1 to 90% by weight, even more preferably 0.5 to 80% by weight, most preferably 1.0 to 50% by weight and in particular 5.0 to 20% by weight. To avoid side effects, it may be advantageous at the start of the treatment to increase the amount of the inventive salt or cocrystal to be administered gradually (titration) to allow the body to become accustomed to the active substance slowly. Preferably, the inventive salt or cocrystal is first administered in a dose which is below the analgesically active dose.

Particularly preferably, the medicament has an oral pharmaceutical form, which is formulated for once daily or twice-daily administration and contains at least one inventive salt or cocrystal in an amount of 10 to 500 mg as an equivalent dose based on the salt or cocrystal.

Another aspect of the present invention is at least one inventive salt or cocrystal for use in the treatment of pain.

Preferably, the pain is selected from the group consisting of inflammatory pain, neuropathic pain, acute pain, chronic pain, visceral pain, migraine pain and pain associated with cancer. Preferably, the pain is moderate to strong.

Another aspect of the present invention is the use of at least one inventive salt or cocrystal for the preparation of a medicament for the treatment of pain.

Preferably, the pain is selected from the group consisting of inflammatory pain, neuropathic pain, acute pain, chronic pain, visceral pain, migraine pain and pain associated with cancer. Preferably, the pain is moderate to strong.

Another aspect of the present invention is a method of treating pain in a mammal, which comprises administering an effective amount of at least one inventive salt or cocrystal to the mammal.

Preferably, the pain is selected from the group consisting of inflammatory pain, neuropathic pain, acute pain, chronic pain, visceral pain, migraine pain and pain associated with cancer. Preferably, the pain is moderate to strong.

Even if the medicaments according to the invention exhibit few side effects only, it may be advantageous, for example, in order to avoid certain types of dependency to use morphine antagonists, in particular naloxone, naltrexone and/or levallorphan, in addition to the inventive salt or cocrystal.

The present invention also relates to a kit comprising a medicament containing an salt or cocrystal and/or dosage forms comprising said salt or cocrystal according to the invention.

The kit according to the invention is preferably designed for in each case once daily, twice daily or three times daily administration of the medicaments (dosage forms) contained therein.

Figure 1:
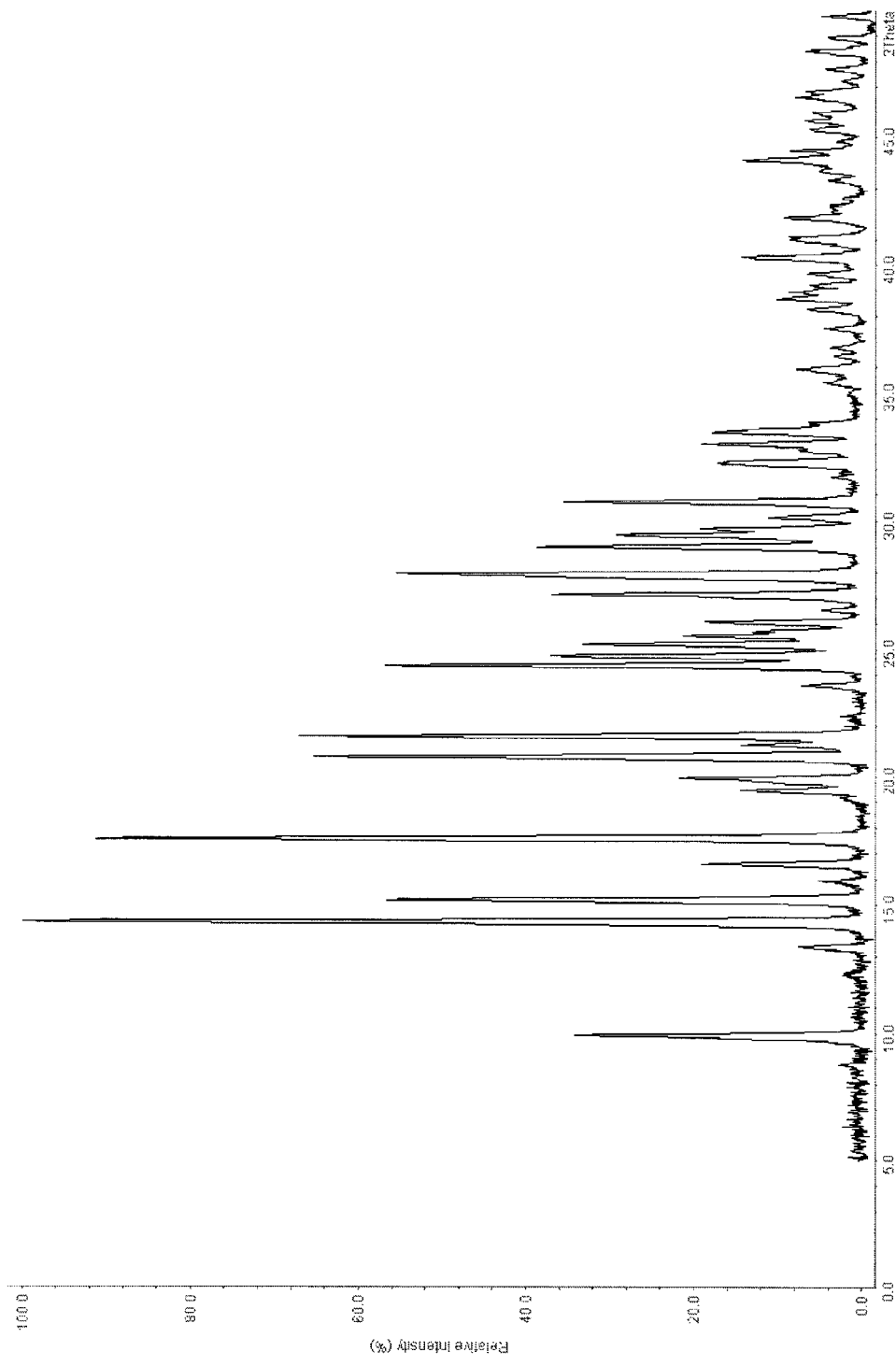
FIG. 1 shows the X-ray powder diffractogramm of tapentadol hydrobromide.
Figure 2:
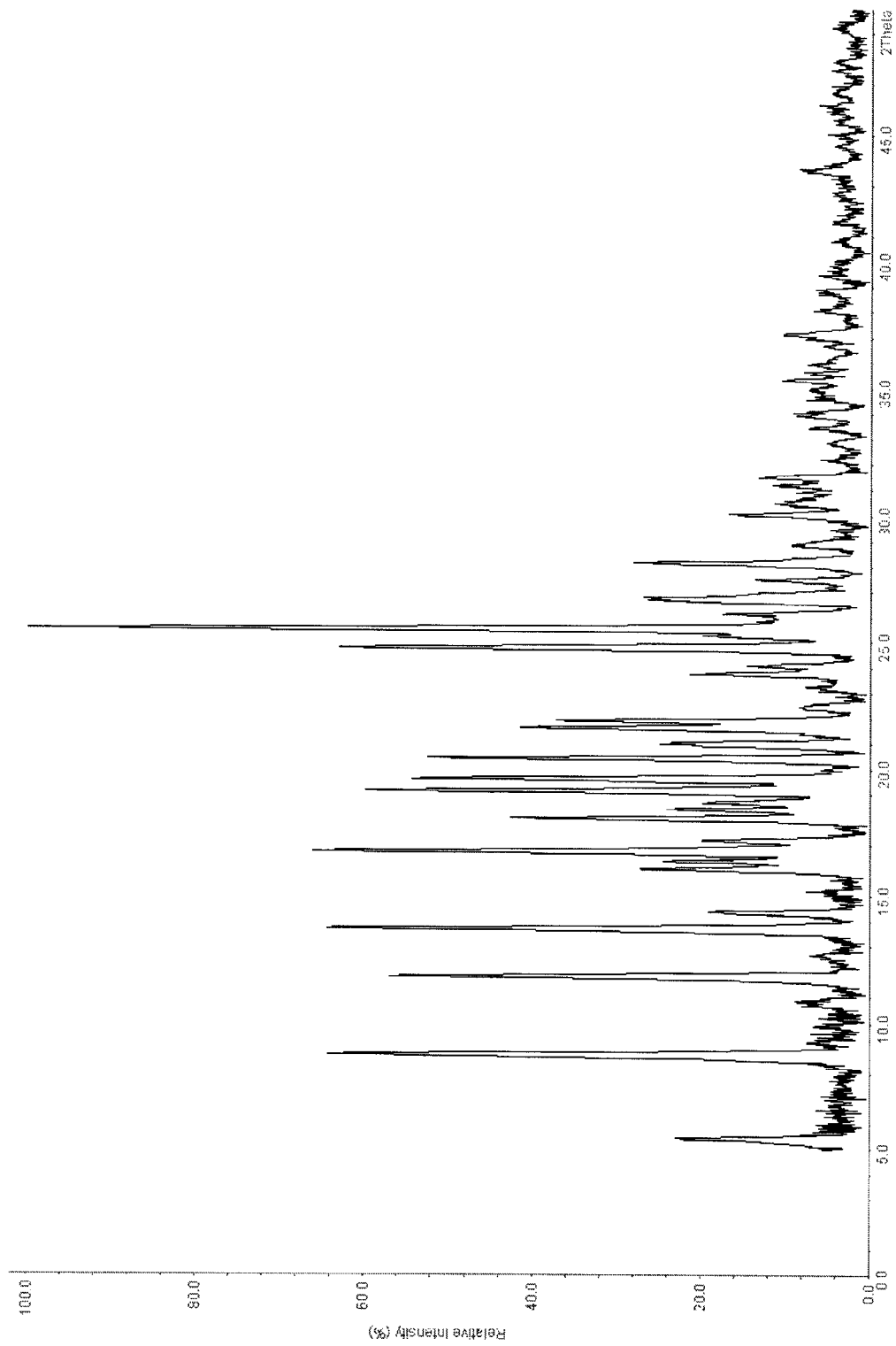
FIG. 2 shows the X-ray powder diffractogramm of tapentadol malonate.
Figure 3:
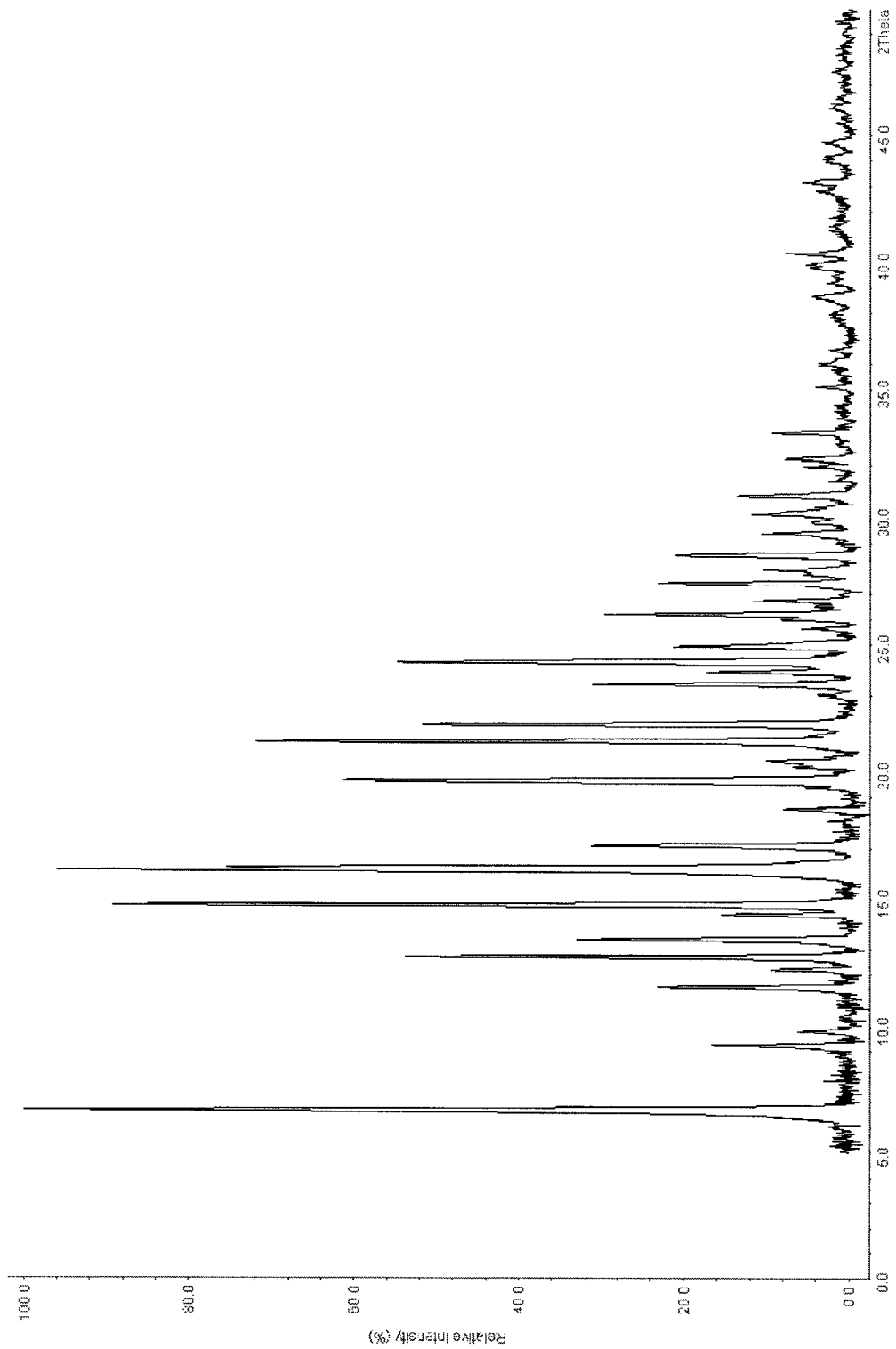
FIG. 3 shows the X-ray powder diffractogramm of tapentadol saccharinate.
Figure 4:
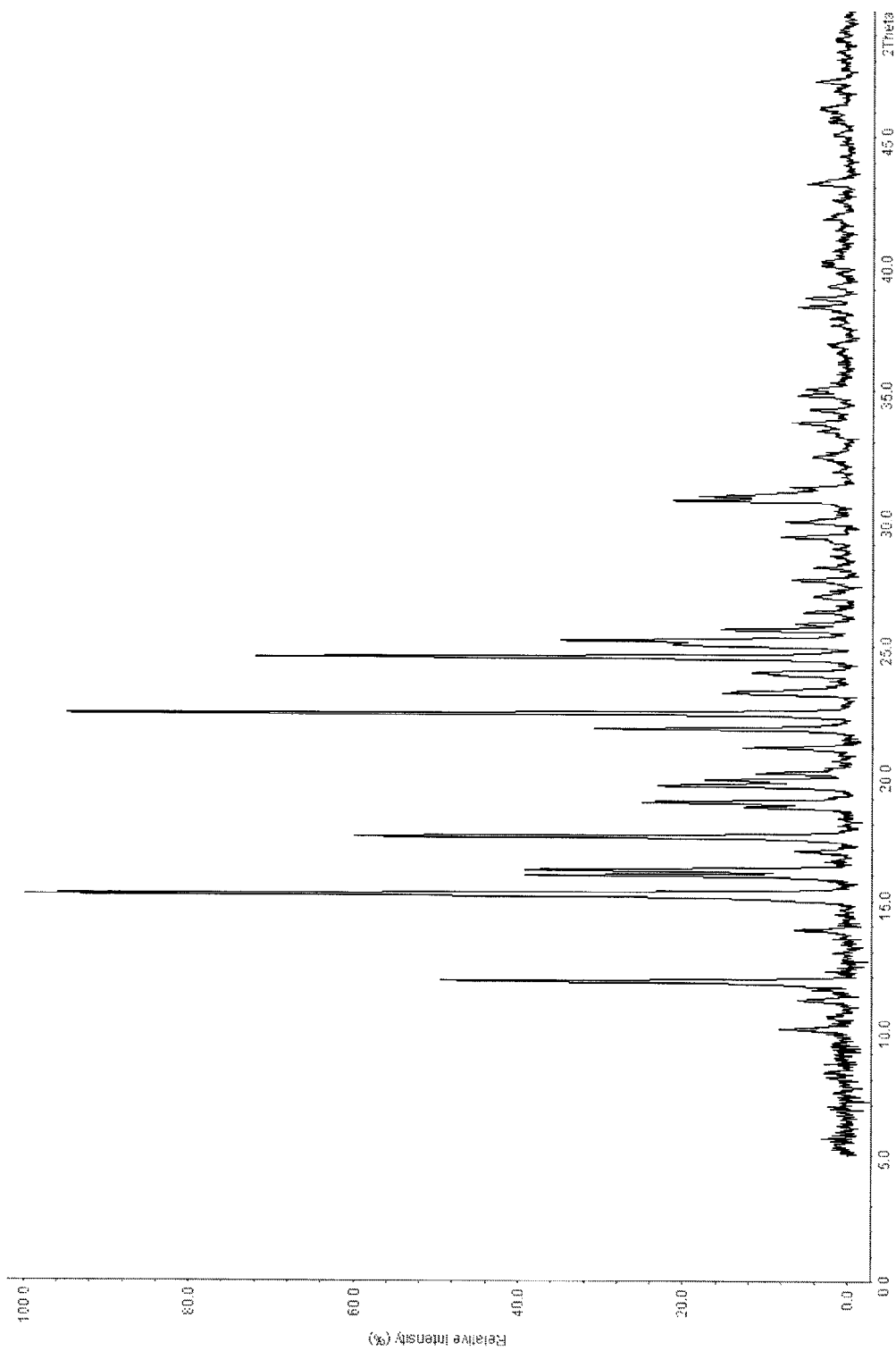
FIG. 4 shows the X-ray powder diffractogramm of tapentadol hemi-fumarate.
Figure 5:
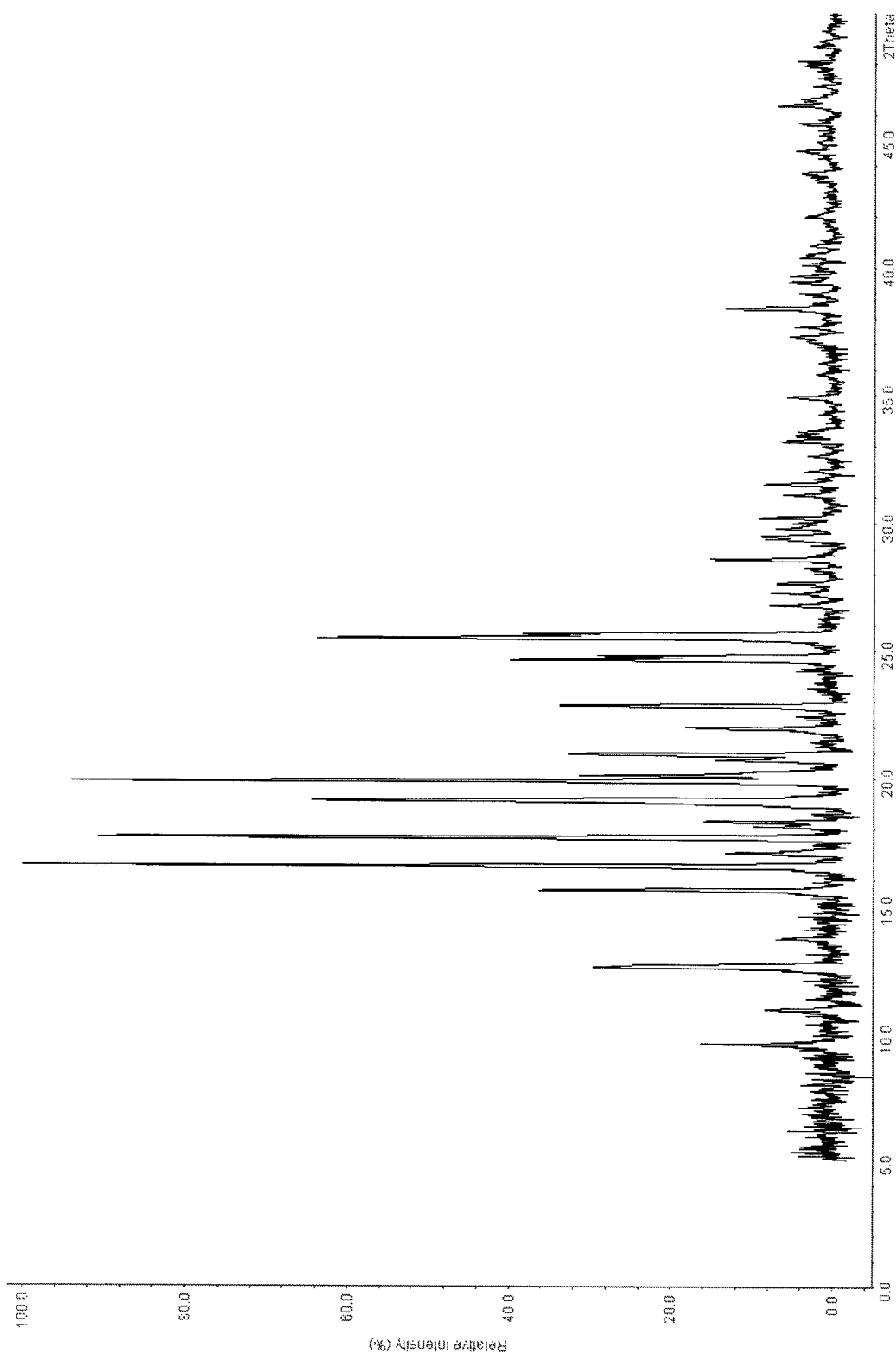
FIG. 5 shows the X-ray powder diffractogramm of tapentadol nicotinate (polymorph $A^1$).
Figure 6:
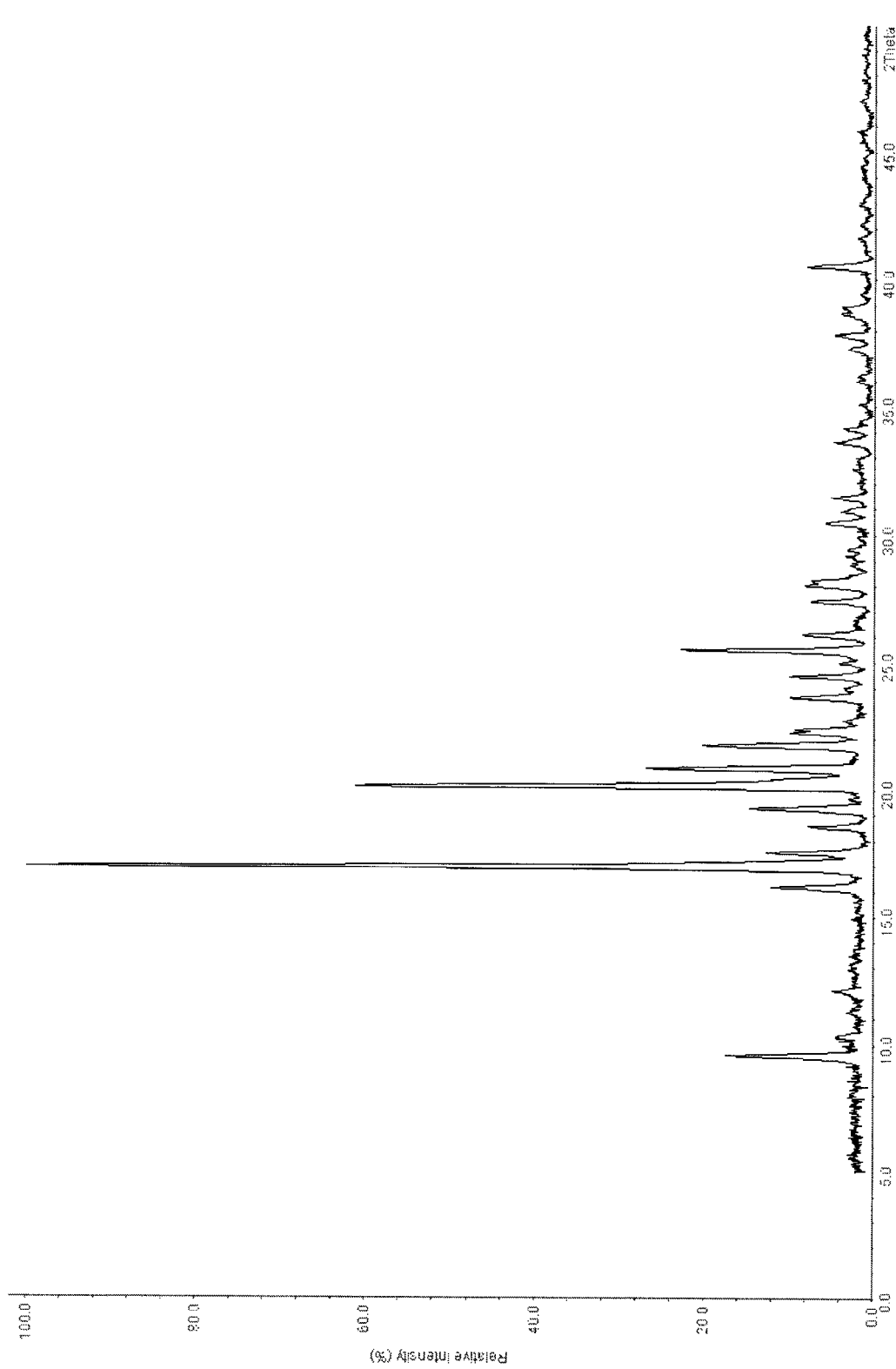
FIG. 6 shows the X-ray powder diffractogramm of tapentadol nicotinate (polymorph $B^1$).
Figure 7:
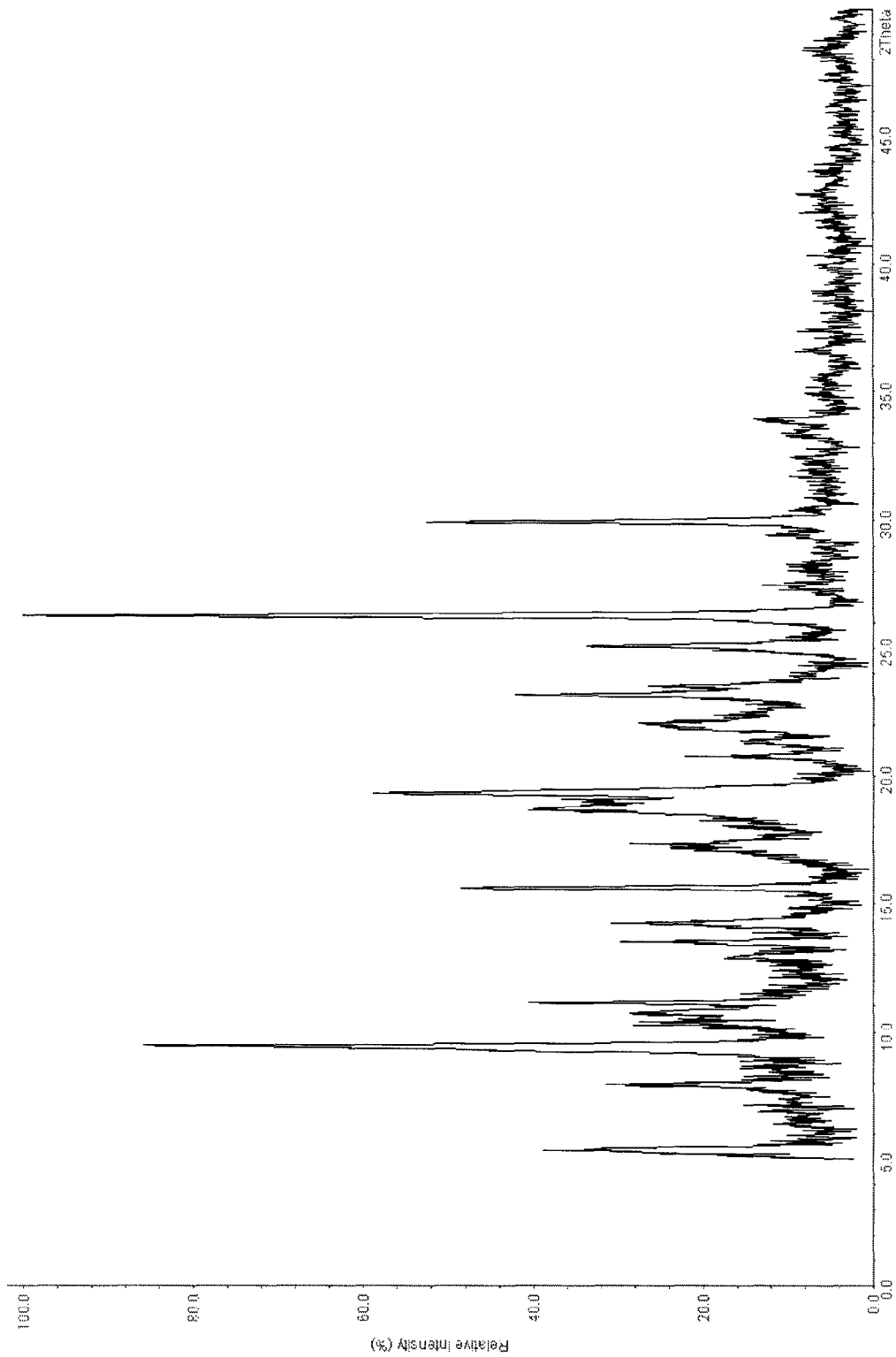
FIG. 7 shows the X-ray powder diffractogramm of tapentadol embonate (polymorph A).
Figure 8:
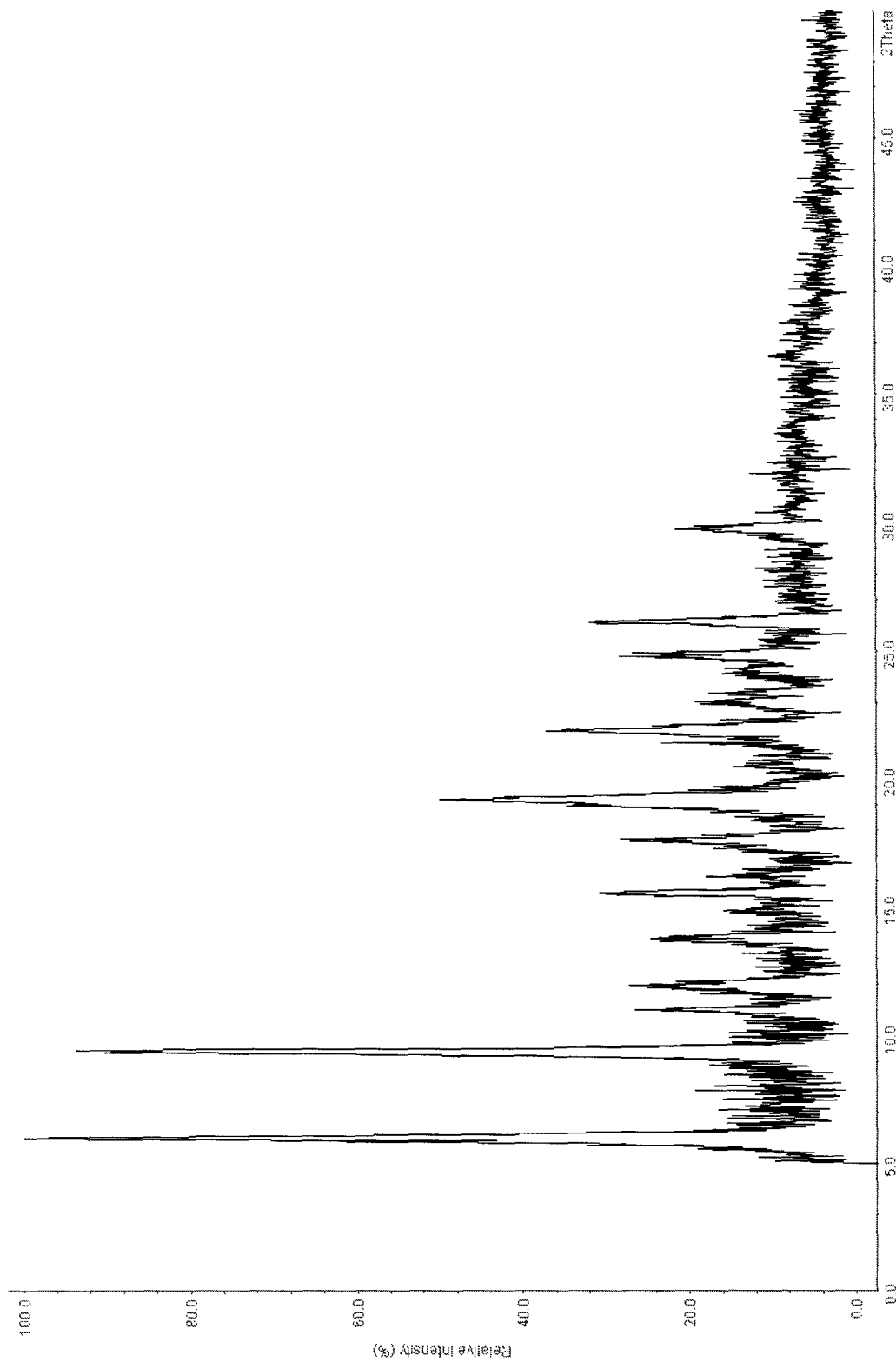
FIG. 8 shows the X-ray powder diffractogramm of tapentadol embonate (polymorph B).
Figure 9:
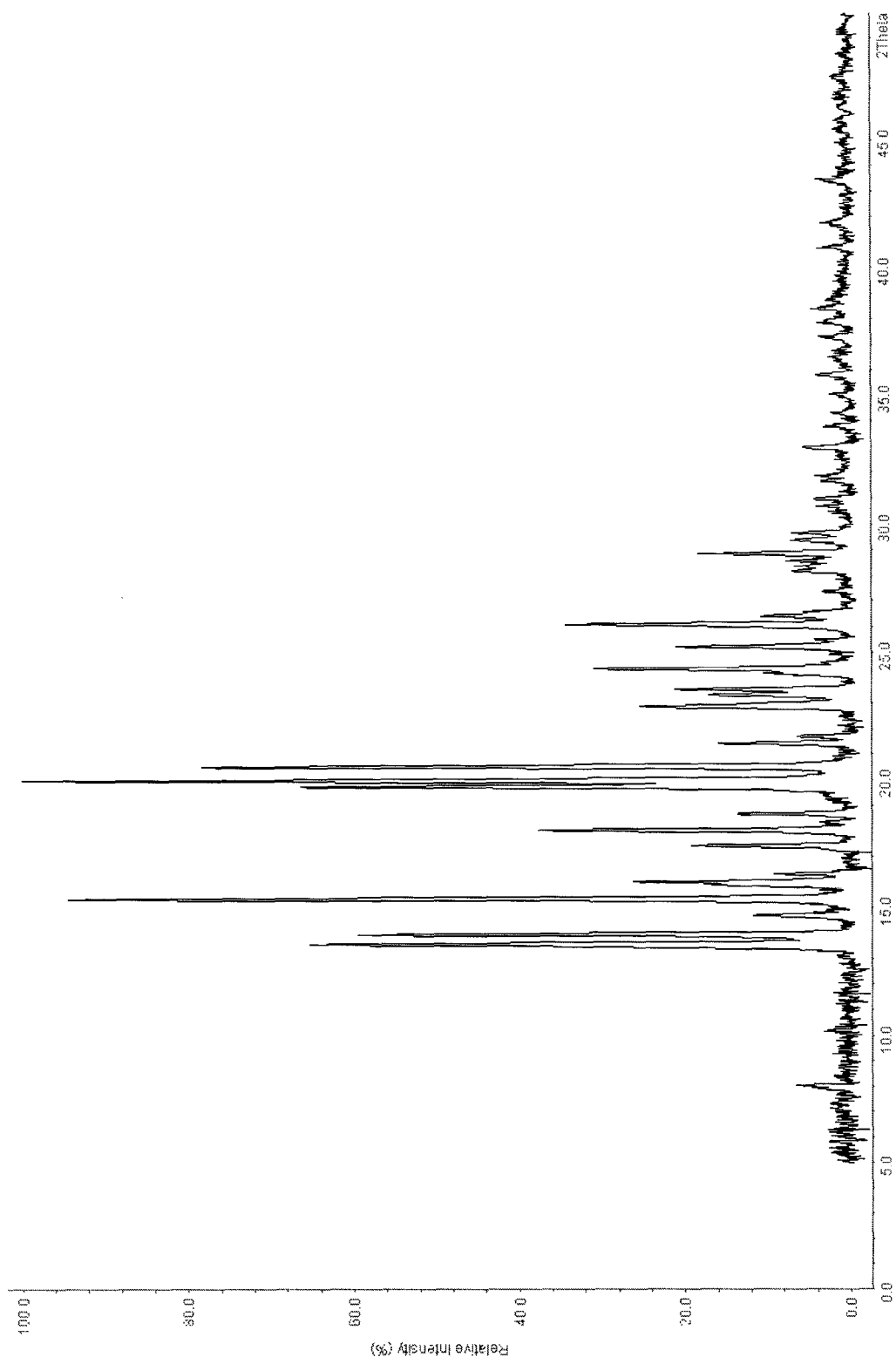
FIG. 9 shows the X-ray powder diffractogramm of tapentadol 1-hydroxy-2-naphthoate.
Figure 10:
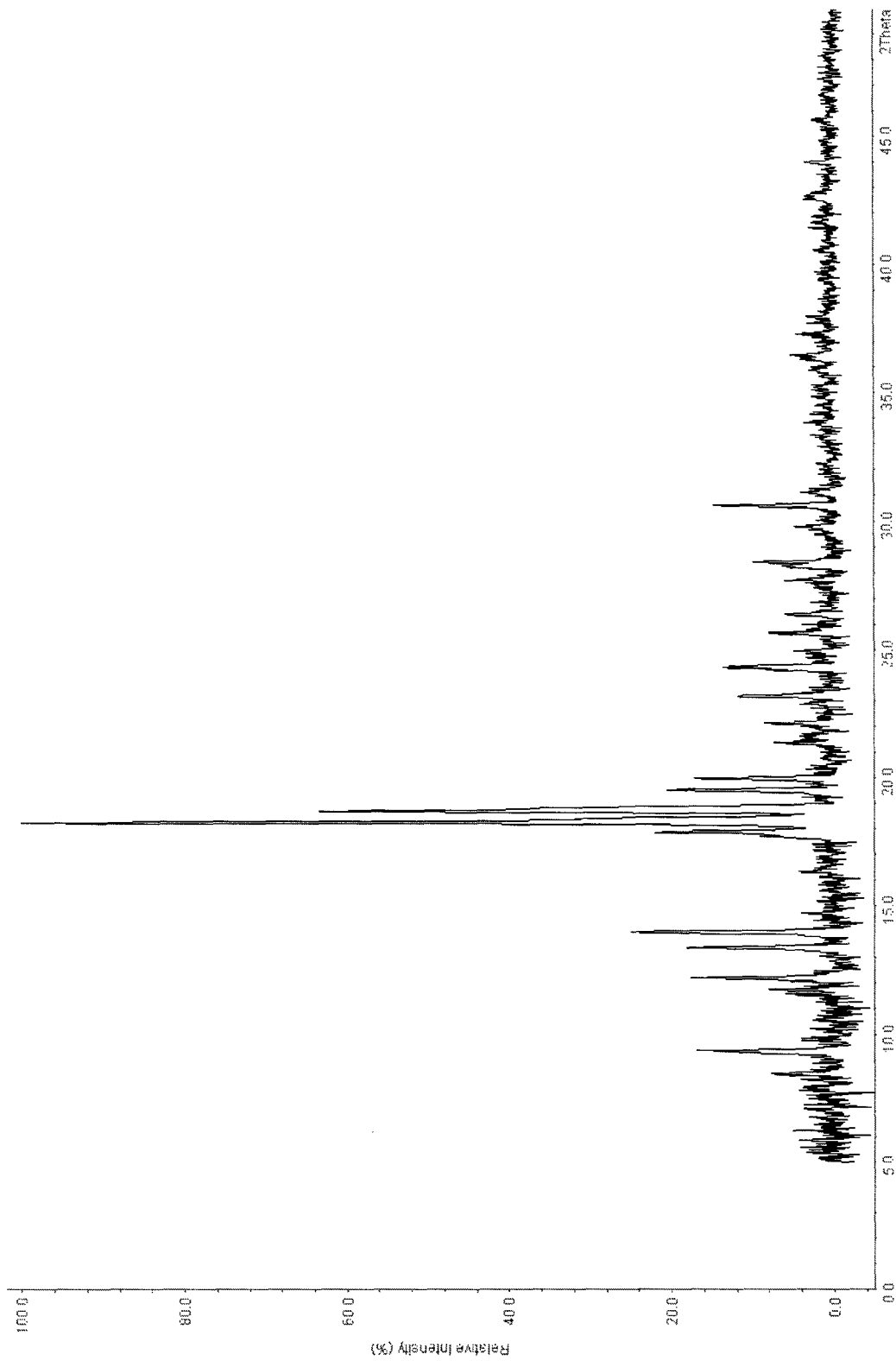
FIG. 10 shows the X-ray powder diffractogramm of tapentadol hemi-(2S,3S)-Di-benzoyltartrate.
Figure 11:
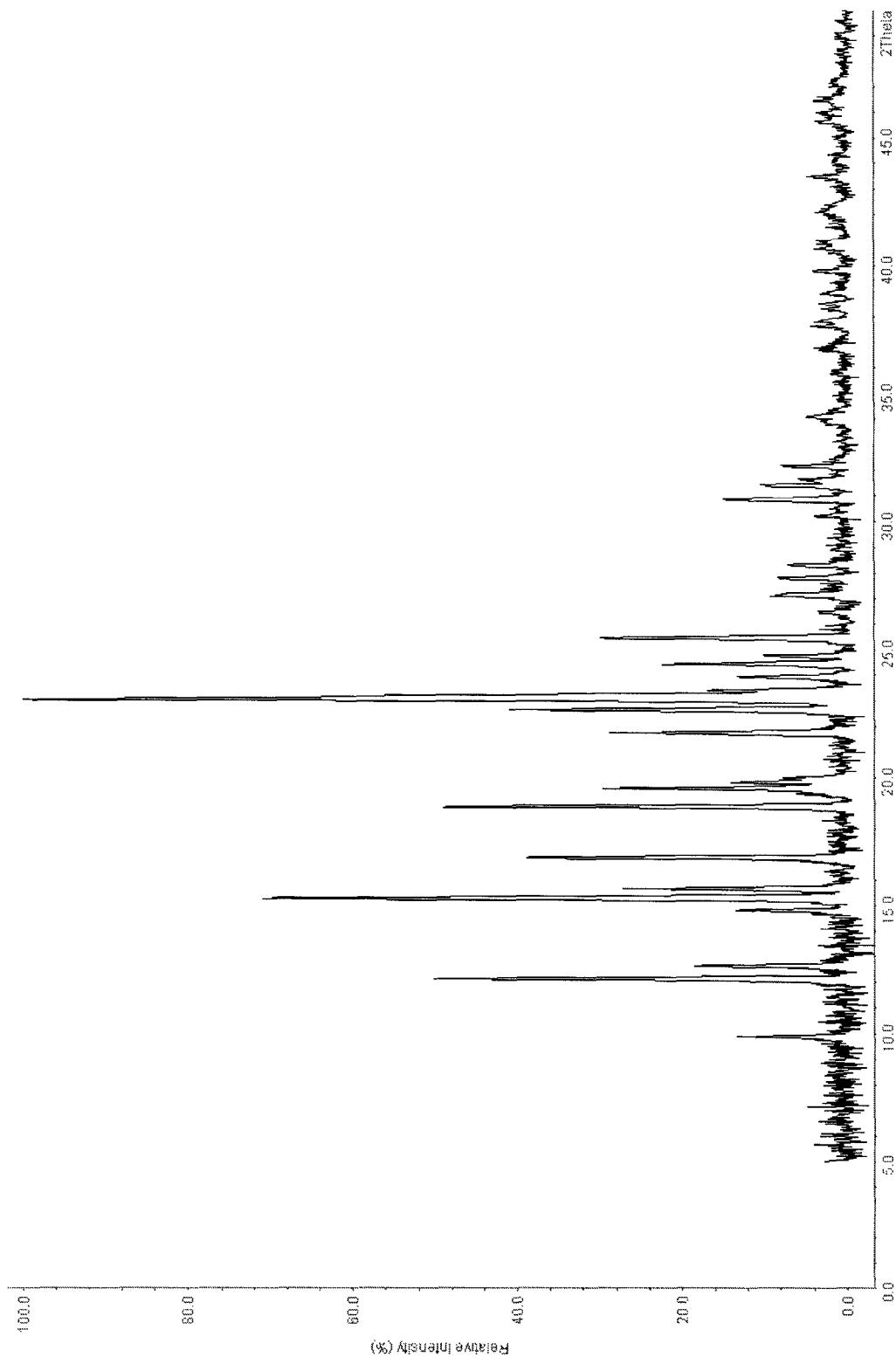
FIG. 11 shows the X-ray powder diffractogramm of tapentadol sebacate.

The following examples serve for a further explanation of the invention but should not be construed as restrictive.

EXAMPLES

For the manufacture of the specific salts or cocrystals as described hereinafter, free tapentadol base (referred to in the following as tapentadol) was employed as starting material which can be obtained as described in EP-A 0 693 475.

Example b1-1

Salt or Cocrystal of Tapentadol and (2S,3S)-Dibenzoyl Tartaric Acid 20 g (0.090 mol) of tapentadol and 16.19 g (0.045 mol) of (+)-(2S,3S) dibenzoyl tartaric acid were dissolved in 400 mL of acetone. The mixture was stirred at room temperature for about 3 hours. The resulting crystalline precipitate was filtered off and dried under reduced pressure (6 mbar) at 40° C. (yield 36.1 g, 100%, melting point (DSC): $T_o$=152.5° C., $T_p$=170.7° C.; 9.7 J/g, $T_o$=185.7° C., $T_p$=188.2° C., 119.1 J/g). $^1$H-NMR analysis showed a 2:1-stochiometry of tapentadol and (+)-(2S,3S) dibenzoyl tartaric acid.

Example b1-2

Salt or Cocrystal of Tapentadol and Sebacic Acid 125 g (0.56 mol) of tapentadol were dissolved in 700 mL of ethyl acetate. To this solution, 114.21 g (0.56 mol) of sebacic acid were added as a solid in portions. Then, 50 mL of ethyl acetate were added. Subsequently, the resulting suspension was stirred for 15 hours. The resulting crystalline white precipitate was then slowly filtered off and dried at 60° C. under reduced pressure (6 mbar) (yield: 232.96 g, 97.37%, melting point (DSC): $T_o$=77.9° C., $T_p$=81.1° C., 99.5 J/g). $^1$H-NMR analysis showed a 1:1-stochiometry of tapentadol and sebacic acid.

Example b1-3

Salt or Cocrystal of Tapentadol and 1-Hydroxy-2-Naphthoic Acid 120 g (0.54 mol) of tapentadol were dissolved in 700 mL of 2-propanol. To this solution, 102.02 g (0.54 mol) of 1-hydroxy-2-naphthoic acid were added as a solid in portions. Then, 100 mL of 2-propanol were added. After complete addition, the resulting suspension was stirred for 18 hours. The crystallized brownish precipitate was then filtered off and dried at 50° C. under reduced pressure (6 mbar) (yield: 199.43 g, 89.83%, melting point (DSC): $T_o$=114.9° C., $T_p$=122.7, ° C., 1.0 J/g; $T_o$=157.6° C., $T_p$=159.9° C., 78.3 J/g). $^1$H-NMR analysis showed a 1:1-stochiometry of tapentadol and 1-hydroxy-2-naphthoic acid.

Example b1-4

Salt or Cocrystal of Tapentadol and Embonic Acid b1-4-1:

8 g (0.036 mol) of tapentadol and 14.037 g of embonic acid (0.036 mol) were suspended in 300 mL of 2-propanol. After addition, the resulting suspension was stirred for 19 hours. The crystallized yellow precipitate was then slowly filtered off and dried at 50° C. under reduced pressure (6 mbar) for 7 hours (yield: 20.86 g, 94.7%, melting point (DSC): $T_o$=114.7° C., $T_p$=122.0, ° C.; 1.5 J/g; $T_o$=214.8° C., $T_p$=219.1° C., 58.0 J/g). $^1$H-NMR analysis showed a 1:1-stochiometry of tapentadol and embonic acid.

b1-4-2:

877.32 mg of embonic acid (0.00226 mol) were suspended in 50 mL of ethanol. To this mixture, 1 g (0.0045 mol) of tapentadol in 5 mL of ethanol was added. After addition, the resulting suspension was stirred for 1 hour. The crystallized white precipitate was then slowly filtered off and dried at 40° C. under reduced pressure (6 mbar) for 3 days (yield: 1.564 g, 83.3%, melting point (DSC): $T_o$=222.6° C., $T_p$=226.5, ° C., 96.7 J/g). $^1$H-NMR analysis showed a 2:1-stochiometry of tapentadol and embonic acid (hemi-embonate).

b1-4-3:

110 g (0.496 mol) of tapentadol were dissolved in 3 L of 2-propanol. To this solution, 193.0 g (0.496 mol) of embonic acid were added as a solid to the resulting solution in portions. Then, 1 L of 2-propanol was added. After addition, the resulting suspension was stirred for 24 hours. The crystallized yellow precipitate was then slowly filtered off and dried at 60° C. under reduced pressure (6 mbar) (yield: 298.14 g, 98.36%). $^1$H-NMR analysis showed a 1:0.9-stochiometry of tapentadol and embonic acid. To remove the excessive free tapentadol base, the solid was suspended in 1.7 L of ethyl acetate and stirred. After 3 hours, the crystallized yellow precipitate was then slowly filtered off and dried at 60° C. under reduced pressure (3 mbar) (yield: 288.43 g, 95.16%; melting point (DSC): $T_o$=217.3° C., $T_p$=220.1, ° C.; 57.2 J/g. Weight loss (TGA, range 31 to 171° C.): less then 0.1%. $^1$H-NMR analysis showed a 1:1-stochiometry of tapentadol and embonic acid. According to XRPD analysis polymorph A was obtained.

b1-4-4:

501.32 mg of tapentadol and 878.83 mg of embonic acid were given into a PLS-vial and suspended subsequently in 30 mL of tetrahydrofuran. The resulting mixture was then vortexed at 30° C. and 400 rpm overnight. Afterwards the solvent was evaporated off to yield a yellow oil that was left in the refrigerator for crystallization. After 7 days a very rigid yellow solid was obtained, which was analysed via $^1$H-NMR spectroscopy. It was found that the sample contained approximately 8% tetrahydrofuran. The solid was therefore dried at 40° C. and approximately 7 mbar for 16 hours. $^1$H-NMR analysis of the dried solid showed a 1:1-stochiometry of tapentadol and embonic acid with approximately 5% tetrahydrofuran. The product showed a melting point (DSC) of $T_o$=35.3° C.; $T_p$=58.0° C.; 1.4 J/g; $T_o$=125.2° C.; $T_p$=130.1° C.; 46.7 J/g $T_o$=208.6° C.; $T_p$=217.2° C.; 41.0 J/g. Weight loss (TGA; range 53 to 167° C.): −5.7%; $T_o$=119.41° C.; $T_o$=205.50° C. According to XRPD analysis polymorph B was obtained.

Example b1-5

Salt or Cocrystal of Tapentadol and Nitric Acid 20 g (0.090 mol) of tapentadol were dissolved in 70 mL of acetone. To this solution were added 6.30 mL of nitric acid at room temperature in 100 µL-portions. The solvent was evaporated off under reduced pressure and the resulting yellow oil was stirred at room temperature for 16 h. After 16, part of the oily material was crystallized. 50 mL of ethyl acetate were added and the remaining oily material also crystallized within minutes. 40 mL of the solvent was evaporated. 60 mL of acetone were added. The resulting suspension was refluxed for 10 minutes at 50° C. 100 mL of acetone were added and the mixture was again refluxed for 10 minutes at 50° C. 40 mL of the solvent was evaporated and the resulting mixture stirred for 1.5 hours. The crystallized precipitate was then filtered off and dried under reduced pressure (6 mbar) at 40° C. (yield 21.32 g, 83%, melting point (DSC): $T_o$=86.9° C., $T_p$=88.2° C., 0.4 J/g; $T_o$=119.7° C., $T_p$=121.3° C., 119.3 J/g). $^1$H-NMR analysis showed a 1:1-stochiometry of tapentadol and nitric acid.

Example b2-1a

Salt or Cocrystal of Tapentadol and Nicotinic Acid

To 20 g (0.090 mol) of tapentadol and 11.126 g (0.090 mol) of nicotinic acid 120 mL of THF were added, resulting in a grey-colored suspension. The precipitate of said suspension was then filtered off. The filtrate was kept at room temperature and the solvent was slowly evaporated off. After 23 hours a green-colored oil was obtained to which 150 mL of n-hexane were added. The mixture of n-hexane and the oily material was then stirred for 1 hour at 50° C. resulting in a mixture of n-hexane and a white-colored oily material, which began to crystallize slowly. The resulting mixture was stirred for another 3 hours at 50° C. until about half of the solvent had been evaporated off. The mixture was then kept at room temperature for another 23 hours. The precipitate was filtered off, washed with 40 mL of n-hexane and dried under reduced pressure (6 mbar) at 40° C. yielding a grey-colored solid (28.73 g, 92.3%). $^1$H-NMR analysis showed a 1:0.9-stochiometry of tapentadol and nicotinic acid. The obtained product was a mixture of two polymorphous forms of the salt or cocrystal and additionally contained free tapentadol base. In order to obtain a pure crystalline form of the salt or cocrystal 26.309 g of said product were suspended in 350 mL of diethyl ether and stirred at room temperature. The mixture was kept at room temperature for 4 days and the resulting crystallized precipitate was filtered off and dried at 40° C. under reduced pressure (yield: 24.304 g, 92.38%, melting point (DSC): $T_o$=66.2° C., $T_p$=72.7° C., 6.7 J/g; $T_o$=100.6° C., $T_p$=104.2° C., 79.9 J/g). $^1$H-NMR analysis showed a 1:1-stochiometry of tapentadol and nicotinic acid. According to XRPD a mixture of two polymorphs was obtained.

Example b2-1b

Salt or Cocrystal of Tapentadol and Nicotinic Acid 500 mg (0.0023 mol) of tapentadol were dissolved in 4 mL acetone. 278 mg nicotinic acid were dissolved in 22 mL tetrahydrofuran at 55° C. and added to the solution of tapentadol The solvent was evaporated over night at 23° C. with a flow of air. After 18 hours 6 mL of hexane were added to the yellowish oil and scratched mechanically with a spatula giving an white to off white oil. Again the solvent was evaporated at 23° C. by application of a flow of air for one hour giving a white to off white oil. The said oil was dried at 40° C. and under reduced pressure (6 mbar) for two hours yielding an almost colorless to colorless oil. After cooling to 23° C. the said oil remained colorless and sticky. Furthermore 2 mL of hexane were added to the oil and the mixture was scratched with a spatula. Over 4 days the solvent was slowly evaporated off yielding white to grey crystalline material (agglomerates). Again 6 mL of hexane were added, agglomerates were reduced in size mechanically with a spatula. After 24 hours of vortexing at 21° C. the grey solid was filtered off and dried at 40° C. under reduced pressure for 1 hour yielding grey to white crystals (yield: 749 mg, 96.3%, melting point (DSC): $T_o$=70.5° C., $T_p$=76.2° C., 103.3 J/g; weight loss (TGA, range: 27 to 171° C.): −5.9%). $^1$H-NMR analysis showed a 1:1-stochiometry of tapentadol and nicotinic acid. According to XRPD analysis polymorph B$^1$ was obtained.

Example b2-1c

Salt or Cocrystal of Tapentadol and Nicotinic Acid 120.0 g tapentadol and 66.744 g nicotinic acid (1 equivalent) were given into a 1 L flask and 700 ml tetrahydrofuran were added subsequently. A grey-brownish suspension was obtained comprising a little amount of undissolved white solid (which was analysed to be nicotinic acid). The suspension was stirred at room temperature for 17 hours and still contained undissolved nicotinic acid. 100 mL of tetrahydrofurane were added, but the nicotinic acid still did not dissolve completely. Within 10 minutes the suspension was heated to its boiling point with a heat gun. After 2 minutes a brownish solution was obtained, which was cooled to room temperature and evaporated off to a volume of approximately 600 mL in an airstream. Subsequently, the solution was evaporated to dryness using a water bath at 40° C. A viscous oil was obtained that could not be dried completely. The oil was dried in vacuo at 100 mbar. Subsequently 500 mL n-hexane were added and the oil was distributed on the wall of the flask by means of a spatula (white oil on the wall). The solvent was evaporated off overnight in an airstream. After 17 hours a white solid was obtained on the wall of the flask and a greenish solid was obtained at the bottom of the flask with white crystals on its surface. The very hard residue was reduced to smaller parts with a spatula. Subsequent to filtration the white solid and the greyish-white solid were pestled and combined with the filtrate. N-Hexane was added to this suspension (to a total volume of 700 mL) and the suspension was stirred at room temperature. After 17 hours at room temperature the solid was filtered off, sucked dry and then further dried at 40° C. and approximately 3 mbar. The filtrate was discarded. After 3 hours the solid was pulverized and dried further to yield 185.406 g (99.28 of theoretic yield) of solid product. $^1$H-NMR analysis showed a 1:1-stochiometry of tapentadol and nicotinic acid. XRPD showed that only one polymorphic form (polymorph $A^1$) was obtained. Melting point (DSC): $T_o$=40.16° C.; $T_p$=54.65° C.; 1.39 J/g; $T_o$=102.90° C.; $T_p$=105.28° C.; 97.93 J/g, TG yielded −0.19% (29.76-135.97° C.); $T_o$=100.22° C.; weight loss (TGA, range: 25 to 148° C.): less then 0.3%).

Example b2-2

Salt or Cocrystal of Tapentadol and Hydrobromic Acid 20 g (0.090 mol) of tapentadol were dissolved in 400 mL of ethyl acetate. To this solution, 10.22 mL (0.090 mol) of hydrobromic acid (48%) were added dropwise. After addition, the resulting suspension was stirred for another 3 hours. The crystallized precipitate was filtered off and dried at 40° C. under reduced pressure (6 mbar) (yield: 25.96 g, 95.0%, 1:1-stochiometry of tapentadol and hydrobromic acid; melting point (DSC): $T_o$=184.9° C., $T_p$=185.4° C., 110.4 J/g).

Example b2-3

Salt or Cocrystal of Tapentadol and Sulfuric Acid b2-3-1:

500 mg (2.26 mmol) of tapentadol were dissolved in 5 mL of acetone. To this solution, 125 µL of sulfuric acid (96%) were added. The mixture was stirred for 30 minutes at room temperature. The solvent was then evaporated off at 50° C. To the remaining oily yellowish residue 5 mL of cyclohexane were added and the resulting mixture was stirred for 30 minutes. Subsequently, the mixture was kept at room temperature for 8 days. The oily residue was then dissolved in 5 mL of ethanol. The solvent was partly evaporated off (about 4 mL) and 5 mL of cyclohexane were added again and the resulting mixture was stirred for 30 minutes and kept for 6 days at room temperature yielding an oily material. The solvent was slowly evaporated off at room temperature and under normal pressure. After 7 days the oily material had crystallized. 5 mL of n-hexane were added resulting in a white suspension. The resulting suspension was stirred for another 30 minutes and kept at room temperature for another 6 days. The precipitated crystallized solid was the filtered off and dried in vacuo (yield: 678.73 mg, 94.1%, melting point (DSC): $T_o$=63.1° C., $T_p$=65.1° C., 14.1 J/g; $T_o$=72.6° C., $T_p$=77.5° C., 83.8 J/g).

b2-3-2:

44.3 mg (0.2 mmol) of tapentadol were dissolved in 1 mL of ethanol. To this solution, 10.7 µL (0.2 mmol) of sulfuric acid (96%) were added. The solvent was then evaporated off at 50° C. within 15 minutes. The remaining colorless oil was kept for 13 days at room temperature. After 13 days the oil had completely crystallized (yield: 62 mg, 97.0%). $^1$H-NMR analysis showed a 1:1-stochiometry of tapentadol and sulfuric acid (sulfate salt or cocrystal of tapentadol).

Example b2-4

Salt or Cocrystal of Tapentadol and Fumaric Acid b2-4-1:

20 g (0.090 mol) of tapentadol and 5.244 g (0.045 mol) of fumaric acid were homogenized in a 250 mL-flask. 200 mL of 2-propanol were added and the resulting mixture was stirred at 40° C. for about 10 minutes. The solvent was then partly evaporated off under reduced pressure. During evaporation, a white solid crystallized. 100 mL of ethyl acetate were added and the resulting suspension was stirred for another 30 minutes at room temperature. The resulting mixture was then kept at room temperature for 7 days. The precipitated crystallized solid was filtered off, washed with 20 mL of ethyl acetate. The solvents were evaporated under reduced pressure and the remaining solid was dried in vacuo (yield: 24.765 g, 98.1%; melting point (DSC): $T_o$=134.0° C., $T_p$=135.7° C., 125.1 J/g). $^1$H-NMR analysis showed a 2:1-stochiometry of tapentadol and fumaric acid (hemi fumarate).

b2-4-2:

To 31.464 g (0.271 mol) of fumaric acid was added 1 L of acetone. The resulting mixture was stirred for 30 minutes. To this suspension, a solution of 120 g (0.542 mol) of tapentadol in 500 mL of acetone was added dropwise within 50 minutes. After addition of about 120 mL of said solution, the starting material is completely dissolved. After addition of about 150 mL of said solution, a white solid begins to precipitate. After addition of the complete solution of tapentadol, the solid had turned into an oily material. The resulting mixture was stirred at room temperature for another 10 minutes. After about 10 minutes the oily material started to crystallize. The resulting mixture was then kept at room temperature for 19 hours. The crystallized solid was filtered off and dried under reduced pressure (6 mbar) at 40° C. (yield: 147.24 g, 97.2%; melting point (DSC): $T_o$=134.0° C., $T_p$=135.1° C., 127.6 J/g). $^1$H-NMR analysis showed a 2:1-stochiometry of tapentadol and fumaric acid (hemi fumarate).

Example b2-5

Salt or Cocrystal of Tapentadol and Malonic Acid 20 g (0.090 mol) of tapentadol and 9.403 g of malonic acid (0.090 mol) were dissolved in 300 mL of ethyl acetate. After addition, the resulting suspension was stirred for 18 hours. The crystallized precipitate was then filtered off and dried at 40° C. under reduced pressure (6 mbar) (yield: 28.797 g, 97.9%, melting point (DSC): $T_o$=109.8° C., $T_p$=111.4° C., 86.9 J/g). $^1$H-NMR analysis showed a 1:1-stochiometry of tapentadol and malonic acid.

Analysis—NMR

Structural characterization was conducted using $^1$H-NMR spectroscopy at 400 MHz.

Instrument: Bruker Avance II 400 equipped with a BBO (Broad Band Observ) probe.

Solvent: D6-dimethyl sulfoxide 99.9 atom-%, 0.1 v/v-% TMS (Aldrich) or Chloroform-d 99.8 atom-%, 0.1 v/v-% TMS (Aldrich)

Temperature: 303 (±1) K

The TMS (Tetramethylsilane) signal was used as an internal reference at 0.00 ppm.

Analysis—XRPD

X-ray Powder Diffractometry (XRPD, X-ray Powder Diffraction):

XRPD investigations were conducted with a STOE Stadi P X-ray powder diffractometer in transmission geometry, using $CuK\alpha_1$ radiation made monochromatic by means of a germanium single crystal.

Stoe Stadi P
Diffractometer: Transmission
Monochromator: Curved, Germanium (111)
Wavelength: Cu Kα
Detektor: Linear PSD
Scan Modus Transmission/Moving PSD/Fixed omega
Scan Type: 2Theta: Omega (2Theta: 2°-50°, step 0.5°, Omega 1°-25°, step 0.25°, time/step 30 s)

D-spacings may be calculated using Bragg's law from the 2θ values, based on a wavelength of 1.54060 Å. As a general rule the 2θ values have an error rate of ±0.2° in 2θ. The experimental error for the d-spacing values therefore depends on the position of the line (of the peak).

Analysis—DSC

Differential Scanning calorimetry (DSC) measurements were performed with a Mettler-Toledo DSC 821 Differential Thermal Analyzer.

Unless otherwise specified, the samples were weighed in a aluminium crucible (lid with pinhole) and measured in a nitrogen flow. Generally DSC investigations were performed in a temperature range of 25 to about 200° C. or resp. 350° C. with a heating rate of 10° C./min.

The temperatures specified in relation to DSC analyses are, unless otherwise specified, the temperatures of the peak maxima (peak temperature $T_P$). Onset temperatures of peaks are indicated by $T_O$. Specific heat is given in J/g.

Analysis—TGA

Thermogravimetric investigations were performed with a Mettler-Toledo TGA/SDTA851.

Unless otherwise specified, the samples were weighed in a aluminium crucible and measured in nitrogen flow. Generally TGA investigations were performed in a temperature range of 25 to about 200° C. or resp. 350° C. with a heating rate of 10° C./min.

Analysis—Dissolution

Dissolution experiments were performed with a Sotax AT7 smart using UV-detection (Photometer Perkin Elmer). Vessels equipped with a Wood apparatus (for intrinsic dissolution) were used.

The tablets with a surface of 0.5 cm$^2$ (diameter 8 mm) were made by applying press capacity of 200 N (200 kg applied for 1 min) using about 100 mg of the particular substance.

Figure 12:
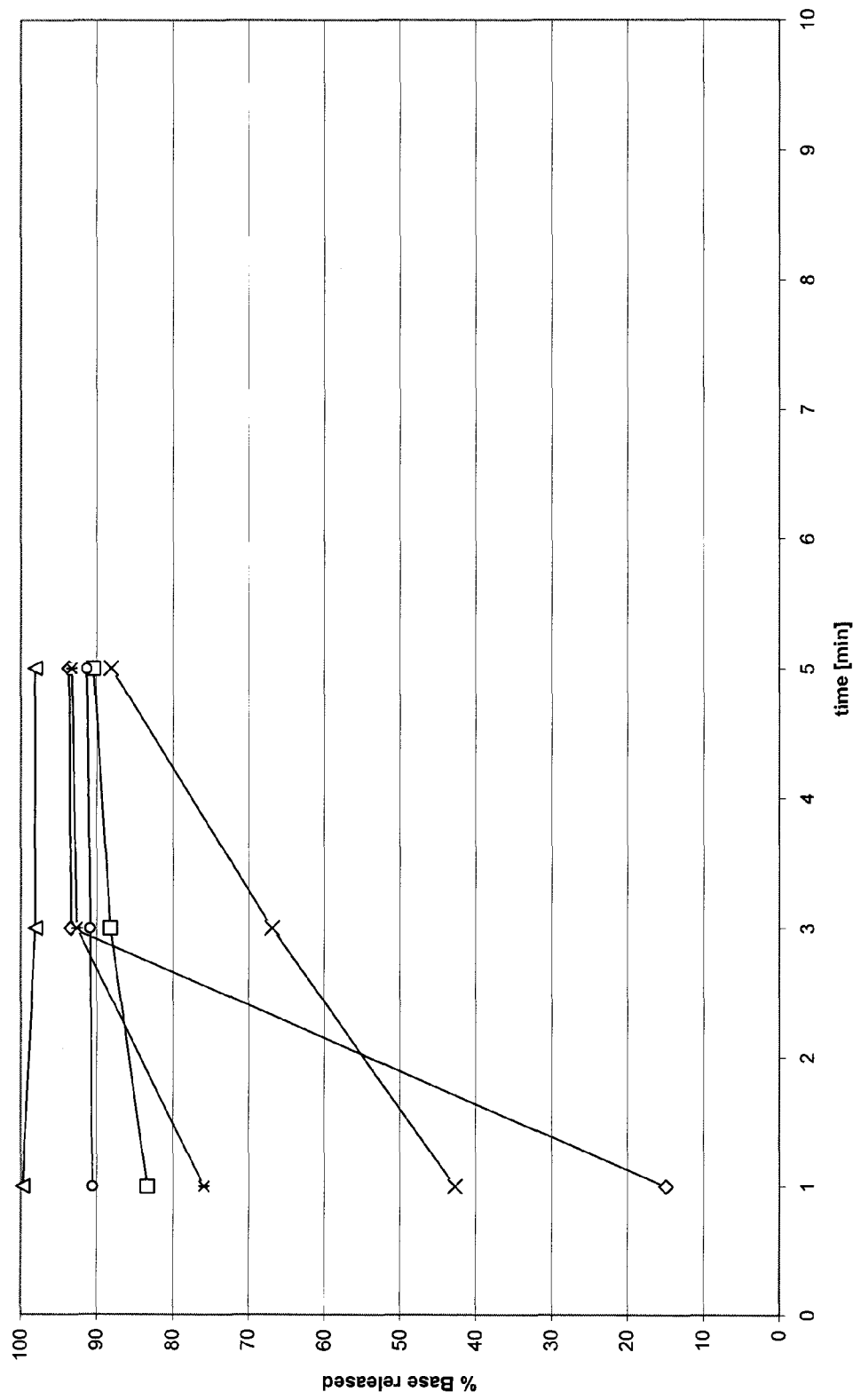
FIG. 12 shows the dissolution curve of tapentadol hydrobromide (media: SIFsp: diamond, square, triangle; SGFsp: cross, asterisk, circle).
Figure 13:
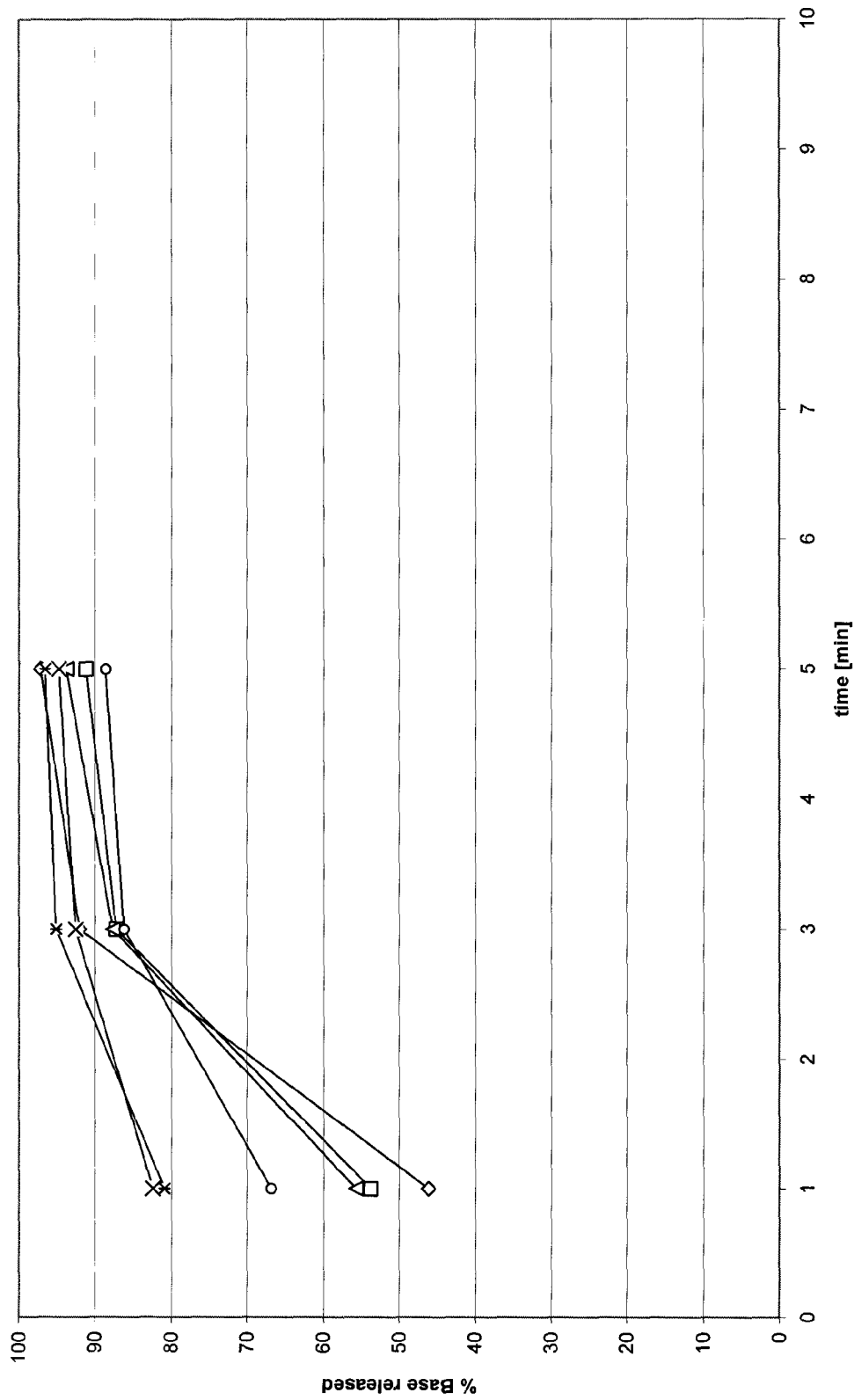
FIG. 13 shows the dissolution curve of tapentadol malonate (media: SIFsp: diamond, square, triangle; SGFsp: cross, asterisk, circle).
Figure 14:
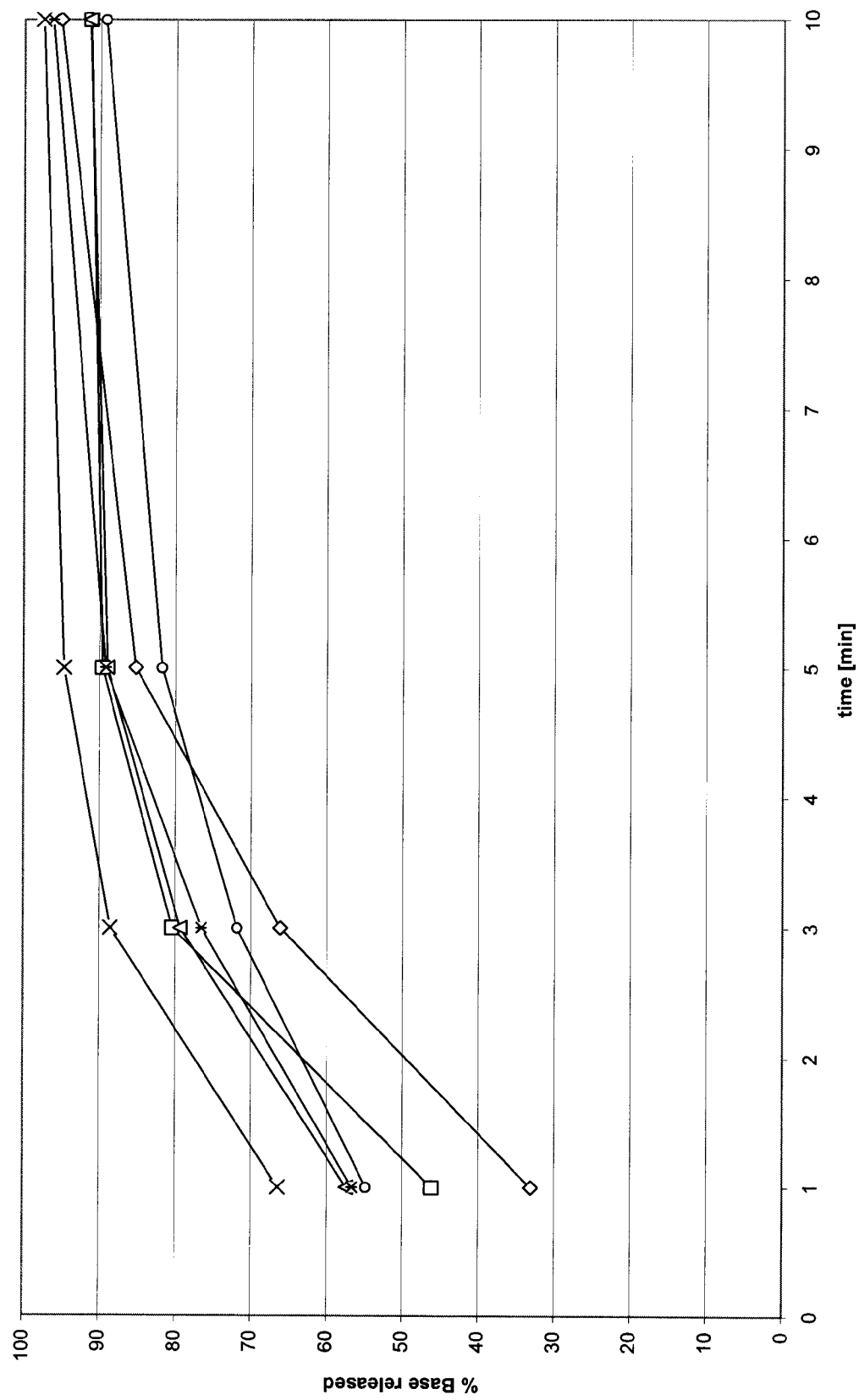
FIG. 14 shows the dissolution curve of tapentadol nitrate (media: SIFsp: diamond, square, triangle; SGFsp: cross, asterisk, circle).
Figure 15:
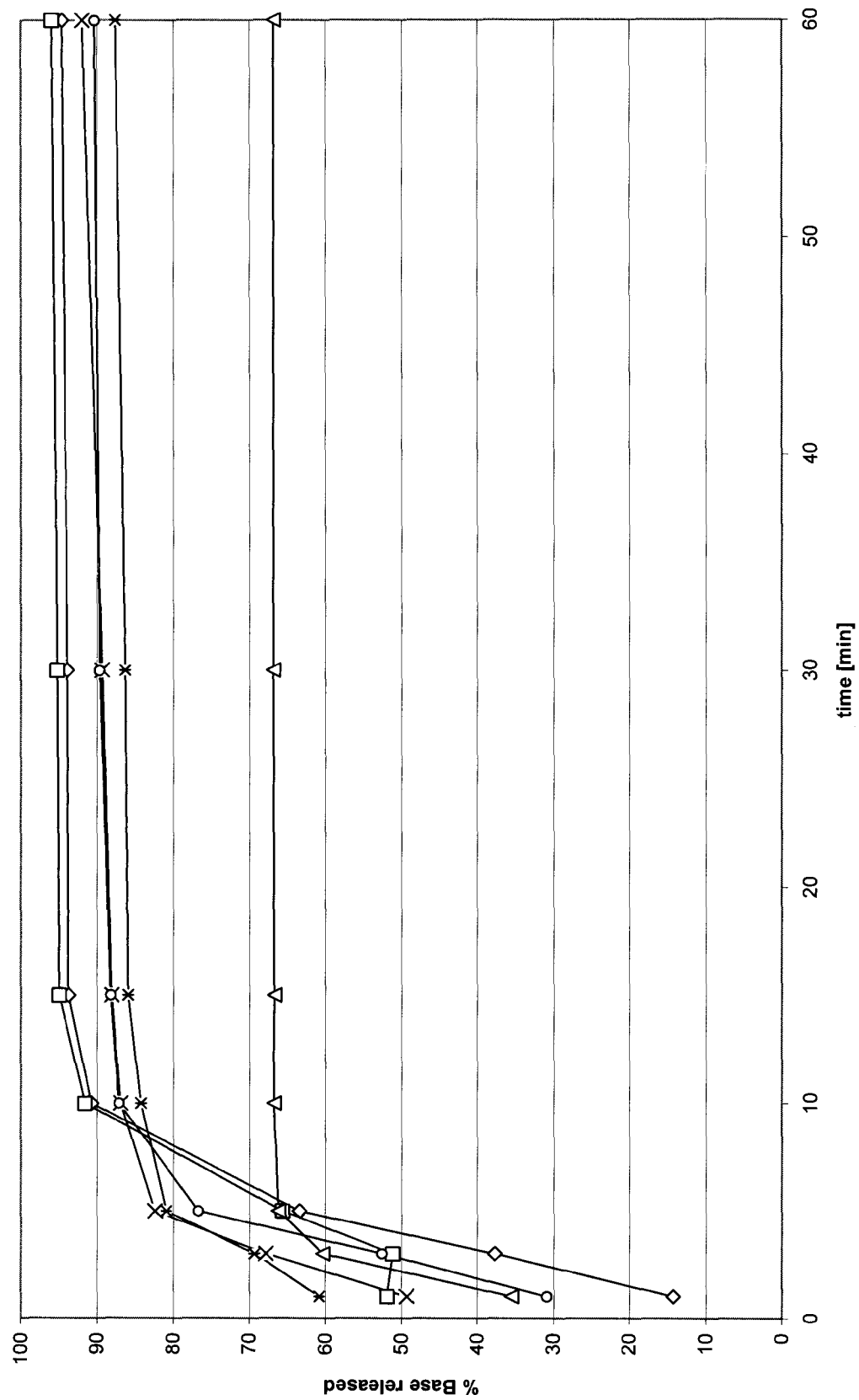
FIG. 15 shows the dissolution curve of tapentadol hemi-fumarate (media: SIFsp: diamond, square, triangle; SGFsp: cross, asterisk, circle).
Figure 16:
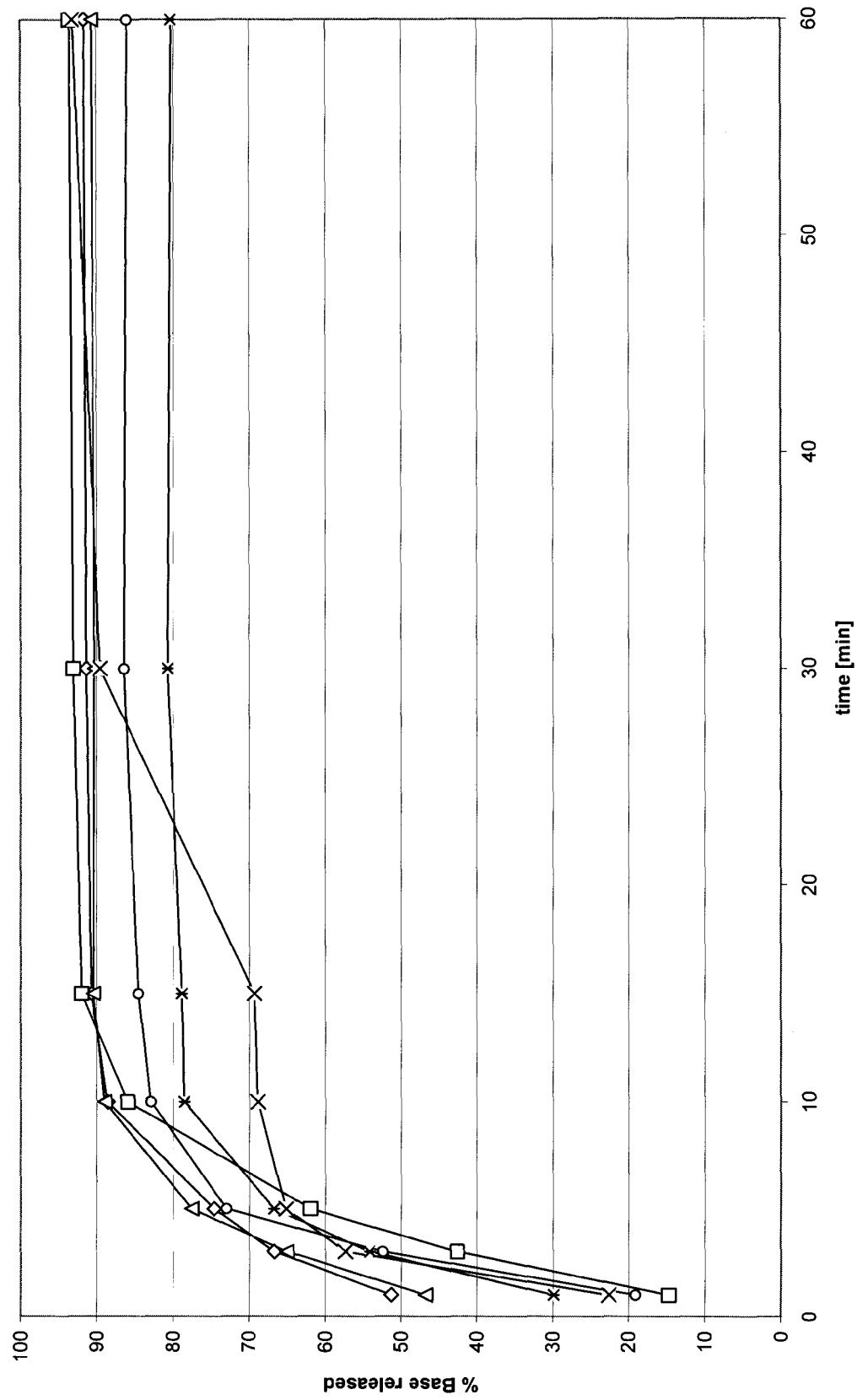
FIG. 16 shows the dissolution curve of tapentadol nicotinate (media: SIFsp: diamond, square, triangle; SGFsp: cross, asterisk, circle).
Figure 17A:
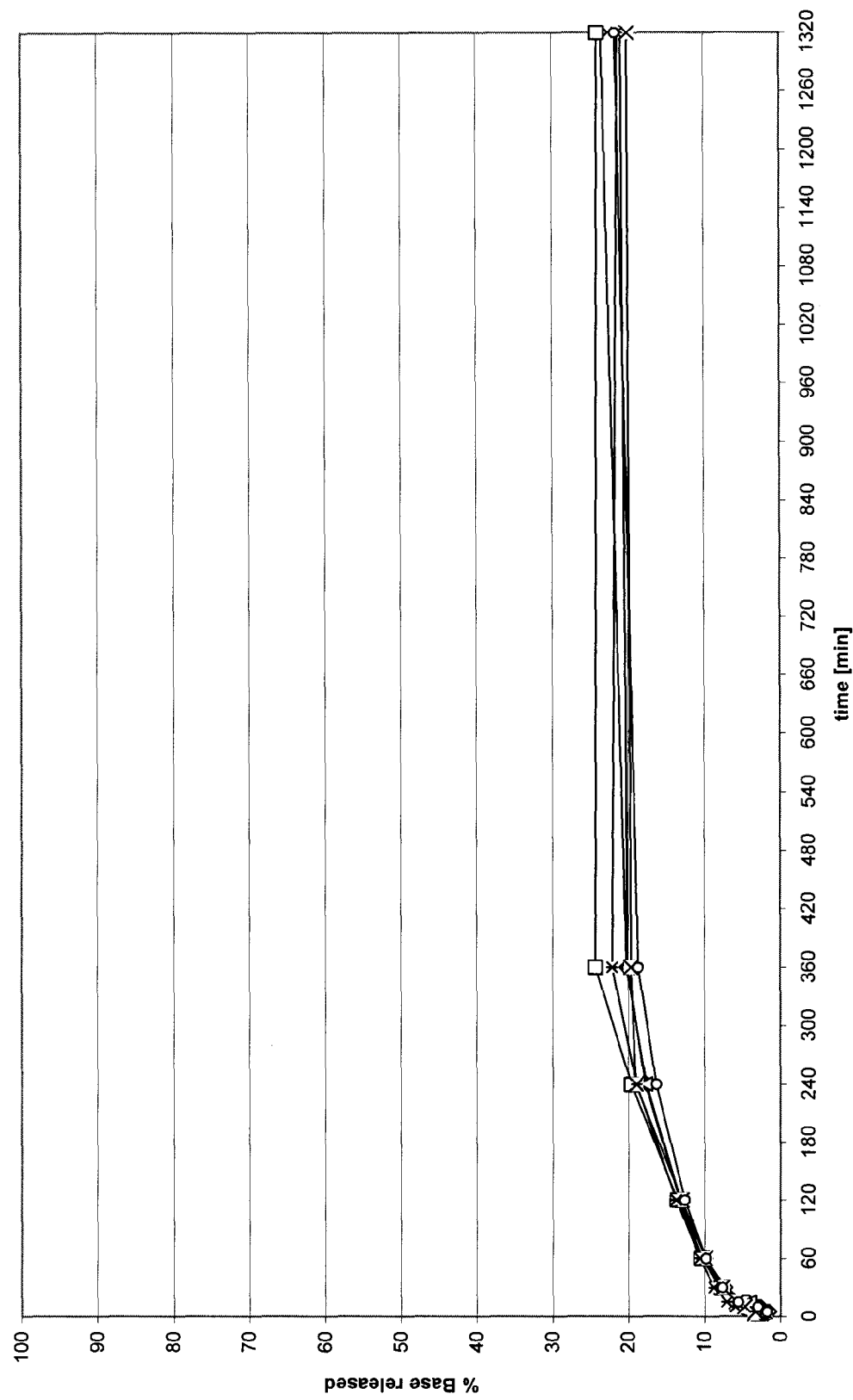
FIG. 17a shows the dissolution curve of tapentadol embonate (media: SGFsp).
Figure 17B:
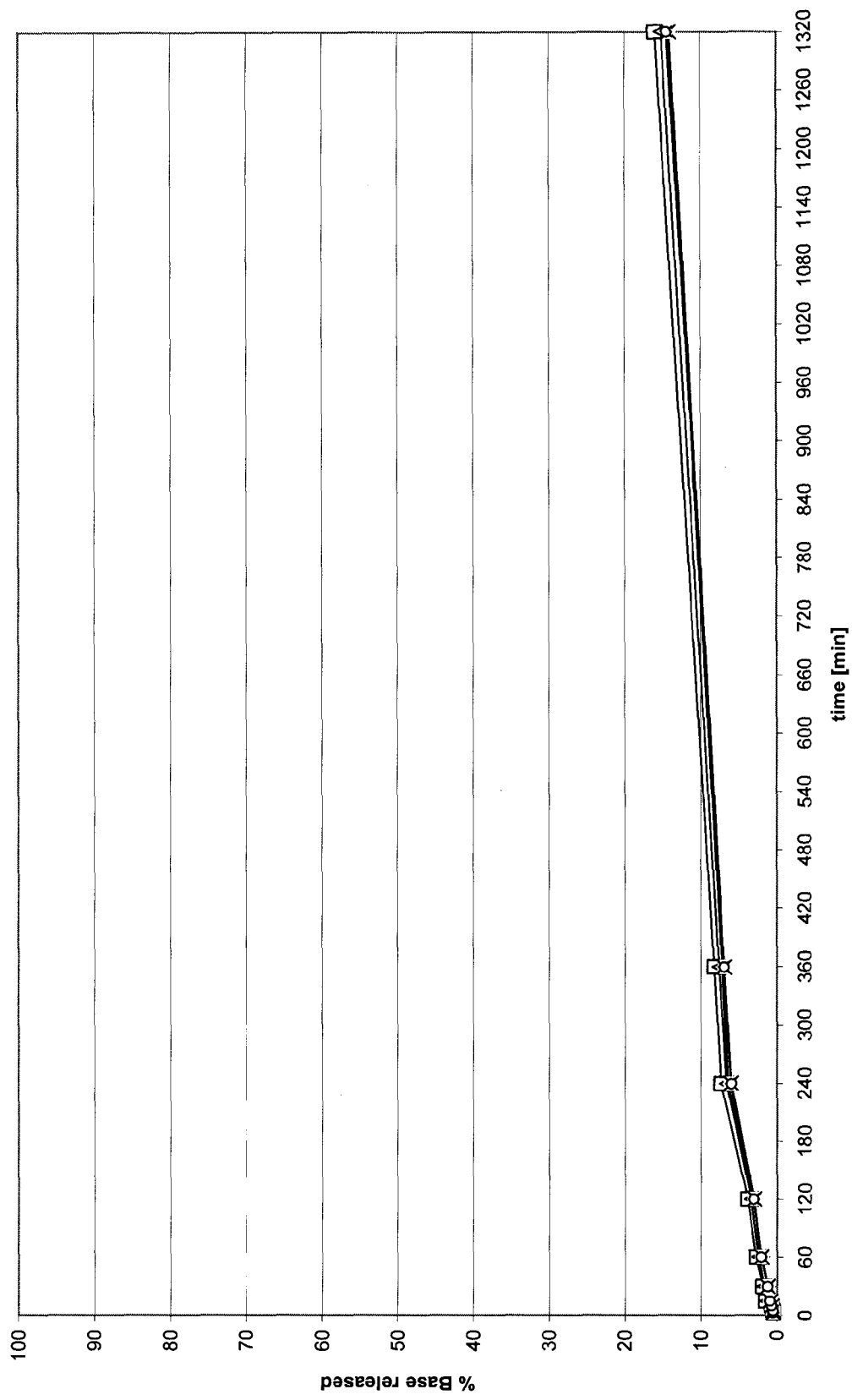
FIG. 17b shows the dissolution curve of tapentadol embonate (media: SIFsp).
Figure 18A:
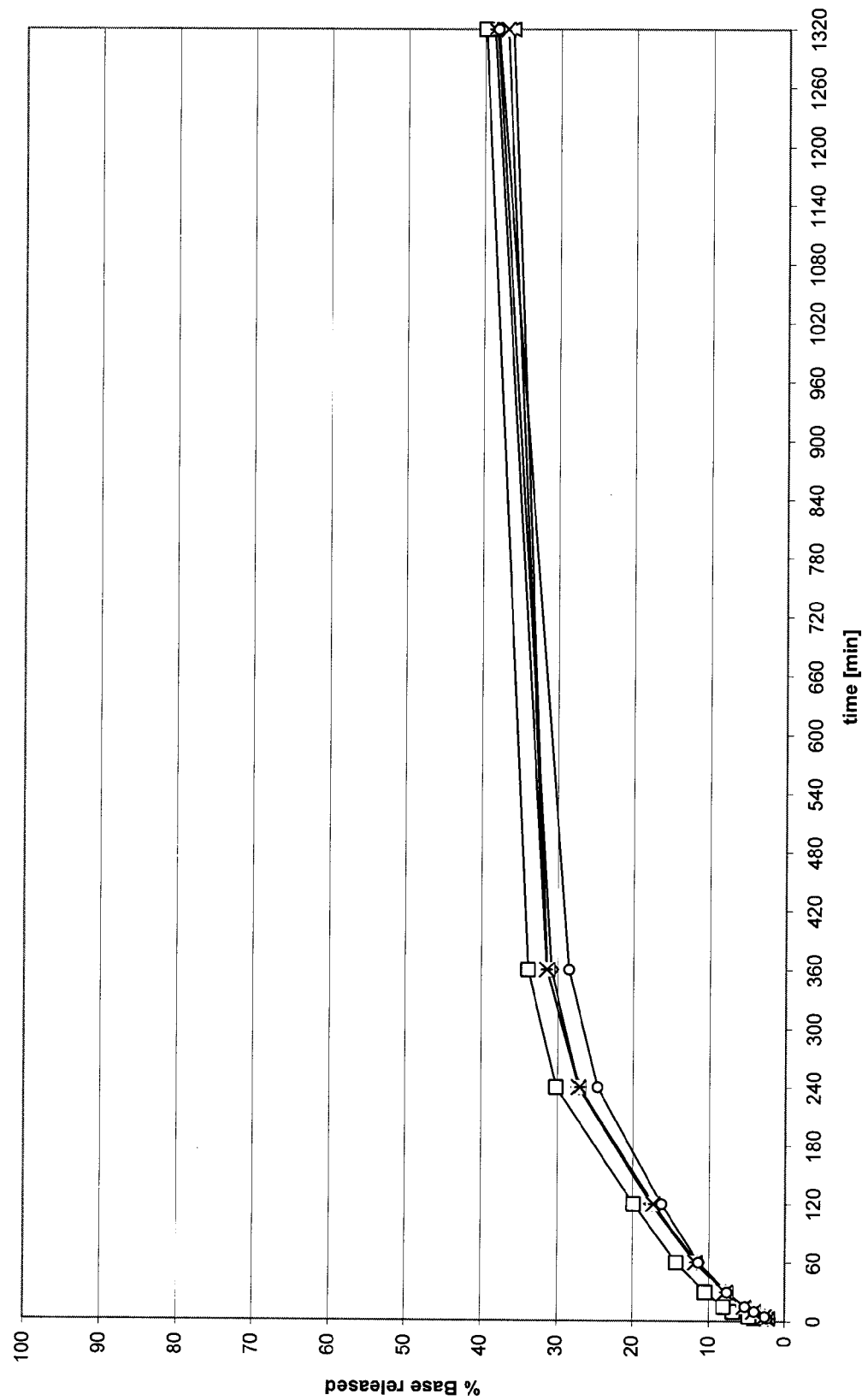
FIG. 18a shows the dissolution curve of tapentadol 1-hydroxy-2-naphthoate (media: SGFsp).
Figure 18B:
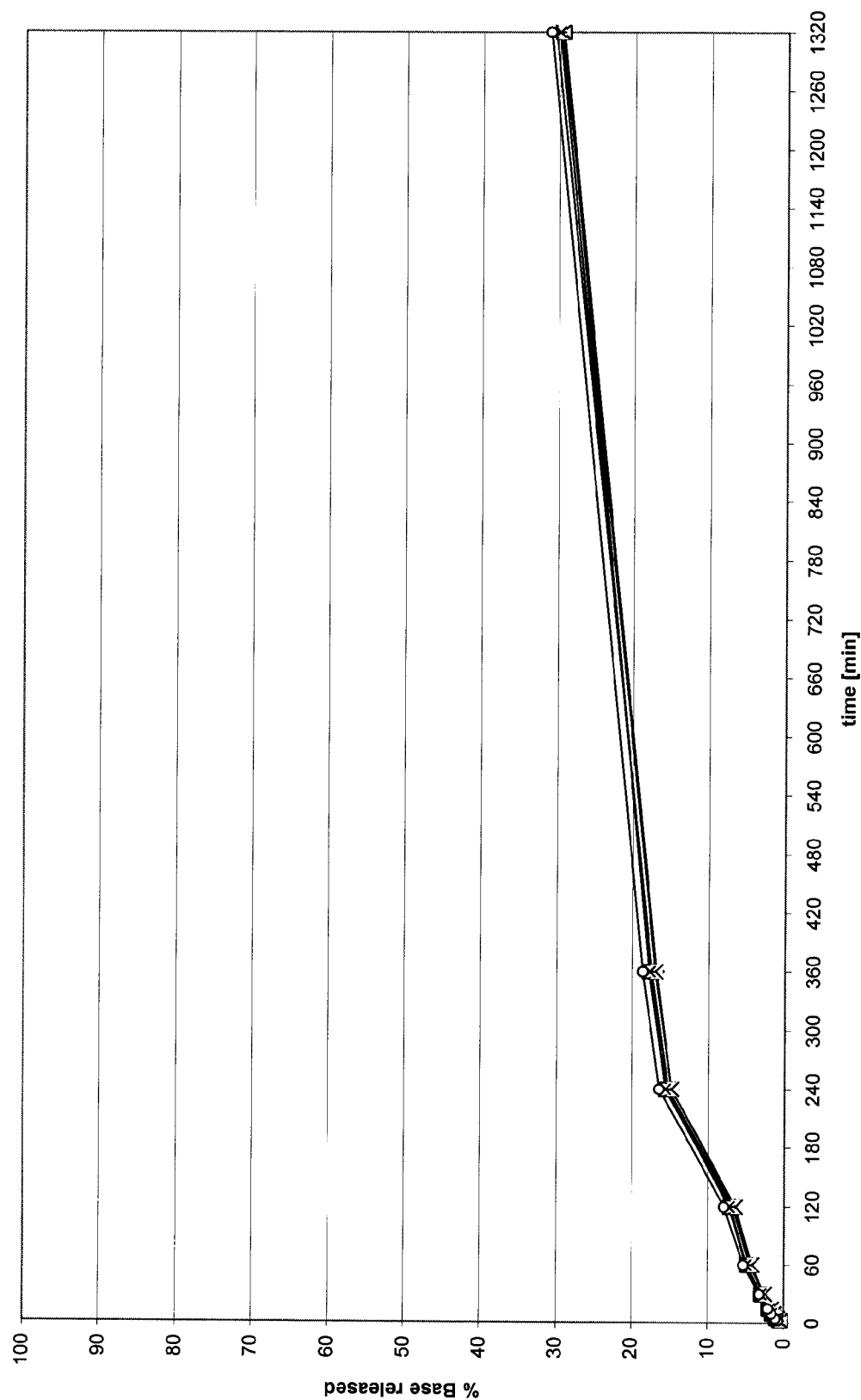
FIG. 18b shows the dissolution curve of tapentadol 1-hydroxy-2-naphthoate (media: SIFsp).
Figure 19A:
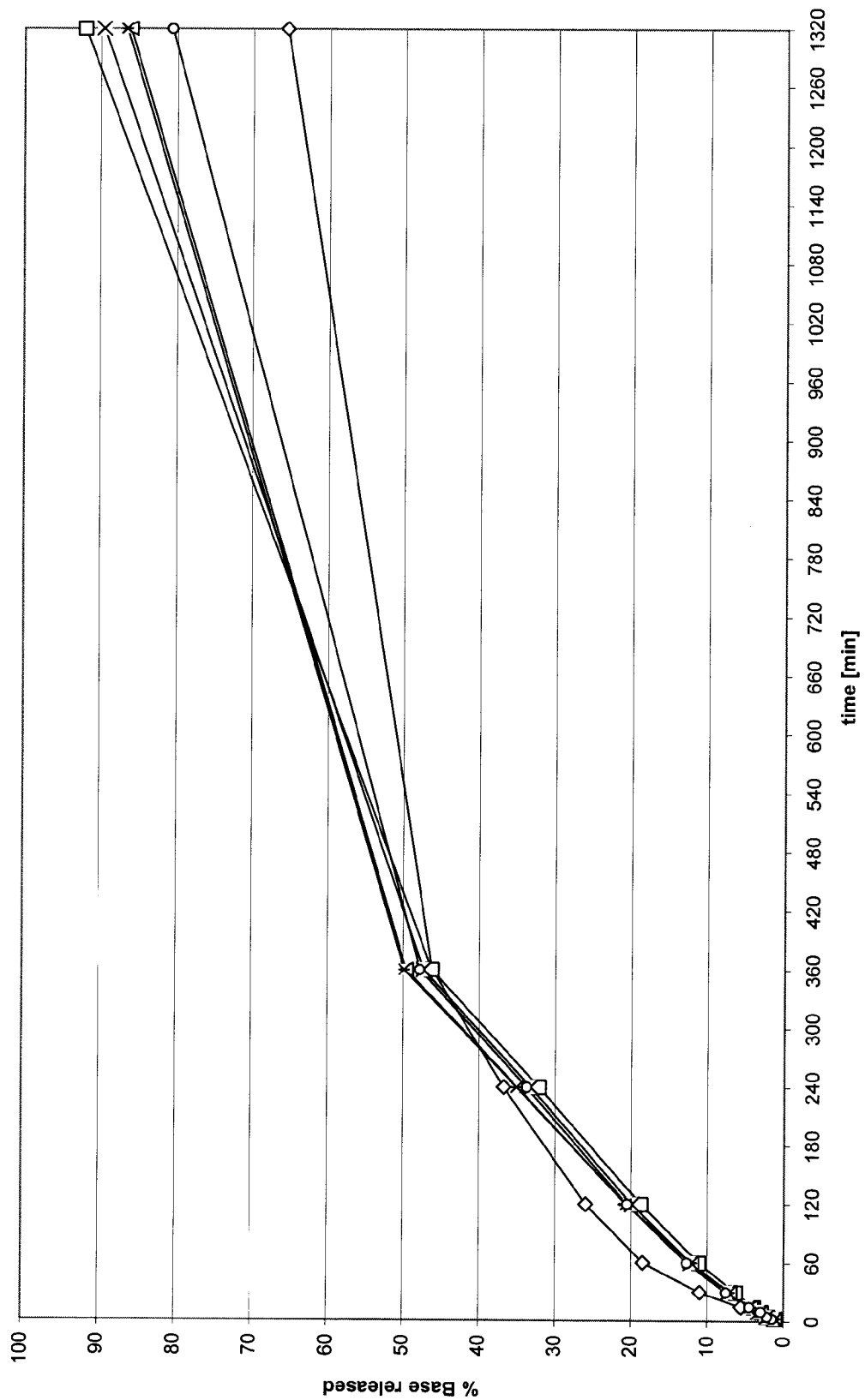
FIG. 19a shows the dissolution curve of tapentadol hemi-(2S,2S)-Di-Benzoyltartrate (media: SGFsp).
Figure 19B:
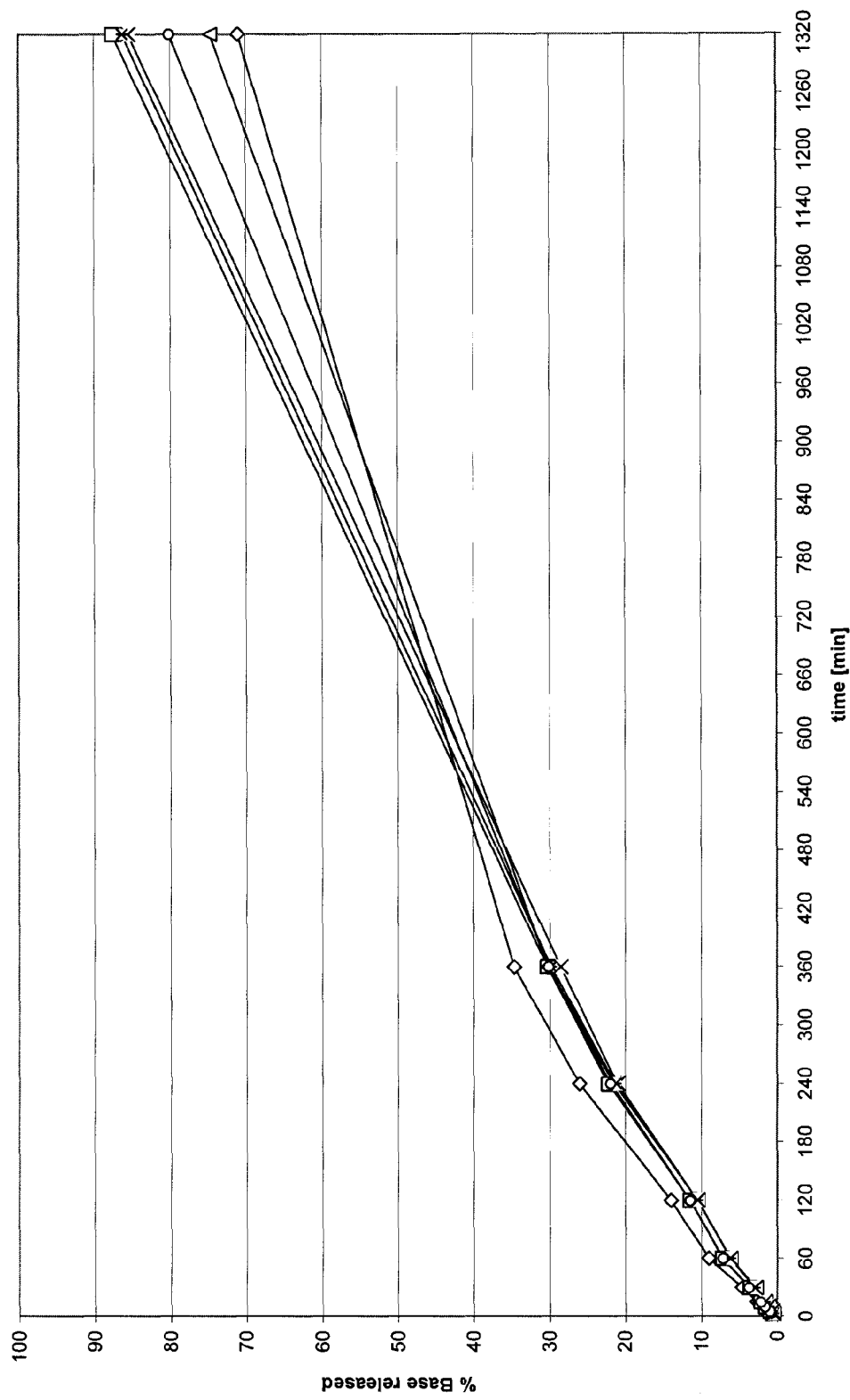
FIG. 19b shows the dissolution curve of tapentadol hemi-(2S,2S)-Di-Benzoyltartrate (media: SIFsp).
Figure 20A:
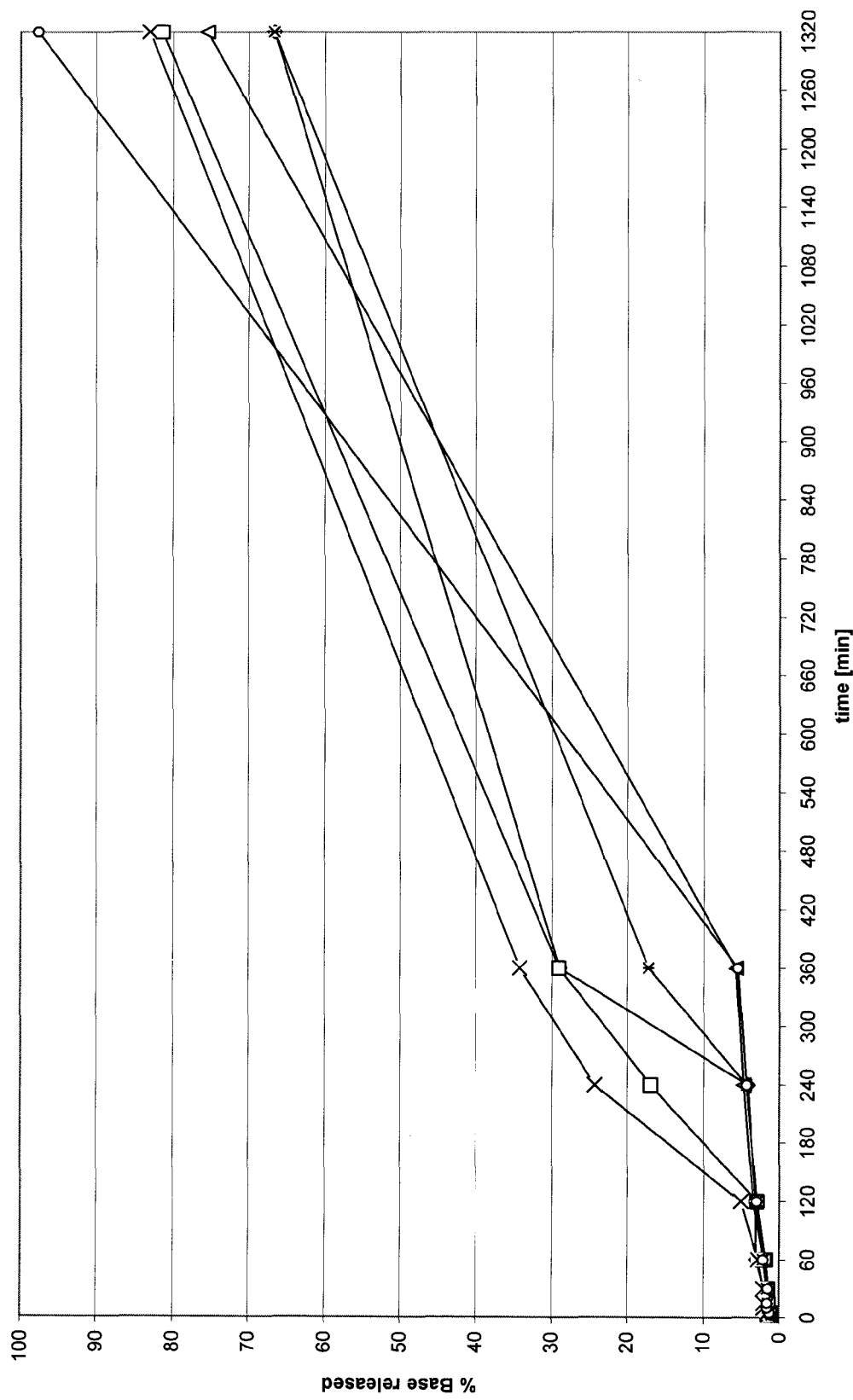
FIG. 20a shows the dissolution curve of tapentadol sebacate (media: SGFsp).
Figure 20B:
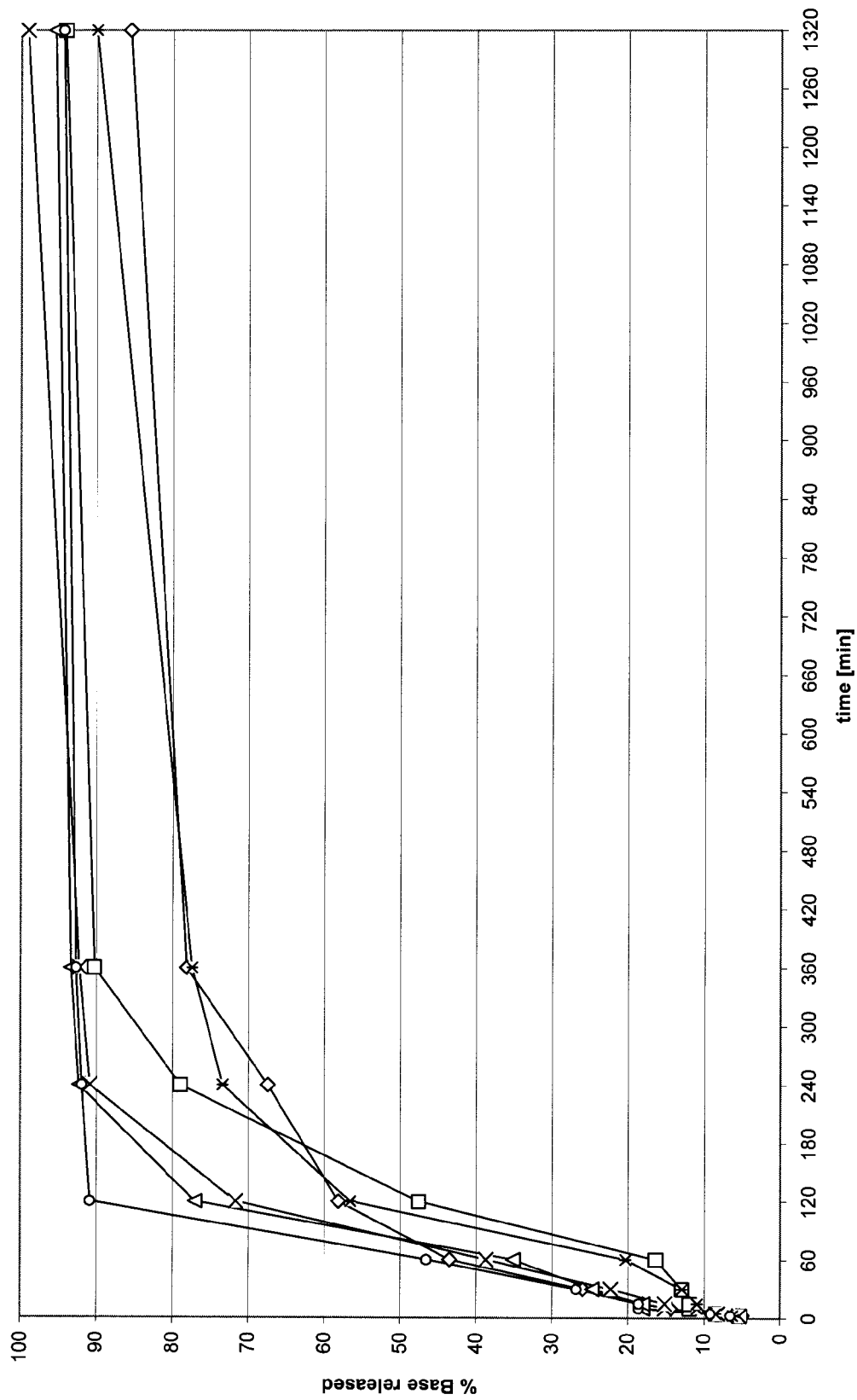
FIG. 20b shows the dissolution curve of tapentadol sebacate (media: SIFsp).
Figure 21A:
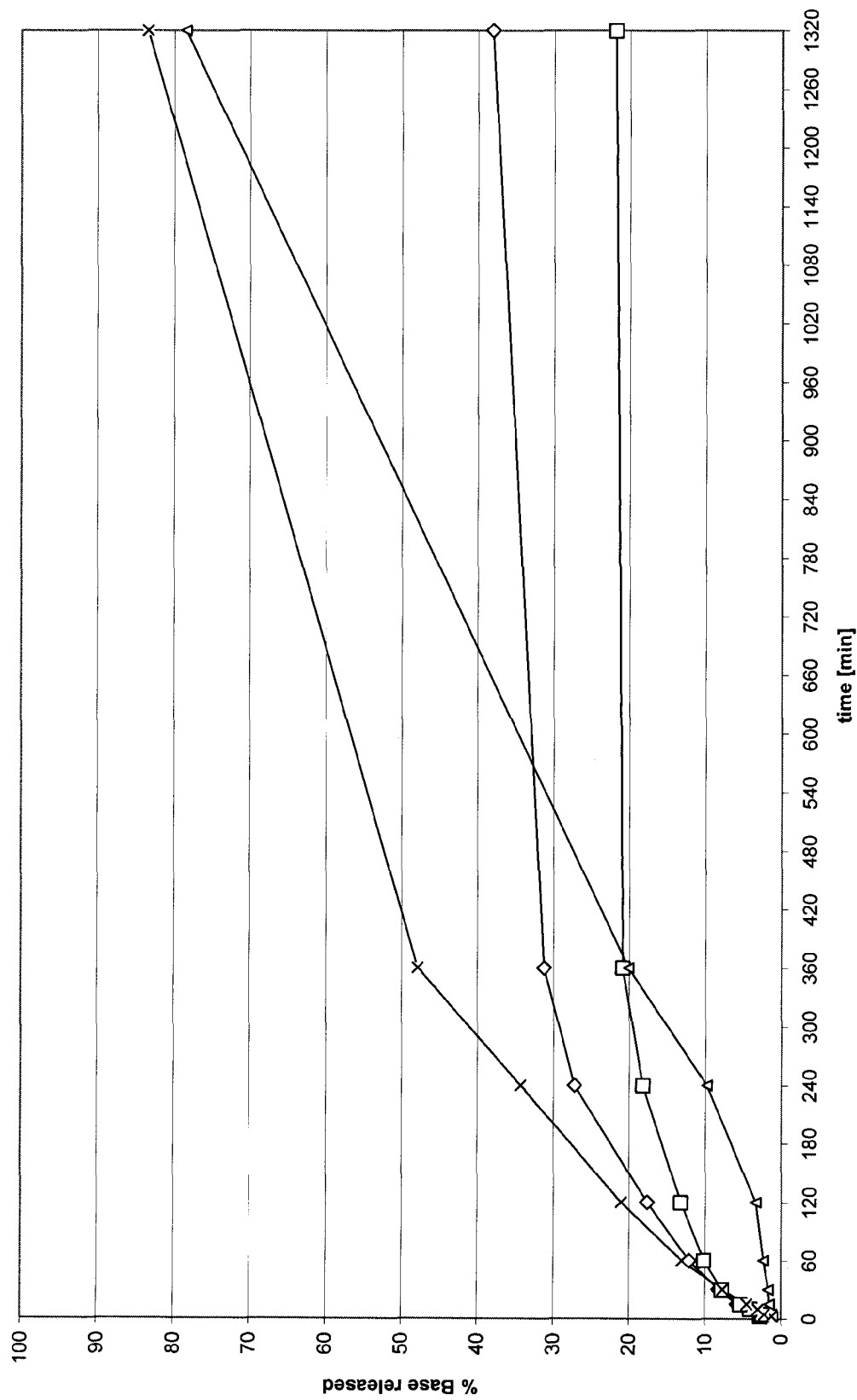
FIG. 21a shows the average of the dissolution curves of tapentadol 1-hydroxy-2-naphthoate (symbol: diamond), tapentadol embonate (symbol: square), tapentadol sebacate (symbol: triangle), and hemi-(2S,2S)-di-benzoyltartrate (symbol: cross) (media: SGFsp).
Figure 21B:
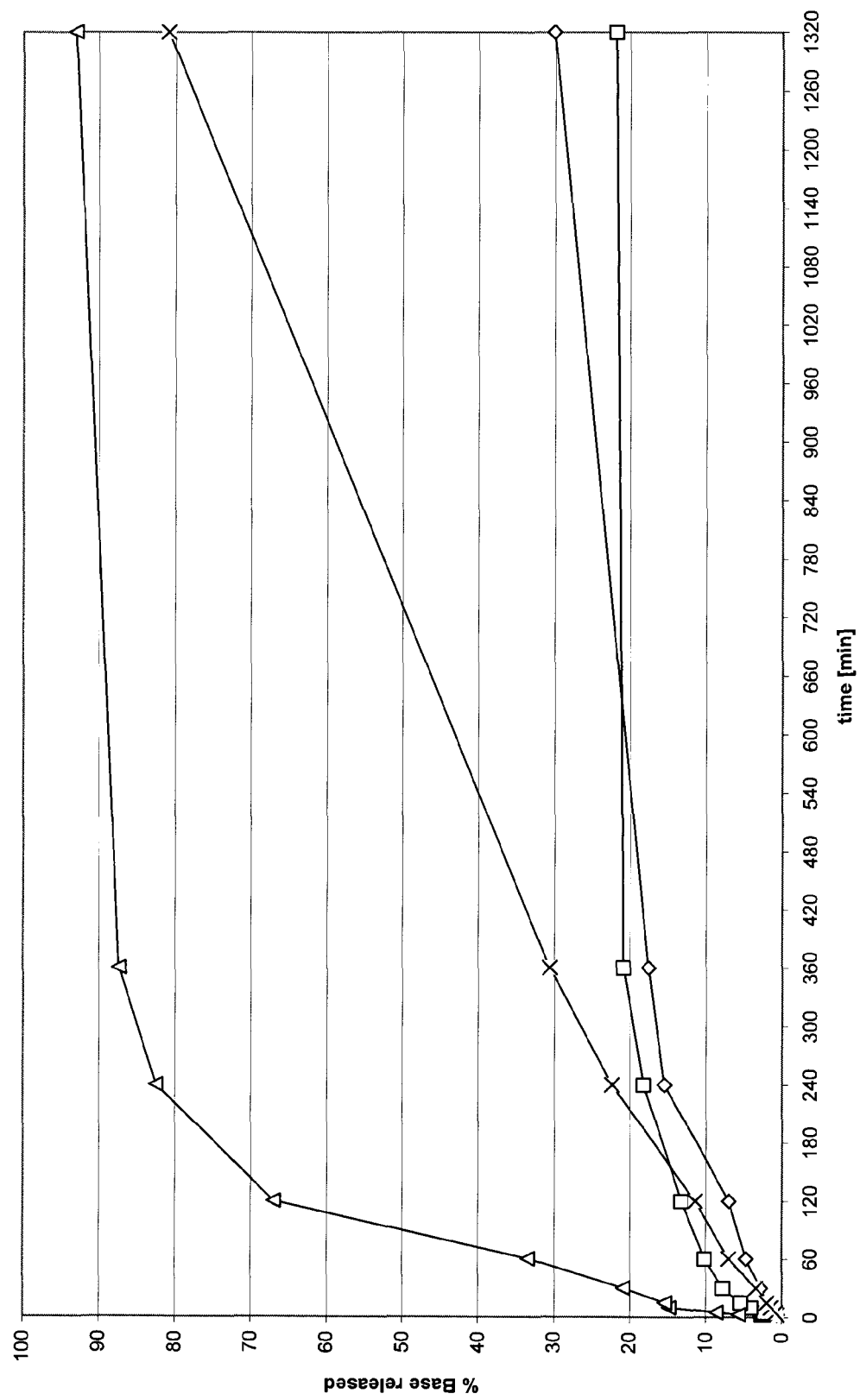
FIG. 21b shows the average of the dissolution curves of tapentadol 1-hydroxy-2-naphthoate (symbol: diamond), tapentadol embonate (symbol: square), tapentadol sebacate (symbol: triangle), and hemi-(2S,2S)-di-benzoyltartrate (symbol: cross) (media: SIFsp).

Dissolutions were performed in the following dissolution media:

SIFsp; intestinal fluid without pancreas powder (pancreatin), pH 6.8 (according to Ph. Eur.);
SGFsp; gastric fluid without pancreas powder (pancreatin), pH 1.2 (according to Ph. Eur.);

Every single dissolution experiment was made in a volume of 900±5 mL (temperature of media: 37±1° C., rotation speed: 100±5 rpm). The content (percentage of base released; % base released) was detected using UV-spectroscopy, wavelength: 271 nm, path length (cuvette): 10 mm. Samples were drawn manually. The dissolution curves are shown in FIGS. 12-21*b*.

In the following tables some of the results of further characterizations of some of the inventive salts or cocrystals, obtained from different samples, are given in detail A) Hemi Salt or Hemi Cocrystal of (2S,3S)-Di-benzoyl Tartaric Acid and Tapentadol

|  | A-1 | A-2 | A-3 |
|---|---|---|---|
| $^1$H-NMR | 1:0.5 | 1:0.5 | 1:0.5 |
| XRPD | crystalline | crystalline | crystalline |
| DSC | To 152.5° C. | To = 190.0° C. | To = 188.5° C. |
|  | Tp 170.7° C. | Tp = 191.2° C. | Tp = 190.1° C. |
|  | 9.7 J/g | 137.8 J/g | 126.6 J/g |
|  | To 185.7° C. |  |  |
|  | Tp 188.2° C. |  |  |
|  | 119.1 J/g |  |  |
| TGA | no weight loss up to 140° C. | no weight loss up to 160° C. | no weight loss up to 160° C. |

B) Salt or Cocrystal of Sebacid Acid and Tapentadol

|  | B-1 | B-2 | B-3 |
|---|---|---|---|
| $^1$H-NMR | 1:1 | 1:1 | 1:1 |
| XRPD | crystalline | crystalline | crystalline |
| DSC | To 78.6° C. | To = 76.6° C. | To = 79.0° C. |
|  | Tp 82.3° C. | Tp = 80.6° C. | Tp = 82.2° C. |
|  | 104.5 J/g | 69.8 J/g | 102.5 J/g |
| TGA | no weight loss up to 140° C. | no weight loss up to 105° C. | no weight loss up to 145° C. |

C) Salt or Cocrystal of 1-hydroxy-2-naphthoic Acid and Tapentadol

|  | C-1 | C-2 |
|---|---|---|
| $^1$H-NMR | 1:1 | 1:1 |
| XRPD | crystalline | crystalline |
| DSC | To 112.4° C. | To = 157.3° C. |
|  | Tp 120.7° C. | Tp = 160.3° C. |
|  | 1.1 J/g | 82.6 J/g ° C. |
|  | To 153.4° C. |  |
|  | Tp 157.4° C. |  |
|  | 69.1 J/g |  |
| TGA | no weight loss up to 125° C. | no weight loss up to 130° C. |

D) Salt or Cocrystal of Embonic Acid and Tapentadol

|  | D-1 | D-2 | D-3 |
|---|---|---|---|
| $^1$H-NMR | 1:1 | 1:1 | 1:1 |
| XRPD | crystalline | crystalline | crystalline |
| DSC | To 127.2° C. | To = 221.7° C. | To = 217.2° C. |
|  | Tp 130.6° C. | Tp = 225.0° C. | Tp = 220.0° C. |
|  | 38.7 J/g | 56.1 J/g | 62.9 J/g |
|  | To 141.3° C. |  |  |
|  | Tp 149.2° C. |  |  |
|  | −6.0 J/g |  |  |
|  | To 209.9° C. |  |  |
|  | Tp 218.9° C. |  |  |
|  | 46.0 J/g |  |  |
| TGA | −7.1% | no weight loss up | no weight loss up |
|  | (90° C.-157° C.) | to 170° C. | to 160° C. |

E) Salt or Cocrystal of Malonic Acid and Tapentadol

|  | E-1 |
|---|---|
| $^1$H-NMR | 1:1 |
| XRPD | crystalline |
| DSC | To 109.8° C. |
|  | Tp 111.4° C. |
|  | 86.9 J/g |
| TGA | no weight loss up |
|  | to 115° C. |

F) Salt or Cocrystal of Hydrobromic Acid and Tapentadol

|  | F-1 |
|---|---|
| $^1$H-NMR | 1:1 |
| XRPD | crystalline |
| DSC | To 184.9° C. |
|  | Tp 185.4° C. |
|  | 110.4 J/g |
| TGA | no weight loss up |
|  | to 195° C. |

G) Salt or Cocrystal of Nicotinic Acid and Tapentadol

|  | G-1 | G-2 | G-3 | G-4 |
|---|---|---|---|---|
| $^1$H-NMR | 1:1 | 1:1 | 1:1 | 1:1 |
| XRPD | crystalline | crystalline | crystalline | crystalline |
| DSC | To 69.4° C. | To 103.1° C. | To = 102.7° C. | To = 48.8° C. |
|  | Tp 74.4° C. | Tp 105.4° C. | Tp = 105.2° C. | Tp = 65.3° C. |
|  | 100.9 J/g | 87.0 J/g | 100.9 J/g | 8.3 J/g |
|  |  |  |  | To = 103.3° C. |
|  |  |  |  | Tp = 105.2° C. |
|  |  |  |  | 99.6 J/g |
| TGA | −6.4% | no weight | no weight | no weight |
|  | (28° C.- | loss up | loss up | loss up |
|  | 171° C.) | to 135° C. | to 150° C. | to 135° C. |

H) Salt or Cocrystal of Nitric Acid and Tapentadol

|  | H-1 |
|---|---|
| $^1$H-NMR | 1:1 |
| XRPD | crystalline |
| DSC | To 86.9° C. |
|  | Tp 88.2° C. |
|  | 0.37 J/g |
|  | To 119.7° C. |
|  | Tp 121.3° C. |
|  | 119.3 J/g |
| TGA | no weight loss up |
|  | to 170° C. |

I) Hemi Salt or Hemi Cocrystal of Fumaric Acid and Tapentadol

|  | I-1 | I-2 | I-3 |
|---|---|---|---|
| $^1$H-NMR | 1:0.5 | 1:0.5 | 1:0.5 |
| XRPD | crystalline | crystalline | crystalline |
| DSC | To 134.0° C. | To = 131.8° C. | To = 133.9° C. |
|  | Tp 135.7° C. | Tp = 133.9° C. | Tp = 135.2° C. |
|  | 125.1 J/g | 105.4 J/g | 124.9 J/g |
| TGA | no weight loss up | no weight loss up | no weight loss up |
|  | to 131° C. | to 130° C. | to 130° C. |

J) Salt or Cocrystal of Saccharin and Tapentadol

|  | J-1 |
|---|---|
| $^1$H-NMR | 1:1 |
| XRPD | crystalline |
| DSC | To = 110.3° C. |
|  | Tp = 112.8° C. |
|  | 77.3 J/g |
| TGA | no weight loss up |
|  | to 105° C. |

The foregoing description and examples have been set forth merely to illustrate the invention and are not intended to be limiting. Since modifications of the described embodiments incorporating the spirit and substance of the invention may occur to persons skilled in the art, the invention should be construed broadly to include all variations within the scope of the appended claims and equivalents thereof.

The invention claimed is:

1. A salt or cocrystal of
   (a) (1R,2R)-3-(3-dimethylamino-1-ethyl-2-methyl-propyl)-phenol, and
   (b1) at least one acid selected from the group consisting of embonic acid, (2S,3S)-dibenzoyltartaric acid, sebacic acid, and 1-hydroxy-2-naphthoic acid, or
   (b2) at least one acid selected from the group consisting of nicotinic acid, hydrogen bromide, fumaric acid, and malonic acid
   wherein the salt or cocrystal of component (a) and component (b1) or the salt or cocrystal of component (a) and component (b2) is present in crystalline form, and
   wherein said crystalline form is selected from the group consisting of:
   a salt or cocrystal of embonic acid and (1R,2R)-3-(3-dimethylamino-1-ethyl-2-methyl-propyl)-phenol having at least one or more X-ray diffraction peaks selected from the group consisting of 7.94±0.20 (2θ), 10.40±0.20 (2θ), 14.25±0.20 (2θ), 17.18±0.20 (2θ) and 18.77±0.20 (2θ) or at least one or more X-ray diffraction peaks selected from the group consisting of 6.00±0.20 (2θ), 11.96±0.20 (2θ) and 17.61±0.20 (2θ);
   a hemi salt or cocrystal of (2S,3S)-dibenzoyltartaric acid and (1R,2R)-3-(3-dimethylamino-1-ethyl-2-methyl-propyl)-phenol having at least one or more X-ray diffraction peaks selected from the group consisting of 9.35±0.20 (2θ), 12.22±0.20 (2θ), 13.41±0.20 (2θ), 14.00±0.20 (2θ), 17.89±0.20 (2θ), 18.28±0.20 (2θ), 18.73±0.20 (2θ), 19.53±0.20 (2θ), 19.98±0.20 (2θ), 23.19±0.20 (2θ) and 24.33±0.20 (2θ);

a salt or cocrystal of sebacic acid and (1R,2R)-3-(3-dimethylamino-1-ethyl-2-methyl-propyl)-phenol having at least one or more X-ray diffraction peaks selected from the group consisting of 12.16±0.20 (2θ), 15.31±0.20 (2θ), 16.88±0.20 (2θ), 18.90±0.20 (2θ), 22.66±0.20 (2θ), 23.08±0.20 (2θ) and 25.46±0.20 (2θ);

a salt or cocrystal of 1-hydroxy-2-naphthoic acid and (1R,2R)-3-(3-dimethylamino-1-ethyl-2-methyl-propyl)-phenol having at least one or more X-ray diffraction peaks selected from the group consisting of 13.59±0.20 (2θ), 13.97±0.20 (2θ), 15.36±0.20 (2θ), 18.04±0.20 (2θ), 19.75±0.20 (2θ), 19.98±0.20 (2θ), 20.52±0.20 (2θ), 24.37±0.20 (2θ) and 26.09±0.20 (2θ);

a salt or cocrystal of nicotinic acid and (1R,2R)-3-(3-dimethylamino-1-ethyl-2-methyl-propyl)-phenol having at least one or more X-ray diffraction peaks selected from the group consisting of 12.60±0.20 (2θ), 15.61±0.20 (2θ) and 22.82±0.20 (2θ) or at least one or more X-ray diffraction peaks selected from the group consisting of 10.34±0.20 (2θ), 12.14±0.20 (2θ), 22.38±0.20 (2θ), 23.65±0.20 (2θ) and 26.11±0.20 (2θ);

a salt or cocrystal of hydrobromic acid and (1R,2R)-3-(3-dimethylamino-1-ethyl-2-methyl-propyl)-phenol having at least one or more X-ray diffraction peaks selected from the group consisting of 9.93±0.20 (2θ), 14.39±0.20 (2θ), 15.22±0.20 (2θ), 17.60±0.20 (2θ), 20.81±0.20 (2θ), 21.61±0.20 (2θ), 24.37±0.20 (2θ), 24.73±0.20 (2θ), 25.19±0.20 (2θ), 27.14±0.20 (2θ), 27.94±0.20 (2θ), 29.00±0.20 (2θ) and 30.75±0.20 (2θ);

a salt or cocrystal of malonic acid and (1R,2R)-3-(3-dimethylamino-1-ethyl-2-methyl-propyl)-phenol having at least one or more X-ray diffraction peaks selected from the group consisting of 8.75±0.20 (2θ), 11.85±0.20 (2θ), 13.74±0.20 (2θ), 16.78±0.20 (2θ), 18.09±0.20 (2θ), 19.17±0.20 (2θ), 16.65±0.20 (2θ), 20.45±0.20 (2θ), 21.66±0.20 (2θ), 24.80±0.20 (2θ) and 25.55±0.20 (2θ); and a hemi salt or cocrystal of fumaric acid and (1R,2R)-3-(3-dimethylamino-1-ethyl-2-methyl-propyl)-phenol having at least one or more X-ray diffraction peaks selected from the group consisting of 11.86±0.20 (2θ), 15.26±0.20 (2θ), 16.00±0.20 (2θ), 16.21±0.20 (2θ), 17.52±0.20 (2θ), 21.75±0.20 (2θ), 22.35±0.20 (2θ), 24.57±0.20 (2θ) and 25.21±0.20 (2θ).

2. The salt or cocrystal according to claim 1, wherein component (b1) is selected from the group consisting of embonic acid, sebacic acid, and 1-hydroxy-2-naphthoic acid.

3. The salt or cocrystal according to claim 1, wherein component (b1) is selected from the group consisting of (2S, 3S)-dibenzoyltartaric acid, sebacic acid, 1-hydroxy-2-naphthoic acid, and embonic acid.

4. The salt or cocrystal according to claim 1, wherein component (b2) is selected from the group consisting of nicotinic acid, hydrogen bromide, fumaric acid, and malonic acid.

5. The salt or cocrystal according to claim 4, wherein component (b2) is nicotinic acid.

6. The salt or cocrystal according to claim 1, wherein the stoichiometry of component (a) and (b1) or (b2) is within the range of from 1:0.4 to 1:2.1.

7. The salt or cocrystal according to claim 6, wherein the stoichiometry of component (a) and (b1) or (b2) is within the range of from 1:0.4 to 1:1.

8. A pharmaceutical composition comprising a salt or cocrystal according to claim 1 and at least one pharmaceutically acceptable carrier or auxiliary.

9. A pharmaceutical composition according to claim 8, in the form of a solid tablet.

10. A pharmaceutical composition according to claim 8, wherein said composition is formulated for oral administration.

11. A method of treating pain in a subject in need thereof, said method comprising administering an effective pain relieving amount of a salt or cocrystal according to claim 1 to said subject.

12. A method according to claim 11, wherein the pain is selected from the group consisting of inflammatory pain, neuropathic pain, acute pain, chronic pain, visceral pain, migraine pain and pain associated with cancer.

13. A method according to claim 11, wherein said subject is a mammal.

14. A pharmaceutical composition comprising a salt or cocrystal according to claim 8, wherein component (b1) is selected from the group consisting of embonic acid, sebacic acid, and 1-hydroxy-2-naphthoic acid.

15. A pharmaceutical composition comprising a salt or cocrystal according to claim 8, wherein component (b2) is selected from the group consisting of nicotinic acid, hydrogen bromide fumaric acid, and malonic acid.

16. A pharmaceutical composition comprising a salt or cocrystal according to claim 8, wherein the stoichiometry of component (a) and (b1) or (b2) is within the range of from 1:0.4 to 1:2.1.

17. A pharmaceutical composition comprising a salt or cocrystal according to claim 8, wherein the stoichiometry of component (a) and (b1) or (b2) is within the range of from 1:0.4 to 1:1.

* * * * *